US008158766B2

(12) United States Patent
Yamanaka et al.

(10) Patent No.: US 8,158,766 B2
(45) Date of Patent: Apr. 17, 2012

(54) GENES WITH ES CELL-SPECIFIC EXPRESSION

(75) Inventors: Shinya Yamanaka, Osaka (JP); Eiko Kaiho, Nara (JP)

(73) Assignees: Shinya Yamanaka, Osaka-shi (JP); Dainippon Sumitomo Pharma Co., Ltd., Osaka-shi (JP)

( * ) Notice: Subject to any disclaimer, the term of this patent is extended or adjusted under 35 U.S.C. 154(b) by 1136 days.

(21) Appl. No.: 11/483,880

(22) Filed: Jul. 10, 2006

(65) Prior Publication Data

US 2006/0292620 A1    Dec. 28, 2006

Related U.S. Application Data

(62) Division of application No. 10/479,334, filed as application No. PCT/JP02/05350 on May 31, 2002, now Pat. No. 7,250,255.

(30) Foreign Application Priority Data

May 31, 2001    (JP) ................................ 2001-165927

(51) Int. Cl.
*C07H 21/02* (2006.01)
*C07H 21/04* (2006.01)
(52) U.S. Cl. .................. 536/23.1; 536/24.3; 435/252.3; 435/70.1
(58) Field of Classification Search .................. None
See application file for complete search history.

(56) References Cited

U.S. PATENT DOCUMENTS

| | | | |
|---|---|---|---|
| 5,808,007 | A | 9/1998 | Lee et al. |
| 6,146,888 | A | 11/2000 | Smith et al. |
| 2003/0017480 | A1 | 1/2003 | Ota et al. |
| 2003/0082776 | A1 | 5/2003 | Ota et al. |
| 2003/0157569 | A1 | 8/2003 | Ota et al. |

FOREIGN PATENT DOCUMENTS

| | | |
|---|---|---|
| EP | 1 074 617 A2 | 2/2001 |
| WO | WO 94/15965 A1 | 7/1994 |
| WO | WO 94/24274 A1 | 10/1994 |
| WO | WO 99/14372 A1 | 3/1999 |
| WO | WO 99/18989 A1 | 4/1999 |
| WO | WO 00/05248 A1 | 2/2000 |
| WO | WO 01/27249 A1 | 4/2001 |
| WO | WO 01/57266 A1 | 8/2001 |

OTHER PUBLICATIONS

GenBank Locus X00419, GI: 30205 (Dec. 6, 1983) 'Human c-Ha-ras2 oncogene (*Harvey ras* family).' from www.ncbi.nlm.nih.gov, 2 printed pages.*
Esteban L.M. et al. Molecular and Cellular Biology, Mar. 2001, p. 1444-1452.*
Aapola et al., *Genomics*, 65(3), 293-298 (May 2000).
Astigiano et al., *Differentiation*, 46, 61-67 (1991).
Caricasole et al., *Oncogene*, 16, 95-103 (1998).
Jones et al., *Molecular Endocrinology*, 6, 1961-1968 (1992).
Kirchhof et al., *Biology of Reproduction*, 63, 1698-1705 (2000).
Matsuda et al., *Experimental Medicine*, 19(3), 330-338 (2001).
Okamoto et al., *Cell*, 60, 461-472 (Feb. 9, 1990).
Takeda et al., *Nucleic Acids Research*, 20(17), 4613-4620 (Sep. 1992).
Winston et al., *Current Biology*, 9 (20), 1180-1182 and S1-S3 (Oct. 1999).
"*Mus musculus* ES cells cDNA, Riken full-length enriched library, clone:241000A20 product: hypothetical Alanine-rich region containing protein, full insert sequence," *Database EMBL Online*: EBI accession No. EM_PRO:AK010377 (Feb. 8, 2001).
"*Homo sapiens* cDNA FLJ12581 fis," *Database EMBL Online*: EBI accession No. AK022643 (Sep. 29, 2000).
Ota et al., "Primer sets for synthesizing polynucleotides," *Database EMBL Online*: EBI accession No. AAH15883 (Jun. 26, 2001).
"*Mus musculus* ES cell cDNA," *Database EMBL Online*: EBI accession No. AK010332 (Feb. 8, 2001).
"*Mus musculus* ES cells cDNA, Riken full-length enriched library, clone: 2410115K01, 3'end partial sequence," *Database EMBL Online*: EBI accession No. EM_PRO: AV212609 (Oct. 29, 1999).
"Human c-Ha-ras2 oncogene (*Harvey ras* family)," *Database EMBL Online*: EBI accession No. EM_PRO: X00419 (Dec. 6, 1983).
Miyoshi et al., *Nucleic Acids Research*, 12(4): 1821-1828 (Feb. 24, 1984).
Riken Genome Exploration Research Group Phase II Team (Kawai et al.) and FANTOM Consortium (Okazaki et al.), *Nature*, 409: 685-690 (Feb. 8, 2001), with Genbank accession No. AK010332 (EMBL: Feb. 8, 2001).
Kargul et al., *Nature Genetics*, 28(1): 17-18 (May 2001), with Genbank accession No. BG080126 (EMBL: Jan. 29, 2001) and Genbank accession No. BG067052 (EMBL: Jan. 29, 2001).
Pearson et al., *Protein Expression and Purification*, 17(1): 49-56 (Oct. 1999).
Rubinstein et al., *Nucleic Acids Research*, 21(11): 2613-2617 (Jun. 11, 1993).
"*Mus musculus* ES cells cDNA, Riken full-length enriched library, clone: 2410002E02, full insert sequence," Genbank accession No. AK010332-GI: 12845696 (Feb. 8, 2001).
Mummidi et al., *Journal of Biological Chemistry*, 275(25): 18946-18961 (Jun. 23, 2000).
Jüppner, *Bone*, 17(2 Suppl.): 39S-42S (Aug. 1995).
Bork et al., *Protein Science*, 2(1): 31-40 (Jan. 1993).
Blast 2 Sequences, Sequence 4 and SID15 (www.ncbi.nlm.nih.gov).
Blast 2 Sequences, sid31 and SID15 (www.ncbi.nlm.nih.gov).
Capon et al., *Nature*, 302 (5903): 33-37 (1983).
Cheng et al., *Cell*, 95 (6): 793-803 (1998).
Cohen et al., *Nature*, 334 (6178): 119-124 (1988).

(Continued)

*Primary Examiner* — Stephen Kapushoc
(74) *Attorney, Agent, or Firm* — Leydig, Voit & Mayer, Ltd.

(57) ABSTRACT

The present invention relates to a probe for selecting ES cells, which characteristically contains one of DNAs having base sequences depicted in SEQ ID Nos; 1, 2, 3, 4, 5, 6, 7 and 8, or DNAs having base sequences depicted in SEQ ID Nos; 9, 11, 13, 15, 17, 19, 21, 23 and 41 and a screening method of ES cell using this probe. Preparation of a probe for selecting ES cells becomes feasible by identifying plural gene with ES cell-specific expressions (ECAT genes) and using the information of the base sequences of these gene groups. Efficient selection of ES cell enables supply of a large amount of ES cell expected to be applicable to regenerative medicine.

10 Claims, 2 Drawing Sheets

OTHER PUBLICATIONS

European Patent Office, Extended European Search Report in European Patent Application No. 10010750 (Jun. 10, 2011).
Seeburg et al., *Nature*, 312 (5989): 71-75 (1984).
Takahashi et al., *Nature*, 423: 541-545 (2003).
Alberts et al., "Studying Gene Expression and Function" in *Molecular Biology of the Cell*, 4th edition, Garland Science, New York (2002), p. 545.
Hasty et al., *Mol. Cell. Biol.*, 11(11): 5586-5591 (1991).

\* cited by examiner

Expression pattern of ECAT (Northern Blotting)

1:ES cell, 2:ES cell differentiation-induced with retinoic acid, 3:orchis, 4:lung, 5:heart, 6:liver, 7:stomach, 8:kidney, 9:brain, 10:spleen, 11:thymus, 12:small intestine, 13:skin, 14:skeletal muscle Expression pattern of hECAT (Northern Blotting)

1:ES cell (simian, undifferentiated), 2:ES cell (simian, differentiated), 3:mesenchymal stem cell, 4:brain, 5:heart, 6:kidney, 7:orchis, 8:spleen, 9:liver, 10:muscle, 11:lung, 12:stomach, 13:placenta, 14:small intestine, 15:large intestine, 16:ovary

GENES WITH ES CELL-SPECIFIC EXPRESSION

CROSS-REFERENCE TO RELATED APPLICATION

This patent application is a divisional of U.S. patent application Ser. No. 10/479,334, filed Dec. 1, 2003 now U.S. Pat. No. 7,250,255, which is the U.S. national phase of International Patent Application No. PCT/JP2002/05350, filed May 31, 2002.

TECHNICAL FIELD

The present invention relates to an ECAT gene (ES cell associated transcript gene) specifically expressed in ES cells (embryonic stem cells) and use thereof.

BACKGROUND ART

Embryonic stem (ES) cell is a cell isolated from early embryo of mammal, which semipermanently continues to proliferate, while maintaining an ability to differentiate into any cell in the body, i.e., pluripotency. ES cell was first established in mouse in 1981, and brought an epoch-making technique of gene function analysis using knock out mice. Ever since the establishment of human ES cell was reported in 1998, application thereof to regenerative medicine has been highly expected. It is an attempt to achieve functional recovery by transplanting heart muscle cells or nerve cells differentiated from ES cells into patients with heart infarction and neurodegenerative diseases.

While the cell transplant therapy has been already employed, as typically seen in marrow graft in leukemia, it is associated with two problems of securing sufficient supply of cells to be transplanted and suppression of rejection reaction. Use of the ES cell that divides semipermanently altogether solves the problem of secured supply of sufficient amount of cell. When combined with the somatic cell clone technology, moreover, the rejection reaction can be also overcome. When an ES cell is established from a clone embryo prepared from the somatic cell of a patient and used for transplantation, rejection cannot occur since it has the same gene as does the patient. Therefore, ES cell has the potential to simultaneously solve the two problems in the cell transplant therapy.

While ES cell has the high potential as described above, human ES cell is difficult to establish and maintain as compared to mouse ES cell. Therefore, the development of a reliable establishment technique and a culture technique is necessary. For a human ES cell to be established, moreover, an embryo needs to be sacrificed. When it is combined with the somatic cell clone technology, it easily leads to human cloning. To solve such ethical issues, therefore, the development of a technique to directly produce an ES-like cell having pluripotency from a somatic cell is desired, which does not go through an embryo.

What plays a key role in the development of these techniques is a gene (ES cell associated transcript gene, hereinafter ECAT gene), which is specifically expressed in pluripotent cells such as ES cell and the like. The ECAT gene becomes a marker to determine if the cell is an ES cell. In addition, ES cell can be efficiently selected from a mixed culture of various kinds of cells by combining a control region of ECAT gene that induces ES cell specific expression and a drug resistance gene (JP-T-9-500004; corresponding U.S. Pat. No. 6,146,888). Furthermore, it may be possible to promote conversion of somatic cell to ES-like cell by inducing expression of ECAT gene.

The only one gene reported heretofore as an ECAT gene is transcription factor Oct3 (also called Oct4, POU5f1, hereinafter to be referred to as Oct-3/4) gene. While a similar gene has been reported with regard to human (hereinafter to be referred to as hoct-3/4 gene: Takeda et al., Nucleic Acids Res. 20: 4613-4620, 1992, SEQ ID No; 39), no report has been so far found on verified ES cell specific expression of hOct-3/4 gene. Oct-3/4 is a transcription factor that is specifically expressed in an ES cell and EG cell (embryonic germ cells), whose expression disappears along with the cell differentiation. Therefore, it is used as a marker of ES cell, and efficient establishment of ES cell has been attempted by knocking-in a neomycin resistance gene into its gene locus (JP-T-9-500004; corresponding to U.S. Pat. No. 6,146,888). However, a report has also documented that Oct-3/4 is expressed in trophectoderm cell as well, besides pluripotent cells (Biol Reprod 63: 1698-1705, 2000). Thus, use of Oct-3/4 gene alone as an index results in the selection of cells other than ES cells. To avoid this risk, it is desirable to identify plural ECAT genes and use them in combination.

Even if expression of Oct-3/4 alone in somatic cell is induced, conversion to ES-like cell is not observed. Even if Oct-3/4 is constantly expressed, differentiation of ES cell (differentiation into primitive-endoderm, primitive ectoderm) associated with withdrawal of LIF (leukemia inhibitor factor) cannot be suppressed. To the contrary, an interesting report has been made that, by increasing the expression amount of Oct-3/4 by only about 1.5 times the general level, differentiation similar to that associated with the withdrawal of LIF is induced (Experimental Medicine, 19, 330-338, 2001). As described above, the action of Oct-3/4 is not simple and induction thereof into ES cell by the expression of Oct-3/4 alone in somatic cell is difficult. From this aspect, too, it is considered necessary to combine plural ECAT genes and analyze ES cell.

Nevertheless, ECAT gene other than Oct-3/4 gene has not been found and there is a strong demand for the provision of a new ECAT gene, from the aspects of regenerative medicine and application of ES cells to cell transplantation.

DISCLOSURE OF THE INVENTION

The present invention aims at provision of a novel ECAT gene. More particularly, the present invention aims at provision of a screening method of ES cell using the new ECAT gene and a gene product peptide encoded thereby, as well as a probe for selecting an ES cell.

To identify ECAT candidate genes, the present inventors used the EST (Expressed Sequence Tag) data base (detail to be described later) for computer analysis and identified candidate genes to reach 10 genes. Of the 10 genes, 8 genes were subjected to Northern blotting, whereby expression in ES cell and 12 kinds of organs (mouse) was analyzed. As a result, the expression of all the 8 genes was found to be specific to ES cells. It was also found that the expression of these genes quickly disappeared after stimulation of ES cell with retinoic acid, namely, by induction of differentiation. From the above results, the present inventors have found that these 8 genes are ECAT genes, which resulted in the completion of the present invention. Of the remaining two genes, one gene was analyzed by Northern blotting and the like to find the gene to be an ECAT gene.

Further, they have identified a human gene homologous to the ECAT gene (hereinafter hECAT) and analyzed expression in the ES cell and 13 kinds of organs (human).

Accordingly, the present invention provides the following.

(1) A probe for selecting ES cells, comprising a DNA which has a base sequence depicted in any one of SEQ ID Nos; 1, 3, 4, 5, 6, 7 and 8.

(2) A probe for selecting ES cells, comprising a DNA which hybridizes to a DNA having a base sequence depicted in any one of SEQ ID Nos; 1, 3, 4, 5, 6, 7 and 8 under stringent conditions, and which encodes a protein specifically expressed in an ES cell.

(3) A probe for selecting ES cells, comprising a DNA which has a base sequence depicted in SEQ ID No; 1, 3, 4, 5, 6, 7 or 8, wherein one to several bases are deleted, substituted or added, and which is capable of hybridizing, under stringent conditions, to a DNA encoding a protein specifically expressed in an ES cell.

(4) A probe for selecting ES cells, comprising a DNA which has a base sequence depicted in any one of SEQ ID Nos; 9, 13, 15, 17, 19, 21, 23 and 41.

(5) The probe of the above-mentioned (4), comprising a DNA which has a base sequence depicted in any one of SEQ ID Nos; 9, 13, 15, 17, 19, 21 and 23.

(6) A probe for selecting ES cells, comprising a DNA which hybridizes to a DNA having a base sequence depicted in any one of SEQ ID Nos; 9, 13, 15, 17, 19, 21, 23 and 41 under stringent conditions, and which encodes a protein specifically expressed in an ES cell.

(7) The probe of the above-mentioned (6), comprising a DNA which hybridizes to a DNA which has a base sequence depicted in any one of SEQ ID Nos; 9, 13, 15, 17, 19, 21 and 23 under stringent conditions, and which encodes a protein specifically expressed in an ES cell.

(8) A probe for selecting ES cells, comprising a DNA which has a base sequence depicted in SEQ ID No; 9, 13, 15, 17, 19, 21, 23 or 41, wherein one to several bases are deleted, substituted or added, and which is capable of hybridizing, under stringent conditions, to a DNA encoding a protein specifically expressed in an ES cell.

(9) The probe of the above-mentioned (8), comprising a DNA which has a base sequence depicted in SEQ ID No; 9, 13, 15, 17, 19, 21 or 23, wherein one to several bases are deleted, substituted or added, and which is capable of hybridizing, under stringent conditions, to a DNA encoding a protein specifically expressed in an ES cell.

(10) The probe of any of the above-mentioned (1) to (9), which is used for selecting a mouse ES cell.

(11) A probe for selecting ES cells, comprising a DNA which has a base sequence depicted in any one of SEQ ID Nos; 27, 29, 31, 33, 35, 37 and 43.

(12) The probe of the above-mentioned (11), which comprises a DNA which has a base sequence depicted in any one of SEQ ID Nos; 27, 29, 31, 33, 35 and 37.

(13) A probe for selecting ES cells, comprising a DNA which hybridizes to a DNA which has a base sequence depicted in any one of SEQ ID Nos; 27, 29, 31, 33, 35, 37 and 43 under stringent conditions, and which encodes a protein specifically expressed in an ES cell.

(14) The probe of the above-mentioned (13), which comprises a DNA which hybridizes to a DNA which has a base sequence depicted in any one of SEQ ID Nos; 27, 29, 31, 33, 35 and 37 under stringent conditions, and which encodes a protein specifically expressed in an ES cell.

(15) A probe for selecting ES cells, comprising a DNA which has a base sequence depicted in SEQ ID No; 27, 29, 31, 33, 35, 37 or 43, wherein one to several bases are deleted, substituted or added, and which is capable of hybridizing, under stringent conditions, to a DNA encoding a protein specifically expressed in an ES cell.

(16) The probe of the above-mentioned (15), comprising a DNA which has a base sequence depicted in SEQ ID No; 27, 29, 31, 33, 35 or 37, wherein one to several bases are deleted, substituted or added, and which is capable of hybridizing, under stringent conditions, to a DNA encoding a protein specifically expressed in an ES cell.

(17) The probe of any of the above-mentioned (11) to (16), which is used for selecting a human ES cell.

(18) A gene comprising a DNA of any of the following (a)-(c):
(a) a DNA comprising a base sequence depicted in SEQ ID No; 17
(b) a DNA which hybridizes to a DNA having a base sequence of (a) under stringent conditions, which encodes a protein specifically expressed in an ES cell
(c) a DNA which has a base sequence of (a), wherein one to several bases are deleted, substituted or added, and which is capable of hybridizing, under stringent conditions, to a DNA encoding a protein specifically expressed in an ES cell.

(19) A protein of the following (a) or (b):
(a) a protein having an amino acid sequence depicted in SEQ ID No; 18
(b) a protein which has an amino acid sequence of (a), wherein one to several bases are deleted, substituted or added, and which is specifically expressed in an ES cell.

(20) A gene comprising a DNA of any of the following (a)-(c):
(a) a DNA comprising a base sequence depicted in SEQ ID No; 29
(b) a DNA which hybridizes to a DNA having a base sequence of (a) under stringent conditions, and which encodes a protein specifically expressed in an ES cell
(c) a DNA which has a base sequence of (a), wherein one to several bases are deleted, substituted or added, and which is capable of hybridizing, under stringent conditions, to a DNA encoding a protein specifically expressed in an ES cell.

(21) A protein of the following (a) or (b):
(a) a protein having an amino acid sequence depicted in SEQ ID No; 30
(b) a protein which has an amino acid sequence of (a), wherein one to several bases are deleted, substituted or added, and which is specifically expressed in an ES cell.

(22) A gene comprising a DNA of any of the following (a)-(c):
(a) a DNA comprising a base sequence depicted in SEQ ID No; 33
(b) a DNA which hybridizes to a DNA having a base sequence of (a) under stringent conditions, and which encodes a protein specifically expressed in an ES cell
(c) a DNA which has a base sequence of (a), wherein one to several bases are deleted, substituted or added, and which is capable of hybridizing, under stringent conditions, to a DNA encoding a protein specifically expressed in an ES cell.

(23) A protein of the following (a) or (b):
(a) a protein having an amino acid sequence depicted in SEQ ID No; 34
(b) a protein which has an amino acid sequence of (a), wherein one to several bases are deleted, substituted or added, and which is specifically expressed in an ES cell.

(24) A gene comprising a DNA of any of the following (a)-(c):
(a) a DNA comprising a base sequence depicted in SEQ ID No; 37
(b) a DNA which hybridizes to a DNA having a base sequence of (a) under stringent conditions, and which encodes a protein specifically expressed in an ES cell
(c) a DNA which has a base sequence of (a), wherein one to several bases are deleted, substituted or added, and which is capable of hybridizing, under stringent conditions, to a DNA encoding a protein specifically expressed in an ES cell.

(25) A protein of the following (a) or (b):
(a) a protein having an amino acid sequence depicted in SEQ ID No; 38
(b) a protein which has an amino acid sequence of (a), wherein one to several bases are deleted, substituted or added, and which is specifically expressed in an ES cell.
(26) A method of screening an ES cell, which comprises analyzing an intracellular expression state of a DNA having a base sequence depicted in SEQ ID No; 9, 13, 15, 17, 19, 21, 23 or 41, or a protein having an amino acid sequence depicted in SEQ ID No; 10, 14, 16, 18, 20, 22, 24 or 42.
(27) The method of the above-mentioned (26), wherein the intracellular expression state of a DNA having a base sequence depicted in SEQ ID No; 9, 13, 15, 17, 19, 21 or 23, or a protein having an amino acid sequence depicted in SEQ ID No; 10, 14, 16, 18, 20, 22 or 24 is analyzed.
(28) The method of the above-mentioned (26) or (27), which further comprises analyzing an intracellular expression state of a DNA having a base sequence depicted in SEQ ID No; 11, or a protein having an amino acid sequence depicted in SEQ ID No; 12.
(29) The method of any of the above-mentioned (26) to (28), which further comprises analyzing an intracellular expression state of a DNA having a base sequence depicted in SEQ ID No; 25, or a protein having an amino acid sequence depicted in SEQ ID No; 26.
(30) A method of screening an ES cell, which comprises analyzing an intracellular expression state of a DNA having a base sequence depicted in SEQ ID No; 27, 29, 31, 33, 35, 37 or 43, or a protein having an amino acid sequence depicted in SEQ ID No; 28, 30, 32, 34, 36, 38 or 44.
(31) The method of the above-mentioned (30), wherein the intracellular expression state of a DNA having a base sequence depicted in SEQ ID No; 27, 29, 31, 33, 35 or 37, or a protein having an amino acid sequence depicted in SEQ ID No; 28, 30, 32, 34, 36 or 38 is analyzed.
(32) The method of the above-mentioned (30) or (31), which further comprises analyzing an intracellular expression state of a DNA having a base sequence depicted in SEQ ID No; 39, or a protein having an amino acid sequence depicted in SEQ ID No; 40.
(33) A probe for selecting ES cells, comprising a DNA which has a non-repetitive sequence comprising not less than 20 continuous bases from a base sequence depicted in SEQ ID No; 9, 11, 13, 15, 17, 19, 21, 23 or 41, or SEQ ID No; 27, 29, 31, 33, 35, 37 or 43, and which has a sequence specific to a gene specifically expressed in an ES cell.
(34) A method of screening an ES cell, which comprises analyzing an expression state of a gene specifically expressed in an ES cell, using a probe of any of the above-mentioned (1)-(17) and (33).
(35) The method of the above-mentioned (34), which further comprises using a probe for selecting ES cells comprising a DNA having a base sequence depicted in SEQ ID No; 2 or 11.
(36) The method of the above-mentioned (34) or (35), which further comprises using an ES cell selection probe comprising a DNA having a base sequence depicted in SEQ ID No; 25.
(37) The method of the above-mentioned (34), which further comprises using an ES cell selection probe comprising a DNA having a base sequence depicted in SEQ ID No; 27.
(38) The method of the above-mentioned (34) or (35), which further comprises using an ES cell selection probe comprising a DNA having a base sequence depicted in SEQ ID No; 39.

The present invention further relates to a recombinant vector having a DNA encoding a gene specifically expressed in an ES cell or a protein specifically expressed in an ES cell, particularly, a vector for forced expression of a differentiation inhibiting gene (pluripotency sustaining gene), and a transformant cell transformed with said vector.

The present invention moreover relates to a recombinant vector comprising a selection gene such as a drug resistance gene or the like, which is incorporated into a genomic DNA fragment containing a DNA encoding a gene specifically expressed in an ES cell or a protein specifically expressed in an ES cell, particularly a vector for selecting ES cell, and a transformant cell transformed with said vector.

DETAILED DESCRIPTION OF THE INVENTION

Figure 1:
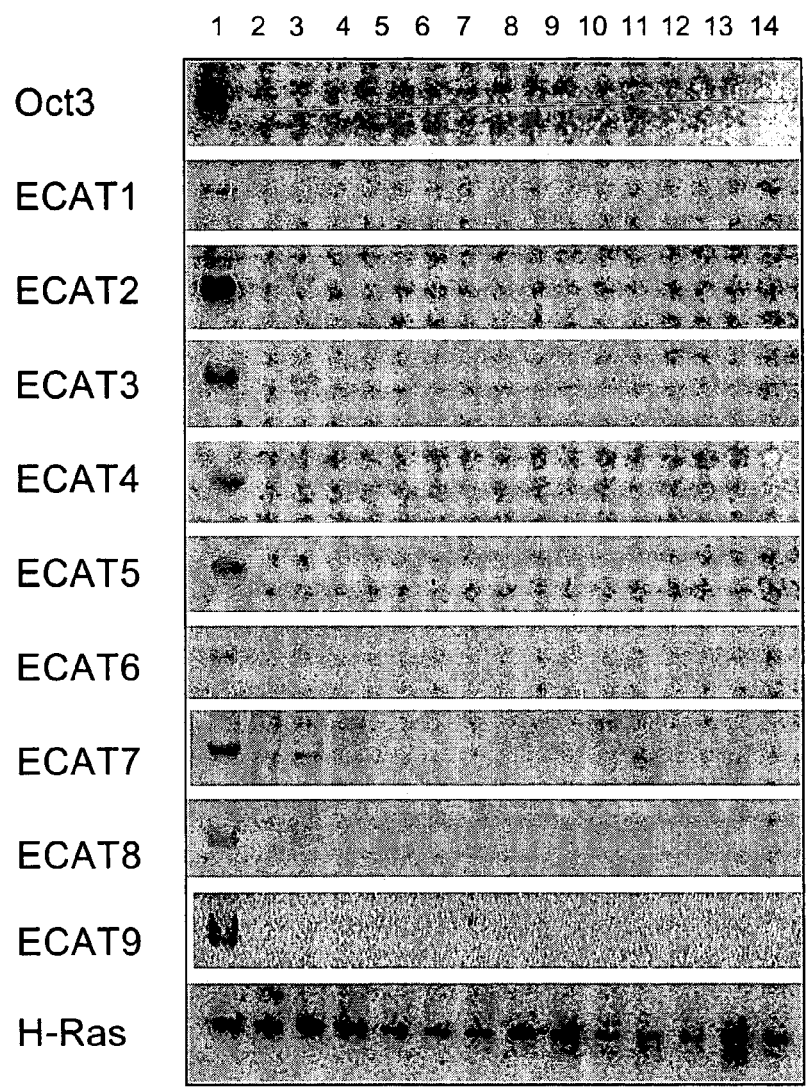
FIG. 1 shows an analysis of the expression of each ECAT gene in an ES cell and 12 kinds of organs in adult mouse by Northern blotting.

The present invention relates to a gene specifically expressed in an ES cell (hereinafter to be also referred to as gene with ES cell-specific expression), namely, ECAT gene. It is possible to determine if a cell is an ES cell with the presence of expression of ECAT gene as an index. The present invention provides an ES cell selection probe preferable for deciding on the ES cell as described. As this probe, a polynucleotide containing a DNA comprising a base sequence depicted in any one of SEQ ID Nos; 1-8, a DNA comprising a base sequence depicted in SEQ ID No; 9 (hereinafter ECAT1 gene), a DNA comprising a base sequence depicted in SEQ ID No; 11 (hereinafter ECAT2 gene), a DNA comprising a base sequence depicted in SEQ ID No; 13 (hereinafter ECAT3 gene), a DNA comprising a base sequence depicted in SEQ ID No; 15 (hereinafter ECAT4 gene), a DNA comprising a base sequence depicted in SEQ ID No; 17 (hereinafter ECAT5 gene), a DNA comprising a base sequence depicted in SEQ ID No; 19 (hereinafter ECAT6 gene), a DNA comprising a base sequence depicted in SEQ ID No; 21 (hereinafter ECAT7 gene), a DNA comprising a base sequence depicted in SEQ ID No; 23 (hereinafter ECAT8 gene) or a DNA comprising a base sequence depicted in SEQ ID No; 41 (hereinafter ECAT9 gene) can be specifically mentioned. In the present invention, moreover, the ES cell selection probe may be any as long as it can achieve the object of confirmation of the presence or otherwise of the expression of ECAT gene, and may be the above-mentioned base sequence which underwent modification by substitution, deletion, addition and the like. Specifically, a polynucleotide comprising a DNA that hybridizes to an ECAT gene under stringent conditions and encodes a protein specifically expressed in an ES cell, and a polynucleotide comprising a DNA which has a base sequence of an ECAT gene, wherein one to several bases are deleted, substituted or added, and which is capable of hybridizing, under stringent conditions, to a DNA encoding a protein specifically expressed in an ES cell, can be preferably used as a probe for selecting ES cells in the present invention. Specific examples include a polynucleotide containing a DNA comprising a base sequence depicted in SEQ ID No; 27 (hereinafter hECAT2 gene), a DNA comprising a base sequence depicted in SEQ ID No; 29 (hereinafter hECAT3 gene), a DNA comprising a base sequence depicted in SEQ ID No; 31 (hereinafter hECAT4 gene), a DNA comprising a base sequence depicted in SEQ ID No; 33 (hereinafter hECAT5 gene), a DNA comprising a base sequence depicted in SEQ ID No; 35 (hereinafter hECAT7 gene), a DNA comprising a base sequence depicted in SEQ ID No; 37 (hereinafter hECAT8 gene) or a DNA comprising a base sequence depicted in SEQ ID No; 43 (hereinafter hECAT9 gene).

In addition, a polynucleotide containing a DNA comprising a base sequence depicted in SEQ ID No; 25, i.e., a DNA encoding Oct-3/4, or a DNA comprising a base sequence depicted in SEQ ID No; 39, i.e., a DNA encoding hOct-3/4 can be also used as an ES cell selection probe. Because a report has documented that the Oct-3/4 gene is expressed even in trophectoderm cells as mentioned above, concurrent use of a polynucleotide preferably containing an ECAT gene other than Oct-3/4 gene or hOct-3/4 gene and the like, such as the novel ES cell selection probe of the present invention is preferable. Even in the case of a novel ES cell selection probe containing the above-mentioned ECAT gene, concurrent use of several kinds of probes is preferable to more accurately determine if it is an ES cell.

In the present specification, the term "stringent conditions" means the conditions under which a DNA having about 70% or more, preferably about 80% or more, particularly preferably about 90% or more, homology in a base sequence can hybridize, wherein stringency can be controlled by appropriately changing the temperature, salt concentration and the like during hybridizing reaction and washing. More preferable conditions are those under which a DNA having about not less than 95% homology can hybridize.

ECAT2 gene is reported as a gene pH34 that shows a decreased expression when EC cell is stimulated with retinoic acid (Differentiation 46: 61-67, 1991), and according to the database of RIKEN, it is described as ESG (ES cell specific gene) 1. Furthermore, ECAT3 gene is a gene encoding a mouse protein having an F-box, whose expression in orchis and ovary is reported (Current Biology 9: 1180-1182, 1999). ECAT7 gene is reported as protein DNMT3L that is similar to DNMT3 that causes DNA methylation (Genomics 65: 293-298, 2000). ECAT9 gene is reported as a growth factor called GDF3, in Jones C M et al., Mol Endocrinol. 6: 1961-1968, 1992 for mouse and in Caricasole et al., Oncogene 16: 95-103, 1998 for human. There is no report on an ES cell specific expression. With regard to ECAT4 gene, ECAT5 gene and ECAT6 gene, no report is found in published literatures, but by a protein database search has revealed that ECAT4 gene has a homeo box, ECAT5 gene has homology with oncogene H-Ras, and that ECAT6 gene is similar to keratin. For ECAT5 gene, even though its partial sequence is known, a cDNA sequence per se and the amino acid sequence of a protein that the DNA sequence codes for have not been determined. Accordingly, the present invention provides an ECAT5 gene, an ECAT5 protein, a gene having extremely high homology with these and a protein showing similar behavior with these.

As used herein, the "gene having extremely high homology" specifically means a gene that hybridizes to ECAT5 gene under stringent conditions, and as long as this requirement is satisfied, one to several bases may be deleted, substituted or added in the base sequence (SEQ ID No; 17) of ECAT5 gene. Specifically, it is a gene having about 70% or more, preferably about 80% or more, more preferably about 90% or more, particularly preferably 95% or more, homology with the ECAT5 gene. The "protein showing similar behavior" means a protein having the characteristics that the ECAT5 protein shows, namely, being specifically expressed in an ES cell. As long as this requirement is satisfied, one to several amino acids may be deleted, substituted or added in the amino acid sequence (SEQ ID No; 18) of ECAT5 protein.

Moreover, the ES cell selection probe of the present invention encompasses a DNA fragment consisting of a partial sequence comprising 20 or more continuous bases without a repeated sequence, from the base sequence described in SEQ ID No; 9, 11, 13, 15, 17, 19, 21, 23 or 41, or SEQ ID No; 27, 29, 31, 33, 35, 37 or 43, which are constructed based on the sequences of various ECAT genes and hECAT genes. The DNA fragment is not particularly limited as long as it can hybridize to ECAT gene or hECAT gene. Specifically, it is a DNA containing a continuous partial sequence generally comprising 20 bases or more, preferably about 100 bases or more, and more preferably about 200 bases or more, of the base sequence of each SEQ ID No, which contains at least a sequence specific to various ECAT genes or hECAT genes intended for detection, and which does not consist of a repeated sequence alone. Preferable examples thereof include a DNA fragment depicted in SEQ ID Nos; 1-8.

Of the aforementioned 9 kinds of mouse ECAT genes, 7 kinds of ECAT2 gene, ECAT3 gene, ECAT4 gene, ECAT5 gene, ECAT7 gene, ECAT8 gene and ECAT9 gene have been found to have the corresponding human ECAT genes (mentioned below: hECAT2 gene, hECAT3 gene, hECAT4 gene, hECAT5 gene, hECAT7 gene, hECAT8 gene and hECAT9 gene, respectively). Of these, the base sequences of hECAT3, hECAT5 and hECAT8 genes and the amino acid sequences of the proteins encoded by the base sequences have not been determined. Accordingly, the present invention provides the genes and proteins of hECAT3, hECAT5 and hECAT8, as well as genes having extremely high homology therewith and proteins showing similar behaviors.

Here, the "genes having extremely high homology" and the "proteins showing similar behaviors" specifically mean genes that hybridize to the genes of hECAT3, hECAT5 or hECAT8 under stringent conditions. As long as this requirement is satisfied, one to several bases may be deleted, substituted or added in the base sequences of hECAT3, hECAT5 and hECAT8 genes (SEQ ID No; 29, SEQ ID No; 33 and SEQ ID No; 37, respectively). To be precise, it is a gene having about 70% or more, preferably about 80% or more, more preferably about 90% or more, particularly preferably 95% or more, homology with those genes. The "proteins showing similar behaviors" mean proteins having the characteristics of the hECAT3 protein, hECAT5 protein or hECAT8 protein. As long as this requirement is satisfied, one to several amino acids may be deleted, substituted or added in the amino acid sequences of hECAT3 protein, hECAT5 protein and hECAT8 protein (SEQ ID No; 30, SEQ ID No; 34 and SEQ ID No; 38, respectively).

The probe of the present invention can be prepared according to the methods known in this field. For example, this probe can be prepared as a DNA isolated by cleaving EST of the corresponding ECAT gene with a restriction enzyme, a DNA obtained by amplification of PCR using, as a template, genomic DNA, complementary DNA (cDNA) prepared from ES cell-derived mRNA, chemically synthesized DNA, and a DNA constructed by a suitable combination of these methods.

The present invention provides a screening method of ES cell, which is characterized by analyzing the expression state of a gene specifically expressed in an ES cell. As used herein, the "gene specifically expressed in an ES cell" is the same as the aforementioned ECAT gene or hECAT gene, and is specifically exemplified by ECAT1 gene, ECAT2 gene, ECAT3 gene, ECAT4 gene, ECAT5 gene, ECAT6 gene, ECAT7 gene, ECAT8 gene, ECAT9 gene, hECAT2 gene, hECAT3 gene, hECAT4 gene, hECAT5 gene, hECAT7 gene, hECAT8 gene and hECAT9 gene, as well as Oct-3/4gene, hOct-3/4 gene and the like.

In the present invention, ES cell is screened by analyzing the expression state of a gene specifically expressed in ES cells or a protein specifically expressed in ES cells and encoded by said gene. For the analysis of expression state at the gene level, the aforementioned probe for selecting ES cells can be used. It is also preferable to concurrently use a probe comprising a polynucleotide having a DNA encoding Oct-3/4, as mentioned above. Such probe may be labeled with a fluorescent substance, an enzyme, a radioisotope or the like. For the analysis of the expression state at the protein level, a substance having specific affinity for the above-mentioned protein specifically expressed in ES cells, such as an antibody, is used to examine intracellular expression of the protein. More specifically, methods utilizing an antigen-antibody reaction generally practiced in the pertinent field, such as immunoblot, immunoprecipitation and the like, are used. The antibody here is not particularly limited as long as it can specifically bind to the protein, and may be any of a polyclonal antibody, a monoclonal antibody and a functional fragment thereof. These antibodies and fragments thereof may be labeled with a fluorescent substance, an enzyme, a radioisotope or the like.

Moreover, they may be commercially available ones or may be prepared appropriately according to a conventional method.

The present invention relates to an expression vector comprising any of the above-mentioned gene specifically expressed in ES cells and a gene encoding a protein specifically expressed in ES cells. As used herein, the gene specifically expressed in ES cells is as defined above, and the gene encoding a protein specifically expressed in ES cells is specifically a gene encoding ECAT1 (SEQ ID No; 10), a gene encoding ECAT2 (SEQ ID No; 12) or hECAT2 (SEQ ID No; 28), a gene encoding ECAT3 (SEQ ID No; 14) or hECAT3 (SEQ ID No; 30), a gene encoding ECAT4 (SEQ ID No; 16) or hECAT4 (SEQ ID No; 32), a gene encoding ECAT5 (SEQ ID No; 18) or hECAT5 (SEQ ID No; 34), a gene encoding ECAT6 (SEQ ID No; 20), a gene encoding ECAT7 (SEQ ID No; 22) or hECAT7 (SEQ ID No; 36), a gene encoding ECAT8 (SEQ ID No; 24) or hECAT8 (SEQ ID No; 38) and a gene encoding ECAT9 (SEQ ID No; 42) or hECAT9 (SEQ ID No; 44) can be mentioned. The expression vector preferably has a function of suppressing the differentiation by expression of the vector in the cell, particularly ES cells, in light of the nature of the gene contained in the vector. In other words, it is a vector that forcibly expresses a differentiation inhibiting gene (pluripotency sustaining gene) (hereinafter to be also referred to as vector for forced expression of the differentiation inhibiting gene (pluripotency sustaining gene)). The expression vector of the present invention is not particularly limited as long as it is capable of maintaining replicability or autonomous growth in various animal cells and expressing the gene specifically expressed in ES cells, and encompasses virus vector, plasmid vector and the like. This expression vector can be prepared based on conventional genetic engineering, for example, according to basic textbooks such as Molecular cloning 2nd Ed., Cold Spring Harbor Laboratory Press (1989) and the like. The vector is preferably a virus vector, which is prepared by incorporating gene specifically expressed in ES cells or the like into DNA virus or RNA virus such as retrovirus, adenovirus, adeno-associated virus, herpesvirus, vaccinia virus, poxvirus, poliovirus, sindbis virus or the like. Where necessary, a desired promoter region, a drug resistance gene region or an expression regulatory region can be also introduced.

The expression vector of the present invention is introduced into a cell according to conventionally known methods such as transfection, lipofection, microinjection, gene gun, electroporation or the like.

Whether or not the expression vector of the present invention thus prepared is incorporated into a host cell and expressed can be confirmed by, for example, determining the amount of protein (polypeptide) that the introduced ECAT gene expressed and produced by, for example, ELISA and the like.

In addition to the use of the ECAT gene as a probe to determine if a cell is an ES cell, the ECAT gene can be also used for selective separation of ES cells from a mixture of ES cells and other kinds of cells. The present inventors have prepared a targeting vector to knock-in a drug selection gene into a protein translation region of each ECAT gene and, using is this vector, established ES cells that caused homologous recombination. Specifically, the technique described in JP-T-9-500004 (corresponding to U.S. Pat. No. 6,146,888) was applied. For example, a cell wherein a neomycin resistance gene had been knocked-in into an ECAT3 gene, ECAT4 gene or ECAT5 gene was cultured in the presence of G418, but cell differentiation was not observed in a selected cell. Such results suggest a possible use of the ECAT gene for the selective separation of ES cells. For an ensured selection of ES cells alone, it is preferable to perform homologous recombination using plural kinds of vectors incorporating different ECAT genes.

EXAMPLES

The present invention is explained in detail by referring to Examples, which are not to be construed as limitative.

Example 1

Identification of Mouse ECAT Gene (1) Identification of Candidate Gene by Computer Analysis (Procedure)

The EST database was used to identify the candidate genes of ECAT. EST is obtained by randomly extracting a number of cDNA clones from cDNA libraries derived from various cells and organs, analyzing only one reaction of the 5' or 3' end sequence thereof and registering same in a public database. ESTs can be said to be a catalog of genes expressed in each cell and each organ. More than one million clones derived from mouse and more than 30000 clones derived from mouse ES cell have been registered.

As the EST database, Unigene was used. Unigene is prepared by clustering clones of EST, which are considered to be derived from the same gene, and as of Mar. 5, 2001, 79917 sets have been reported for the mouse EST database, where each set consists of at least one EST or known gene.

As a method of analysis, Digital differential display method was used. This method is used to examine the frequency of presence of each set in the libraries of designated cells and organs, namely, the number of EST clones contained in each set is divided by the number of entire EST registrations derived from the library thereof, thereby to examine the frequency of expression between different cells and between different organs.

The frequency of gene expression in the libraries derived from the following 5 kinds of cells and an organ was analyzed by the Digital differential display method. The number in the parenthesis for each group is the number of analyzed clones. For Group 1 to Group 5, all the corresponding libraries were analyzed. Since the data of Group 6 contained enormous quantity, 23 libraries extracted while including organs and cells of the entire body as many kinds as possible were analyzed.

Group 1 fertilized eggs from 1-cell stage to blastocyst (49050 clones)
Group 2 ES cell or Embryonic carcinoma cells (32277 clones)
Group 3 fetus up to 8.5 days after fertilization (46728 clones)
Group 4 fetus after 9 days from fertilization (128882 clones)
Group 5 orchis (65685 clones)
Group 6 other cells, tissues (272460 clones)

As regards the set expected to specifically express in fertilized eggs and pluripotent cells, such as ES cell and the like, by the Digital differential display method, the mouse-derived EST database was searched using BlastN to examine if EST was present only in the pluripotent cell-derived libraries.

The database and analysis program had the following URLs. Unigene Mouse Sequence Collection
http://www.ncbi.nlm.nih.gov/Unigene/Mm.Home.html
Digital differential display
http://www.ncbi.nlm.nih.gov/Unigene/info_ddd.shtml
Blast Search
http://www.ncbi.nlm.nih.gov/BLAST/
(Results)

As a result of the analysis by the Digital differential display method and EST database search using BlastN, 10 genes were identified. ESTs of these genes were highly frequently present in fertilized eggs and ES cells but were not found in other cells and tissues of Group 6. While EST was included in the fetus- and orchis-derived libraries for some genes, since this was highly likely derived from primordial germ cell or sperm mother cell, which is a pluripotent cell, they were included in the candidates for ECAT gene. While Oct-3/4 gene was present at high frequency in the fertilized eggs and ES cell, it was also contained in other cells and organs, though small in number. Of the candidates, mouse-derived EST database was searched for 8 genes using BlastN, the results of which are shown in Table 1 (ECAT1-8).

Of the remaining two genes, one gene (ECAT9) was analyzed in the same manner. The results are shown in Table 1.

TABLE 1

| | EST | | | | | |
|---|---|---|---|---|---|---|
| ECATs | eggs Group 1 | ES (EC) Group 2 | -E8.5 Group 3 | E9- Group 4 | testis Group 5 | others Group 6 |
| Oct3/4 | 10 | 13 | 4 | 1 | 0 | 2 |
| 1 | 7 | 24 | 0 | 0 | 0 | 0 |
| 2 | 32 | 18 | 0 | 0 | 0 | 0 |
| 3 | 37 | 13 | 0 | 0 | 0 | 0 |
| 4 | 2 | 14 | 1 | 1 | 3 | 0 |
| 5 | 0 | 11 | 0 | 0 | 0 | 0 |
| 6 | 0 | 7 | 0 | 0 | 0 | 0 |
| 7 | 4 | 9 | 0 | 0 | 1 | 2 |
| 8 | 0 | 7 | 0 | 0 | 2 | 0 |
| 9 | 4 | 11 | 0 | 0 | 0 | 2 |

(2) Northern Blotting Analysis
(Procedure)

The candidate genes identified by computer analysis were analyzed for actual ES cell specific expression by Northern blotting. Using Trizol (manufactured by Lifetech Oriental Co. Ltd.), total RNA was extracted from undifferentiated ES cells and ES cells differentiation-induced with retinoic acids for 5 days. RNAs derived from various organs of adult mice were purchased from Sawady Technology Co., Ltd. The total RNA (5 μg) was separated by formalin agarose gel, transferred to a nylon membrane and fixed with UV closslink. When EST of an object gene was available for purchase, this DNA was used as a probe. When EST was not available, a DNA fragment specific for each ECAT was amplified by PCR and used as a probe. To be specific, using the following probes, the expression of Oct-3/4, ECAT1, ECAT2, ECAT3, ECAT4, ECAT5, ECAT6, ECAT7 and ECAT8 was examined. In addition, the expression of ECAT9 was also examined.

Oct-3/4: a DNA fragment containing a sequence depicted in SEQ ID No; 25, which was prepared by cleaving plasmid C1 in BS KS (Cell 60: 461-472, 1990) with EcoRI.

ECAT1: a DNA fragment containing a sequence depicted in SEQ ID No; 1, which was prepared by cleaving Mm.31054EST (#AI467128) with SalI/NotI.

ECAT2: a DNA fragment containing a sequence depicted in SEQ ID No; 2, which was prepared by cleaving pH34EST (#AA473366) with SalI/NotI.

ECAT3: a DNA fragment containing a sequence depicted in SEQ ID No; 3, which was prepared by cleaving FBX15EST (#AA571680) with SalI/NotI.

ECAT4: a DNA fragment containing a sequence depicted in SEQ ID No; 4, which was prepared by cleaving the fragment with EcoRI from a plasmid obtained by amplifying a homeobox coding region for gateway by PCR and TA cloning the same.

ECAT5: a DNA fragment containing a sequence depicted in SEQ ID No; 5, which was prepared by cleaving the fragment with EcoRI from a plasmid obtained by RT-PCR of E-RasS118/RACE11 and TA cloning.

ECAT6: a DNA fragment containing a sequence depicted in SEQ ID No; 6, which is a keratin-E PCR product (48927S/48927AS).

ECAT7: a DNA fragment containing a sequence depicted in SEQ ID No; 7, which was prepared by cleaving out from DNMT3LEST clone (AA895770, pBSSK-dnmt31) with EcoRI/XhoI.

ECAT8: a DNA fragment containing a sequence depicted in SEQ ID No; 8, which was prepared by cleaving Mm.77010RACE product from TA cloned plasmid with EcoRI.

ECAT9: a DNA fragment containing a sequence depicted in SEQ ID No; 41, which was prepared by reference to GDF3 (Jones CM. et al., mentioned above).

Probes were labeled with $^{32}$P-dCTP using a Mega prime DNA labeling system manufactured by Amersham Pharmacia. Hybridization was performed using Quickhyb of Funakoshi Co., Ltd. Signals after washing were analyzed using BAS5000 of Fuji Photo Film Co., Ltd.
(Results)

Of the 10 genes identified by the computer search, 9 genes were so far subjected to Northern blotting, and the expression in ES cell and 12 kinds of organs was analyzed. To be precise, the expression of each ECAT gene in ES cell and 12 kinds of organs of adult mouse was each analyzed by Northern blotting, the results of which are shown in FIG. 1.

It was found that every expression relating to 9 genes was specific to ES cell. While expression was somewhat observed in orchis, it was considered to have been derived from sperm mother cell. It was also found that the expression of these genes disappear quickly when ES cell was induced with retinoic acid stimulation. From these results, the 9 genes were considered to be ECAT genes.

(3) Analysis of ECAT Gene when ECAT gene is an unknown gene, the full length cDNA was identified according to RACE (Rapid Amplification of cDNA Ends) method using 5′RACE system, version 2 of Lifetech Oriental Co. Ltd. The RIKEN database of mouse full length cDNA was searched at URL (http://genome.gsc.riken.go.jp/).

Example 2

Analysis of Known Information of the Obtained ECAT gene (1) Blast Search

EST sequence of 8 genes confirmed to be ECAT genes as a result of Northern blotting was searched using Blast. As a result, the sequences of 3 genes were already reported in papers. ECAT2 gene was reported as gene pH34 that shows a decrease in expression when EC cell is stimulated with retinoic acid. ECAT4 gene was reported as a mouse protein having F box, whose expression is observed only in orchis and ovary. ECAT7 gene was reported as protein DNMT3L similar to DNMT3 that performs DNA methylation. Identification of full length cDNA was tried by the RACE method and translation region was identified for ECAT4 gene, ECAT5 gene and ECAT6 gene. Deducible amino acid sequence was searched using BlastP and it was found that ECAT4 gene has homeobox, ECAT5 gene has homology with cancer gene H-Ras, and ECAT6 gene is similar to keratin. In addition, ECAT9 gene, which was newly confirmed to be ECAT gene, was found to be a growth factor called GDF3.

(2) Search Through Riken Mouse cDNA Database

The mouse full length cDNA database published from in February 2001 by RIKEN was searched. As a result, full length cDNAs of 8 genes except ECAT5 gene were found to have been published. ECAT5 gene was not included in the database. In addition, ECAT2 gene is described as an ES cell specific gene (ESG) 1 in the RIKEN database, but no information was available as regards the expression of other 8 genes in ES cell.

Example 3

Identification of Human ECAT Gene (1) Blast Search of Human Genomic DNA Database and Human Protein Database As a result of Blast search, ECAT2-5, 7, 8 genes were found to have ortholog having an amino acid sequence identical in not less than 50%. For ECAT9 gene, too, hECAT9 gene exists as hGDF3 (Caricasole et al., mentioned above). As regards ECAT1 gene and ECAT6 gene, human ortholog could not be identified.

As a result of BlastP search, there was no publication of base sequence or amino acid sequence including hypothetical protein, for 3 genes of hECAT3 gene, hECAT5 gene and hECAT8 gene.

Example 4

Confirmation of Expression of Human Homologous Gene

The ES cell specific expression of ECAT gene in primates was confirmed.

Figure 2:
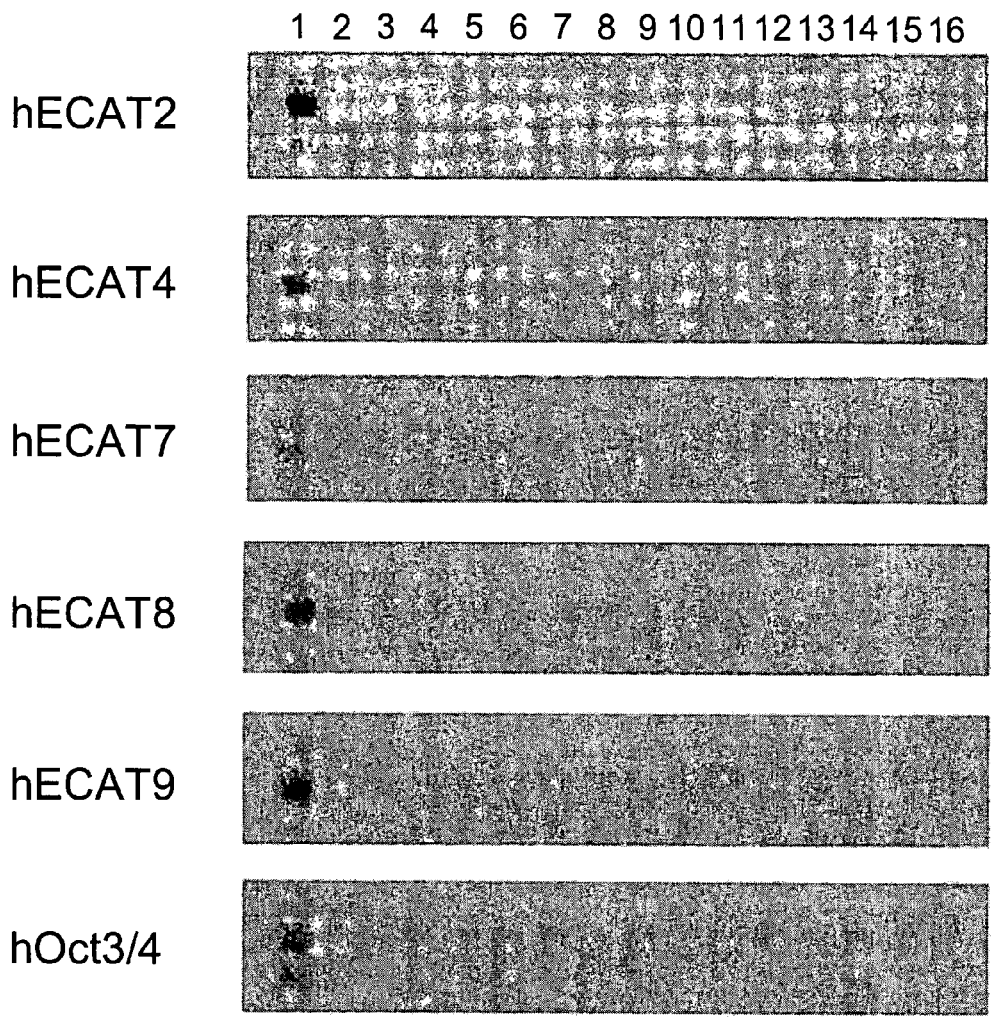
FIG. 2 shows an analysis of the expression of each ECAT gene in an ES cell, a mesenchymal stem cell and 13 kinds of organs in adult human by Northern blotting.

Respective total RNAs derived from 13 kinds of organs of adult human (purchased from Sawady Technology Co., Ltd. or Funakoshi Co., Ltd.), total RNA derived from human mesenchymal stem cell (purchased from Takara), and total RNA derived from simian ES cell (undifferentiated and differentiation induced with retinoic acid, provided by Professor Nakatsuji of the Institute For Frontier Medical Sciences) were analyzed by the Northern blotting method. The full length cDNA of EST clone corresponding to hECAT2,4,7,8,9 and hOct3/4 was used as a probe. While hybridization was performed in the same manner as in the analysis of mouse ECAT in the above-mentioned Example 1, the temperature of reaction and washing was set lower (50° C.) so that simian RNA could be detected using the human probe. As a result, every gene showed a strong signal in undifferentiated ES cell (FIG. 2). Along with the differentiation of the ES cell, signal was dramatically attenuated. While a smear thin signal was observed in other organs (cells), this is considered to be a nonspecific one caused by the lowered temperature of reaction and washing. From the foregoing results, it has been confirmed that ECAT genes selectively express in ES cells of not only mouse but of primates, as marker genes thereof.

INDUSTRIAL APPLICABILITY

According to the present invention, 9 kinds of ECAT genes specifically expressed in mouse ES cell can be newly provided. In addition, human ECAT genes corresponding to 7 kinds out of these 9 kinds can be provided. Moreover, selective cell markers of ES cell can be obtained by combining these ECAT genes or fragments thereof. Furthermore, the present invention is more effective for a method for selecting ES cell based on a combination with drug resistance gene, in an attempt to introduce somatic cell into ES cell-like cell and the like than the single use of Oct-3/4 gene or a fragment thereof, and is considered to be useful in the actual application of a regenerative therapy and the like.

This application is based on a patent application No. 2001-165927 filed in Japan, the contents of which are hereby incorporated by reference.

The invention claimed is:

1. An isolated probe for selecting mouse embryonic stem (ES) cells, said probe comprising a DNA which has a non-repetitive sequence comprising not less than 100 continuous bases of SEQ ID NO: 17, and which has a sequence specific to a gene specifically expressed in a mouse ES cell.

2. A vector comprising (a) fragments of SEQ ID NO: 17, wherein the fragments have regions necessary for homologous recombination, and (b) a selection gene knocked-in to the protein translation region of the mouse gene.

3. The vector of claim 2, wherein the selection gene is a drug resistance gene.

4. A cell transformed with the vector of claim 2.

5. A cell transformed with the vector of claim 3.

6. An isolated nucleic acid comprising
   (a) a DNA comprising SEQ ID NO: 17, or
   (b) a DNA encoding the amino acid sequence of SEQ ID NO: 18.

7. A vector comprising the nucleic acid of claim 6.

8. A cell comprising the vector of claim 7.

9. A process for producing a recombinant protein, comprising (a) culturing the cell of claim 8 under conditions sufficient for the nucleic acid to produce a recombinant protein, and (b) recovering the protein.

10. An isolated probe for selecting mouse embryonic stem (ES) cells, said probe comprising the nucleic acid of claim 6, wherein the nucleic acid comprises SEQ ID NO: 17.

* * * * *

SEQUENCE LISTING

```
<160> NUMBER OF SEQ ID NOS: 44

<210> SEQ ID NO 1
<211> LENGTH: 836
<212> TYPE: DNA
<213> ORGANISM: Mus musculus

<400> SEQUENCE: 1
gcgaggctgc caccggccg gctcccggga aggtccgcaa ggcggccacc cagccggctc    60
```

-continued

```
cggtgcaggt tgccaggag gccacccagt tggctcccgt gaaggtccgc gaggcggcca      120
cccagccggc ttccgggaag gtccgcgagg cggccaccca gttggctcct gtgaaggtcc      180
gcaaggcagc cacccagttg gctcctgtga aggtccacga ggcggccacc cagccggctc      240
cggggaaggt cagcgatgct gccacgcagt cggcttcggt gcaggttcgt gaggctgcca      300
cgcagctgtc tcccgtggag gccactgata ctagccagtt ggctcaggtg aaggctgatg      360
aagcctttgc ccagcacact tcaggggagg cccaccaggt tgccaatggg cagtctccca      420
ttgaagtctg tgagactgcc accgggcagc attctctaga tgtctctagg gccttgtccc      480
agaagtgtcc tgaggttttt gagtgggaga cccagagttg tttggatggc agctatgtca      540
tagttcagcc tccaagggat gcctgggaat catttatcat attataaatg catctctggt      600
gtgagccagg atagatggta cacgtctgca aatccagaac ctaaaggcag gggttagctt      660
gggctgagta aggcaatgat cttaaacctc agcctgccta agactccctt catctttctt      720
tctggttttt gccctaggaa tcgggaagaa cagagtagag ctgttttgt ttccccattg      780 tgttaaatgt ttgcagacac aatttaaagt attctaataa aaaaaaatt gcattc         836
```

<210> SEQ ID NO 2
<211> LENGTH: 591
<212> TYPE: DNA
<213> ORGANISM: Mus musculus

<400> SEQUENCE: 2

```
gccgtgcgtg gtggataagc ttgatctcgt cttccctgaa gtctggttcc ttggcaggat       60
gatggtgacc ctcgtgaccc gtaaagatat cccccgtgg gtgaaagttc ctgaagacct      120
gaaagatcca gaagtattcc aggtccagtc gctggtgctg aaatatctgt ttggcccaca      180
gggatctcga atgtctcaca tcgagcaggt gagccaggcc atgtttgagc tgaagaacct      240
ggaatctccc gaagaactta tcgaggtctt catttacggc tctcaaaaca caagattcg      300 ggctaaatgg atgcttcagt ccatggctga gaggtaccac ctgcgccagc aaaaaggagt      360
gctgaagctg gaggaatcca tgaagaccct ggagctaggc cagtgtatcg agtgaagcca      420
gtttccagtc cttgtgtctc cgacctggat gcaggttaag ctgtggccag tgtttggttc      480
tggcgggatt tttagctttg ttacatccta gcaagatatt ctggatccct gctgcgcatt      540
ctgatgtgaa tcccaaggtt accactctaa ataaaaaata aaattgaagt g              591
```

<210> SEQ ID NO 3
<211> LENGTH: 1667
<212> TYPE: DNA
<213> ORGANISM: Mus musculus

<400> SEQUENCE: 3

```
acttgcctgt ccaagatctg ttggaatctg cttctacaga agaccagctg aaacaaatag       60
cttcgtggga ctgagcacaa ctactagatt cttggacttc cgttcacagc tgccaattgt      120
tgggagtaca ataatggagg agtcggaatt ggagatttt agaagtaagt tgttagagg       180 ctcatctgtc acgaagcagc atgcctggcg aaaccagcac agcgagaagc gttgctcttc      240
ctccatcagt tctatatccc tggacagaat gccatcggaa atcttggtga agatactttc      300
ttacttggat gcggtgacct tggtgtgcat tggatgtgtg agcagacgct tttatcattt      360
ggctgatgac aatcttattt gggtcaggaa gtacgcagct gcatttagat caaaaagatc      420
acgttggaaa gctacttcag tggaggaaac agccacaagt ctgagcttgc tgtcagtttg      480
ggataaagaa gatggatact ggaagaaaga atatattaca aagcagatct catctgtgag      540
```

```
agcagccctc accaacagcc tcagtcctgt caaacgccgc acaagccttc cttcgaaaac    600
caaagagtcc ctcagaatat ctggcttagg ttggacaatc atcttaagag aagccagtgg    660
caaagaacac atcatgcagc attcgaatct ttccgtaaat gacaactctg tcactgtttt    720
ttggcatgac aaaaattggc cacatgtaga cacgttgtcc accctggatt tgtatggtgc    780
cacaccaatt tttatggagc agtataaagg ccctaacaca agttgtccac gatggctgtc    840
tttaattgaa aagtacgatc tgagtaattt acgcaagtct gctatgattg ctgcgacag    900
acatgttcgg gtattctgtg taaatcctgg cctcctggtg gggctgtggc aggagaatgg    960
tggactagct tttgtcatgg caaatattca ttcccatggc cttttcgaga aagcataat    1020
gggctcagac actattccct atacattgcc tcccgacact catttgtgg ataactaccc    1080
agactcaatg acctttatg gagataaagg ctttcagctg catatcgaca ttcatggcag    1140
taagacttac ttcctgtgta gcaccttcca caatctcttc tgcaggagag cgggcattaa    1200
caatggatat gtgaagttct tgatgataaa cttaaaaaat aacagagaac acctacctct    1260
tgttggaaaa gttggccttg aatggagaac tgactgttta aatggccgta ttgagagttg    1320
cattgtagtg gatatgacct tgctggatga ggacaagaag cccatctggt atgtgagttc    1380
tccagtgtgc ttgagatctg cctgccttcc tgatttcccg cagccggctt actctttcga    1440
gtacatggac agcgtaggag gagtgtgcgc agacctaggg tggtttgaaa ataccgatga    1500
atacttcatt gtcagactgg acatttacct cagtgtagca aaattacaac aatggtttgg    1560
gaggcaataa atgctgagtt agcagtaggg agtcttgtta ttagtaagct gtttgttttt    1620
tacaactttg tttttattga agttaaaat aaagcatatt tgtggta          1667

<210> SEQ ID NO 4
<211> LENGTH: 930
<212> TYPE: DNA
<213> ORGANISM: Mus musculus

<400> SEQUENCE: 4
ctgacatgag tgtgggtctt cctggtcccc acagtttgcc tagttctgag gaagcatcga     60
attctgggaa cgcctcatca atgcctgcag ttttcatcc cgagaactat tcttgcttac    120
aagggtctgc tactgagatg ctctgcacag aggctgcctc tcctcgccct tcctctgaag    180
acctgcctct tcaaggcagc cctgattctt ctaccagtcc caaacaaaag ctctcaagtc    240
ctgaggctga caagggccct gaggaggagg agaacaaggt ccttgccagg aagcagaaga    300
tgcggactgt gttctctcag gcccagctgt gtgcactcaa ggacaggttt cagaagcaga    360
agtacctcag cctccagcag atgcaagaac tctcctccat tctgaacctg agctataagc    420
aggttaagac ctggtttcaa aaccaaaggg tgaagtgcaa gcggtggcag aaaaaccagt    480
ggttgaagac tagcaatggt ctgattcaga agggctcagc accagtggag tatcccagca    540
tccattgcag ctatccccag ggctatctgg tgaacgcatc tggaagcctt tccatgtggg    600
gcagccagac ttggaccaac ccaacttgga gcagccagac ctggaccaac ccaacttgga    660
acaaccagac ctggaccaac ccaacttgga gcagccaggc ctggaccgct cagtcctgga    720
acggccagcc ttgaatgct gctccgctcc ataacttcgg ggaggacttt ctgcagcctt    780
acgtacagtt gcagcaaaac ttctctgcca gtgatttgga ggtgaatttg gaagccacta    840
gggaaagcca tgcgcatttt agcaccccac aagccttgga attattcctg aactactctg    900
tgactccacc aggtgaaata tgagacttac                                    930

<210> SEQ ID NO 5
```

<211> LENGTH: 845
<212> TYPE: DNA
<213> ORGANISM: Mus musculus

<400> SEQUENCE: 5

| | | | | | |
|---|---|---|---|---|---|
| actgcccctc | atcagactgc | tactcctggg | agcacagcac | ctgctcttta | cacctcttcc | 60 |
| ttgagctgct | ggggaatggc | tttgcctaca | aagtctagca | tcttggacct | gagctccggc | 120 |
| accccatgca | ccagatctcc | agaggaaagt | cacgaggctt | gggcacagtg | caaagatgct | 180 |
| ggcaggcagc | tacccgagta | caaggcagtg | gtggtgggtg | caagtggtgt | tggtaaaagt | 240 |
| gctctcacca | tccagatgac | tcaccaatgc | ttcgtgaaag | accatgaccc | cactatccaa | 300 |
| gattcctact | ggaaggaagt | ggccagggac | aacggaggct | acattctaaa | tgttctggat | 360 |
| acatctgggc | aggatattca | ccgggctctg | cgtgaccagt | gcttggcatc | tggtgatggt | 420 |
| gtgctgggcg | tctttgctct | tgacgacccc | tcgtctctgg | accagttgca | gcagatatgg | 480 |
| tccacctgga | cccctcacca | caagcagcct | ctggtactag | tgggcaacaa | gtgtgacctg | 540 |
| gtgaccactg | ctggagatgc | tcatgctgcc | gcagccctcc | ttgctcacaa | gttggggggcc | 600 |
| cccttggtga | agacctcagc | caagacgcgg | caaggtgtgg | aggaagcctt | tgccctgctt | 660 |
| gtccatgaga | ttcagagggc | ccaggaggct | gtggccgaat | caagcaagaa | gacccgacac | 720 |
| cagaaagccg | tgtgtagctg | tggctgctct | gtagcctgaa | gatctttgtc | tagcaaattg | 780 |
| acccttgtct | catgtcaagg | tgacaattct | cttgtaataa | gatctccctc | tccgaccaag | 840 |
| ttacc | | | | | | 845 |

<210> SEQ ID NO 6
<211> LENGTH: 166
<212> TYPE: DNA
<213> ORGANISM: Mus musculus

<400> SEQUENCE: 6

| | | | | | |
|---|---|---|---|---|---|
| actgaggccc | ctgtctgcgt | atgatagccc | aggcccagga | ccttaggctg | cagctccctg | 60 |
| catctactgc | caagcctgaa | ctcctatgag | ctagctgttg | ccttctgtgt | ttgctttgtg | 120 |
| ctgcccctta | cagagaggcc | ccttgggttg | accccagaaa | ttgcta | | 166 |

<210> SEQ ID NO 7
<211> LENGTH: 1521
<212> TYPE: DNA
<213> ORGANISM: Mus musculus

<400> SEQUENCE: 7

| | | | | | |
|---|---|---|---|---|---|
| ggagacacct | tcttcttgct | ctaagaccct | tgaaaccttg | gacctggaga | cttccgacag | 60 |
| ctctagccct | gatgctgaca | gtcctctgga | agagcaatgg | ctgaaatcct | ccccagccct | 120 |
| gaaggaggac | agtgtggatg | tggtactgga | agactgcaaa | gagcctctgt | cccctcctc | 180 |
| gcctccgaca | gcagagaga | tgatcaggta | cgaagtcaaa | gtgaaccgac | ggagcattga | 240 |
| agacatctgc | ctctgctgtg | gaactctcca | ggtgtacact | cggcacccct | tgtttgaggg | 300 |
| agggttatgt | gccccatgta | aggataagtt | cctggagtcc | ctcttcctgt | atgatgatga | 360 |
| tggacaccag | agttactgca | ccatctgctg | ttccgggggt | accctgttca | tctgtgagag | 420 |
| ccccgactgt | accagatgct | actgtttcga | gtgtgtggac | atcctggtgg | gccccgggac | 480 |
| ctcagagagg | atcaatgcca | tggcctgctg | ggtttgcttc | ctgtgcctgc | ccttctcacg | 540 |
| gagtggactg | ctgcagaggc | gcaagaggtg | gcggcaccag | ctgaaggcct | tccatgatca | 600 |
| agagggagcg | ggccctatgg | agatatacaa | gacagtgtct | gcatggaaga | gacagccagt | 660 |

```
gcgggtactg agccttttta gaaatattga taaagtacta agagtttggg cttttttgga      720
aagcggttct ggttctgggg gaggaacgct gaagtacgtg aagatgtca caaatgtcgt      780 gaggagagac gtggagaaat ggggcccctt tgacctggtg tacggctcga cgcagcccct    840
aggcagctct tgtgatcgct gtcccggctg gtacatgttc cagttccacc ggatcctgca    900
gtatgcgctg cctcgccagg agagtcagcg gcccttcttc tggatattca tggacaatct    960
gctgctgact gaggatgacc aagagacaac tacccgcttc cttcagacag aggctgtgac   1020
cctccaggat gtccgtggca gagactacca gaatgctatg cgggtgtgga gcaacattcc   1080
agggctgaag agcaagcatg cgcccctgac cccaaaggaa gaagagtatc tgcaagccca   1140
agtcagaagc aggagcaagc tggacgcccc gaaagttgac ctcctggtga gaactgcct    1200 tctcccgctg agagtact tcaagtattt ttctcaaaac tcacttcctc tttagaaatg      1260
aatcaccata agatgaaagt cttttcctaga accagggcag atttcttcct aaggtctctt   1320
ccctccacag tttttctctgg tttgctttca ggccttcggg tttctctcct gtttgattgc   1380
caggatgcct ctgtgcagct cactttgcgg ggtgggaggt gcctacggct ctgcacaagt   1440
tcccggtggg ataacctgcc atgtttctct gaaactgtgt gtacctgttg tgaagttttt   1500
caaatatatc ataggattgt t                                              1521

<210> SEQ ID NO 8
<211> LENGTH: 489
<212> TYPE: DNA
<213> ORGANISM: Mus musculus

<400> SEQUENCE: 8
atatatgctg atccagatgt tccatcagta agtgggtcta gccagaggcc gaatgagaag     60
ccactgcggt tgactgaaaa gaaagactgt gacgagaaga acggctgtgt aaaattactg   120
cagtttctaa atcctgatcc tttgagagct gatgggacct cagacctgca ccagttgcag   180
aaggtgaagc tgggcacact gcagcctggg gtggtgctcc ggaacaggat cgagccctgc    240
ctaaccctgg agaaatcacc tctgtcggca gacctgaaga aggtgaacat gttcttaaag    300
ccagactcct gacgacatgc cagccctttc caacacagag tgttgctttg ttttgctttg    360
tctgttctgt tctaagagtg acggggatga aatacagggc tttgcgcgtc ctgggcatgc   420
attcatcact gaaccatacc ccaattccat aggaggattt aaataaaca cttctaaggc    480 tacattgca                                                            489

<210> SEQ ID NO 9
<211> LENGTH: 1623
<212> TYPE: DNA
<213> ORGANISM: Mus musculus
<220> FEATURE:
<221> NAME/KEY: CDS
<222> LOCATION: (50)..(1369)

<400> SEQUENCE: 9
tgactgatct tgagtttgca taggcttcct gcggtgaaac gggtacact atg gcc tct     58
                                                    Met Ala Ser
                                                      1 ctg aag agg ttt cag acg ctc gtg ccc ctg gat cac aaa caa ggt acc     106
Leu Lys Arg Phe Gln Thr Leu Val Pro Leu Asp His Lys Gln Gly Thr
  5                  10                  15 tta ttt gaa att att gga gag ccc aag ttg ccc aag tgg ttc cat gtc    154
Leu Phe Glu Ile Ile Gly Glu Pro Lys Leu Pro Lys Trp Phe His Val
 20                  25                  30                  35 gaa tgc ctg gaa gat cca aaa aga ctg tac gtg gaa cct cgg cta ctg    202
```

| | | | | | | | | | | | | |
|---|---|---|---|---|---|---|---|---|---|---|---|---|
| Glu | Cys | Leu | Glu | Asp | Pro | Lys | Arg | Leu | Tyr | Val | Pro | Arg | Leu | Leu |
| | | | 40 | | | | | 45 | | | | | 50 | |

| gaa | atc | atg | ttt | ggt | aag | gat | gga | gag | cac | atc | cca | cat | ctt | gaa | tct | 250 |
|---|---|---|---|---|---|---|---|---|---|---|---|---|---|---|---|---|
| Glu | Ile | Met | Phe | Gly | Lys | Asp | Gly | Glu | His | Ile | Pro | His | Leu | Glu | Ser | |
| | | | 55 | | | | | 60 | | | | | 65 | | | |

| atg | ttg | cac | acc | ctg | ata | cat | gtg | aac | gtg | tgg | ggc | cct | gaa | agg | cga | 298 |
|---|---|---|---|---|---|---|---|---|---|---|---|---|---|---|---|---|
| Met | Leu | His | Thr | Leu | Ile | His | Val | Asn | Val | Trp | Gly | Pro | Glu | Arg | Arg | |
| | | 70 | | | | | 75 | | | | | 80 | | | | |

| gct | gag | att | tgg | ata | ttc | gga | ccg | ccg | cct | ttc | cga | agg | gac | gtt | gac | 346 |
|---|---|---|---|---|---|---|---|---|---|---|---|---|---|---|---|---|
| Ala | Glu | Ile | Trp | Ile | Phe | Gly | Pro | Pro | Pro | Phe | Arg | Arg | Asp | Val | Asp | |
| | 85 | | | | | 90 | | | | | 95 | | | | | |

| cgg | atg | ctc | act | gat | ctg | gct | cac | tat | tgc | cgc | atg | aaa | ctg | atg | gaa | 394 |
|---|---|---|---|---|---|---|---|---|---|---|---|---|---|---|---|---|
| Arg | Met | Leu | Thr | Asp | Leu | Ala | His | Tyr | Cys | Arg | Met | Lys | Leu | Met | Glu | |
| 100 | | | | | 105 | | | | | 110 | | | | | 115 | |

| ata | gag | gct | ctg | gag | gct | gga | gtt | gag | cgt | cgt | cgt | atg | gcg | gcc | cat | 442 |
|---|---|---|---|---|---|---|---|---|---|---|---|---|---|---|---|---|
| Ile | Glu | Ala | Leu | Glu | Ala | Gly | Val | Glu | Arg | Arg | Arg | Met | Ala | Ala | His | |
| | | | | 120 | | | | | 125 | | | | | 130 | | |

| aag | gct | gcc | acc | cag | cct | gct | ccc | gtg | aag | gtc | cgc | gag | gct | gcc | cct | 490 |
|---|---|---|---|---|---|---|---|---|---|---|---|---|---|---|---|---|
| Lys | Ala | Ala | Thr | Gln | Pro | Ala | Pro | Val | Lys | Val | Arg | Glu | Ala | Ala | Pro | |
| | | | 135 | | | | | 140 | | | | | 145 | | | |

| cgg | ccc | gct | tcc | gtg | aag | gtc | cct | gag | acg | gcc | acc | cag | cct | gct | ccc | 538 |
|---|---|---|---|---|---|---|---|---|---|---|---|---|---|---|---|---|
| Arg | Pro | Ala | Ser | Val | Lys | Val | Pro | Glu | Thr | Ala | Thr | Gln | Pro | Ala | Pro | |
| | | 150 | | | | | 155 | | | | | 160 | | | | |

| gtg | aag | gtc | cgc | gag | gct | gcc | cct | cag | ccc | gct | ccg | gtg | cag | gag | gtc | 586 |
|---|---|---|---|---|---|---|---|---|---|---|---|---|---|---|---|---|
| Val | Lys | Val | Arg | Glu | Ala | Ala | Pro | Gln | Pro | Ala | Pro | Val | Gln | Glu | Val | |
| | 165 | | | | | 170 | | | | | 175 | | | | | |

| cgc | gag | gct | gcc | cct | cag | cag | gct | tcc | gtg | cag | gag | gag | gtc | cgc | gag | 634 |
|---|---|---|---|---|---|---|---|---|---|---|---|---|---|---|---|---|
| Arg | Glu | Ala | Ala | Pro | Gln | Gln | Ala | Ser | Val | Gln | Glu | Glu | Val | Arg | Glu | |
| 180 | | | | | 185 | | | | | 190 | | | | | 195 | |

| gct | gcc | acc | gag | cag | gct | ccc | gtg | cag | gag | gtc | cgc | gag | gct | gcc | acc | 682 |
|---|---|---|---|---|---|---|---|---|---|---|---|---|---|---|---|---|
| Ala | Ala | Thr | Glu | Gln | Ala | Pro | Val | Gln | Glu | Val | Arg | Glu | Ala | Ala | Thr | |
| | | | | 200 | | | | | 205 | | | | | 210 | | |

| gag | cag | gct | ccc | gtg | cag | gag | gtc | agc | gag | gct | gcc | acc | gag | cag | gct | 730 |
|---|---|---|---|---|---|---|---|---|---|---|---|---|---|---|---|---|
| Glu | Gln | Ala | Pro | Val | Gln | Glu | Val | Ser | Glu | Ala | Ala | Thr | Glu | Gln | Ala | |
| | | | 215 | | | | | 220 | | | | | 225 | | | |

| ccc | gtg | cag | gag | gtc | aac | gag | gct | gcc | acc | gag | cag | gct | tcc | gtg | cag | 778 |
|---|---|---|---|---|---|---|---|---|---|---|---|---|---|---|---|---|
| Pro | Val | Gln | Glu | Val | Asn | Glu | Ala | Ala | Thr | Glu | Gln | Ala | Ser | Val | Gln | |
| | | 230 | | | | | 235 | | | | | 240 | | | | |

| gcg | gtc | cgc | gag | gct | gcc | acc | cgg | ccg | gct | ccc | ggg | aag | gtc | cgc | aag | 826 |
|---|---|---|---|---|---|---|---|---|---|---|---|---|---|---|---|---|
| Ala | Val | Arg | Glu | Ala | Ala | Thr | Arg | Pro | Ala | Pro | Gly | Lys | Val | Arg | Lys | |
| | 245 | | | | | 250 | | | | | 255 | | | | | |

| gcg | gcc | acc | cag | ccg | gct | ccg | gtg | cag | gtt | tgc | cag | gag | gcc | acc | cag | 874 |
|---|---|---|---|---|---|---|---|---|---|---|---|---|---|---|---|---|
| Ala | Ala | Thr | Gln | Pro | Ala | Pro | Val | Gln | Val | Cys | Gln | Glu | Ala | Thr | Gln | |
| 260 | | | | | 265 | | | | | 270 | | | | | 275 | |

| ttg | gct | ccc | gtg | aag | gtc | cgc | gag | gcg | gcc | acc | cag | ccg | gct | tcc | ggg | 922 |
|---|---|---|---|---|---|---|---|---|---|---|---|---|---|---|---|---|
| Leu | Ala | Pro | Val | Lys | Val | Arg | Glu | Ala | Ala | Thr | Gln | Pro | Ala | Ser | Gly | |
| | | | | 280 | | | | | 285 | | | | | 290 | | |

| aag | gtc | cgc | gag | gcg | gcc | acc | cag | ttg | gct | cct | gtg | aag | gtc | cgc | aag | 970 |
|---|---|---|---|---|---|---|---|---|---|---|---|---|---|---|---|---|
| Lys | Val | Arg | Glu | Ala | Ala | Thr | Gln | Leu | Ala | Pro | Val | Lys | Val | Arg | Lys | |
| | | | 295 | | | | | 300 | | | | | 305 | | | |

| gca | gcc | acc | cag | ttg | gct | cct | gtg | aag | gtc | cac | gag | gcg | gcc | acc | cag | 1018 |
|---|---|---|---|---|---|---|---|---|---|---|---|---|---|---|---|---|
| Ala | Ala | Thr | Gln | Leu | Ala | Pro | Val | Lys | Val | His | Glu | Ala | Ala | Thr | Gln | |
| | | 310 | | | | | 315 | | | | | 320 | | | | |

| ccg | gct | ccg | ggg | aag | gtc | agc | gat | gct | gcc | acg | cag | tcg | gct | tcg | gtg | 1066 |
|---|---|---|---|---|---|---|---|---|---|---|---|---|---|---|---|---|
| Pro | Ala | Pro | Gly | Lys | Val | Ser | Asp | Ala | Ala | Thr | Gln | Ser | Ala | Ser | Val | |
| | 325 | | | | | 330 | | | | | 335 | | | | | |

| cag | gtt | cgt | gag | gct | gcc | acg | cag | ctg | tct | ccc | gtg | gag | gcc | act | gat | 1114 |
|---|---|---|---|---|---|---|---|---|---|---|---|---|---|---|---|---|
| Gln | Val | Arg | Glu | Ala | Ala | Thr | Gln | Leu | Ser | Pro | Val | Glu | Ala | Thr | Asp | |
| 340 | | | | | 345 | | | | | 350 | | | | | 355 | |

| act | agc | cag | ttg | gct | cag | gtg | aag | gct | gat | gaa | gcc | ttt | gcc | cag | cac | 1162 |
|---|---|---|---|---|---|---|---|---|---|---|---|---|---|---|---|---|

```
        Thr Ser Gln Leu Ala Gln Val Lys Ala Asp Glu Ala Phe Ala Gln His
                        360                 365                 370 act tca ggg gag gcc cac cag gtt gcc aat ggg cag tct ccc att gaa          1210
Thr Ser Gly Glu Ala His Gln Val Ala Asn Gly Gln Ser Pro Ile Glu
            375                 380                 385 gtc tgt gag act gcc acc ggg cag cat tct cta gat gtc tct agg gcc          1258
Val Cys Glu Thr Ala Thr Gly Gln His Ser Leu Asp Val Ser Arg Ala
        390                 395                 400 ttg tcc cag aag tgt cct gag gtt ttt gag tgg gag acc cag agt tgt          1306
Leu Ser Gln Lys Cys Pro Glu Val Phe Glu Trp Glu Thr Gln Ser Cys
    405                 410                 415 ttg gat ggc agc tat gtc ata gtt cag cct cca agg gat gcc tgg gaa          1354
Leu Asp Gly Ser Tyr Val Ile Val Gln Pro Pro Arg Asp Ala Trp Glu
420                 425                 430                 435 tca ttt atc ata tta taaatgcatc tctggtgtga gccaggatag atggtacacg          1409
Ser Phe Ile Ile Leu
                440 tctgcaaatc agaacctaa aggcaggggt tagcttgggc tgagtaaggc aatgatctta         1469 aacctcagcc tgcctaagac tcccttcatc tttctttctg gttttttgccc taggaatcgg      1529 gaagaacaga gtagagctgt ttttgtttcc ccattgtgtt aaatgtttgc agacacaatt       1589 taaagtattc aataaaaaa aaaattgcat tccc                                     1623

<210> SEQ ID NO 10
<211> LENGTH: 440
<212> TYPE: PRT
<213> ORGANISM: Mus musculus

<400> SEQUENCE: 10

Met Ala Ser Leu Lys Arg Phe Gln Thr Leu Val Pro Leu Asp His Lys
1               5                   10                  15

Gln Gly Thr Leu Phe Glu Ile Ile Gly Glu Pro Lys Leu Pro Lys Trp
            20                  25                  30

Phe His Val Glu Cys Leu Glu Asp Pro Lys Arg Leu Tyr Val Glu Pro
        35                  40                  45

Arg Leu Leu Glu Ile Met Phe Gly Lys Asp Gly Glu His Ile Pro His
    50                  55                  60

Leu Glu Ser Met Leu His Thr Leu Ile His Val Asn Val Trp Gly Pro
65                  70                  75                  80

Glu Arg Arg Ala Glu Ile Trp Ile Phe Gly Pro Pro Phe Arg Arg
                85                  90                  95

Asp Val Asp Arg Met Leu Thr Asp Leu Ala His Tyr Cys Arg Met Lys
            100                 105                 110

Leu Met Glu Ile Glu Ala Leu Glu Ala Gly Val Glu Arg Arg Arg Met
        115                 120                 125

Ala Ala His Lys Ala Ala Thr Gln Pro Ala Pro Val Lys Val Arg Glu
    130                 135                 140

Ala Ala Pro Arg Pro Ala Ser Val Lys Val Pro Glu Thr Ala Thr Gln
145                 150                 155                 160

Pro Ala Pro Val Lys Val Arg Glu Ala Ala Pro Gln Pro Ala Pro Val
                165                 170                 175

Gln Glu Val Arg Glu Ala Ala Pro Gln Gln Ala Ser Val Gln Glu Glu
            180                 185                 190

Val Arg Glu Ala Ala Thr Glu Gln Ala Pro Val Gln Glu Val Arg Glu
        195                 200                 205

Ala Ala Thr Glu Gln Ala Pro Val Gln Glu Val Ser Glu Ala Ala Thr
    210                 215                 220
```

```
Glu Gln Ala Pro Val Gln Glu Val Asn Glu Ala Ala Thr Glu Gln Ala
225                 230                 235                 240

Ser Val Gln Ala Val Arg Glu Ala Ala Thr Arg Pro Ala Pro Gly Lys
            245                 250                 255

Val Arg Lys Ala Ala Thr Gln Pro Ala Pro Val Gln Val Cys Gln Glu
        260                 265                 270

Ala Thr Gln Leu Ala Pro Val Lys Val Arg Glu Ala Ala Thr Gln Pro
    275                 280                 285

Ala Ser Gly Lys Val Arg Glu Ala Ala Thr Gln Leu Ala Pro Val Lys
290                 295                 300

Val Arg Lys Ala Ala Thr Gln Leu Ala Pro Val Lys Val His Glu Ala
305                 310                 315                 320

Ala Thr Gln Pro Ala Pro Gly Lys Val Ser Asp Ala Ala Thr Gln Ser
            325                 330                 335

Ala Ser Val Gln Val Arg Glu Ala Ala Thr Gln Leu Ser Pro Val Glu
        340                 345                 350

Ala Thr Asp Thr Ser Gln Leu Ala Gln Val Lys Ala Asp Glu Ala Phe
    355                 360                 365

Ala Gln His Thr Ser Gly Glu Ala His Gln Val Ala Asn Gly Gln Ser
370                 375                 380

Pro Ile Glu Val Cys Glu Thr Ala Thr Gly Gln His Ser Leu Asp Val
385                 390                 395                 400

Ser Arg Ala Leu Ser Gln Lys Cys Pro Glu Val Phe Glu Trp Glu Thr
            405                 410                 415

Gln Ser Cys Leu Asp Gly Ser Tyr Val Ile Val Gln Pro Pro Arg Asp
        420                 425                 430

Ala Trp Glu Ser Phe Ile Ile Leu
    435                 440

<210> SEQ ID NO 11
<211> LENGTH: 591
<212> TYPE: DNA
<213> ORGANISM: Mus musculus
<220> FEATURE:
<221> NAME/KEY: CDS
<222> LOCATION: (59)..(412)

<400> SEQUENCE: 11
gccgtgcgtg gtggataagc ttgatctcgt cttccctgaa gtctggttcc ttggcagg         58 atg atg gtg acc ctc gtg acc cgt aaa gat atc ccc ccg tgg gtg aaa       106
Met Met Val Thr Leu Val Thr Arg Lys Asp Ile Pro Pro Trp Val Lys
1               5                   10                  15 gtt cct gaa gac ctg aaa gat cca gaa gta ttc cag gtc cag tcg ctg       154
Val Pro Glu Asp Leu Lys Asp Pro Glu Val Phe Gln Val Gln Ser Leu
            20                  25                  30 gtg ctg aaa tat ctg ttt ggc cca cag gga tct cga atg tct cac atc       202
Val Leu Lys Tyr Leu Phe Gly Pro Gln Gly Ser Arg Met Ser His Ile
        35                  40                  45 gag cag gtg agc cag gcc atg ttt gag ctg aag aac ctg gaa tct ccc       250
Glu Gln Val Ser Gln Ala Met Phe Glu Leu Lys Asn Leu Glu Ser Pro
    50                  55                  60 gaa gaa ctt atc gag gtc ttc att tac ggc tct caa aac aac aag att       298
Glu Glu Leu Ile Glu Val Phe Ile Tyr Gly Ser Gln Asn Asn Lys Ile
65                  70                  75                  80 cgg gct aaa tgg atg ctt cag tcc atg gct gag agg tac cac ctg cgc       346
Arg Ala Lys Trp Met Leu Gln Ser Met Ala Glu Arg Tyr His Leu Arg
                85                  90                  95
```

```
cag caa aaa gga gtg ctg aag ctg gag gaa tcc atg aag acc ctg gag      394
Gln Gln Lys Gly Val Leu Lys Leu Glu Glu Ser Met Lys Thr Leu Glu
            100                 105                 110 cta ggc cag tgt atc gag tgaagccagt ttccagtcct tgtgtctccg             442
Leu Gly Gln Cys Ile Glu
        115 acctggatgc aggttaagct gtggccagtg tttggttctg gcgggatttt tagctttgtt    502 acatcctagc aagatattct ggatccctgc tgcgcattct gatgtgaatc ccaaggttac    562 cactctaaat aaaaaataaa attgaagtg                                      591

<210> SEQ ID NO 12
<211> LENGTH: 118
<212> TYPE: PRT
<213> ORGANISM: Mus musculus

<400> SEQUENCE: 12

Met Met Val Thr Leu Val Thr Arg Lys Asp Ile Pro Pro Trp Val Lys
1               5                   10                  15

Val Pro Glu Asp Leu Lys Asp Pro Glu Val Phe Gln Val Gln Ser Leu
            20                  25                  30

Val Leu Lys Tyr Leu Phe Gly Pro Gln Gly Ser Arg Met Ser His Ile
        35                  40                  45

Glu Gln Val Ser Gln Ala Met Phe Glu Leu Lys Asn Leu Glu Ser Pro
    50                  55                  60

Glu Glu Leu Ile Glu Val Phe Ile Tyr Gly Ser Gln Asn Asn Lys Ile
65                  70                  75                  80

Arg Ala Lys Trp Met Leu Gln Ser Met Ala Glu Arg Tyr His Leu Arg
                85                  90                  95

Gln Gln Lys Gly Val Leu Lys Leu Glu Glu Ser Met Lys Thr Leu Glu
            100                 105                 110

Leu Gly Gln Cys Ile Glu
        115

<210> SEQ ID NO 13
<211> LENGTH: 1670
<212> TYPE: DNA
<213> ORGANISM: Mus musculus
<220> FEATURE:
<221> NAME/KEY: CDS
<222> LOCATION: (134)..(1567)

<400> SEQUENCE: 13
acttgcctgt ccaagatctg ttggaatctg cttctacaga agaccagctg aaacaaatag    60
cttcgtggga ctgagcacaa ctactagatt cttggacttc cgttcacagc tgccaattgt    120
tgggagtaca ata atg gag gag tcg gaa ttg gag att ttt aga agt aag      169
            Met Glu Glu Ser Glu Leu Glu Ile Phe Arg Ser Lys
            1               5                   10 ttt gtt aga ggc tca tct gtc acg aag cag cat gcc tgg cga aac cag     217
Phe Val Arg Gly Ser Ser Val Thr Lys Gln His Ala Trp Arg Asn Gln
            15                  20                  25 cac agc gag aag cgt tgc tct tcc tcc atc agt tct ata tcc ctg gac     265
His Ser Glu Lys Arg Cys Ser Ser Ser Ile Ser Ser Ile Ser Leu Asp
        30                  35                  40 aga atg cca tcg gaa atc ttg gtg aag ata ctt tct tac ttg gat gcg     313
Arg Met Pro Ser Glu Ile Leu Val Lys Ile Leu Ser Tyr Leu Asp Ala
45                  50                  55                  60 gtg acc ttg gtg tgc att gga tgt gtg agc aga cgc ttt tat cat ttg     361
Val Thr Leu Val Cys Ile Gly Cys Val Ser Arg Arg Phe Tyr His Leu
                65                  70                  75
```

```
gct gat gac aat ctt att tgg gtc agg aag tac gca gct gca ttt aga    409
Ala Asp Asp Asn Leu Ile Trp Val Arg Lys Tyr Ala Ala Ala Phe Arg
             80              85              90 tca aaa aga tca cgt tgg aaa gct act tca gtg gag gaa aca gcc aca    457
Ser Lys Arg Ser Arg Trp Lys Ala Thr Ser Val Glu Glu Thr Ala Thr
         95             100             105 agt ctg agc ttg ctg tca gtt tgg gat aaa gaa gat gga tac tgg aag    505
Ser Leu Ser Leu Leu Ser Val Trp Asp Lys Glu Asp Gly Tyr Trp Lys
    110             115             120 aaa gaa tat att aca aag cag atc tca tct gtg aga gca gcc ctc acc    553
Lys Glu Tyr Ile Thr Lys Gln Ile Ser Ser Val Arg Ala Ala Leu Thr
125             130             135             140 aac agc ctc agt cct gtc aaa cgc cgc aca agc ctt cct tcg aaa acc    601
Asn Ser Leu Ser Pro Val Lys Arg Arg Thr Ser Leu Pro Ser Lys Thr
            145             150             155 aaa gag tcc ctc aga ata tct ggc tta ggt tgg aca atc atc tta aga    649
Lys Glu Ser Leu Arg Ile Ser Gly Leu Gly Trp Thr Ile Ile Leu Arg
        160             165             170 gaa gcc agt ggc aaa gaa cac atc atg cag cat tcg aat ctt tcc gta    697
Glu Ala Ser Gly Lys Glu His Ile Met Gln His Ser Asn Leu Ser Val
    175             180             185 aat gac aac tct gtc act gtt ttt tgg cat gac aaa aat tgg cca cat    745
Asn Asp Asn Ser Val Thr Val Phe Trp His Asp Lys Asn Trp Pro His
    190             195             200 gta gac acg ttg tcc acc ctg gat ttg tat ggt gcc aca cca att ttt    793
Val Asp Thr Leu Ser Thr Leu Asp Leu Tyr Gly Ala Thr Pro Ile Phe
205             210             215             220 atg gag cag tat aaa ggc cct aac aca agt tgt cca cga tgg ctg tct    841
Met Glu Gln Tyr Lys Gly Pro Asn Thr Ser Cys Pro Arg Trp Leu Ser
            225             230             235 tta att gaa aag tac gat ctg agt aat tta cgc aag tct gct atg att    889
Leu Ile Glu Lys Tyr Asp Leu Ser Asn Leu Arg Lys Ser Ala Met Ile
        240             245             250 ggc tgc gac aga cat gtt cgg gta ttc tgt gta aat cct ggc ctc ctg    937
Gly Cys Asp Arg His Val Arg Val Phe Cys Val Asn Pro Gly Leu Leu
    255             260             265 gtg ggg ctg tgg cag gag aat ggt gga cta gct ttt gtc atg gca aat    985
Val Gly Leu Trp Gln Glu Asn Gly Gly Leu Ala Phe Val Met Ala Asn
    270             275             280 att cat tcc cat ggc ctt ttc gag aga agc ata atg ggc tca gac act   1033
Ile His Ser His Gly Leu Phe Glu Arg Ser Ile Met Gly Ser Asp Thr
285             290             295             300 att ccc tat aca ttg cct ccc gac act aca ttt gtg gat aac tac cca   1081
Ile Pro Tyr Thr Leu Pro Pro Asp Thr Thr Phe Val Asp Asn Tyr Pro
            305             310             315 gac tca atg acc ttt tat gga gat aaa ggc ttt cag ctg cat atc gac   1129
Asp Ser Met Thr Phe Tyr Gly Asp Lys Gly Phe Gln Leu His Ile Asp
        320             325             330 att cat ggc agt aag act tac ttc ctg tgt agc acc ttc cac aat ctc   1177
Ile His Gly Ser Lys Thr Tyr Phe Leu Cys Ser Thr Phe His Asn Leu
    335             340             345 ttc tgc agg aga gcg ggc att aac aat gga tat gtg aag ttc ttg atg   1225
Phe Cys Arg Arg Ala Gly Ile Asn Asn Gly Tyr Val Lys Phe Leu Met
    350             355             360 ata aac tta aaa aat aac aga gaa cac cta cct ctt gtt gga aaa gtt   1273
Ile Asn Leu Lys Asn Asn Arg Glu His Leu Pro Leu Val Gly Lys Val
365             370             375             380 ggc ctt gaa tgg aga act gac tgt tta aat ggc cgt att gag agt tgc   1321
Gly Leu Glu Trp Arg Thr Asp Cys Leu Asn Gly Arg Ile Glu Ser Cys
            385             390             395
```

```
att gta gtg gat atg acc ttg ctg gat gag gac aag aag ccc atc tgg    1369
Ile Val Val Asp Met Thr Leu Leu Asp Glu Asp Lys Lys Pro Ile Trp
        400                 405                 410 tat gtg agt tct cca gtg tgc ttg aga tct gcc tgc ctt cct gat ttc    1417
Tyr Val Ser Ser Pro Val Cys Leu Arg Ser Ala Cys Leu Pro Asp Phe
            415                 420                 425 ccg cag ccg gct tac tct ttc gag tac atg gac agc gta gga gga gtg    1465
Pro Gln Pro Ala Tyr Ser Phe Glu Tyr Met Asp Ser Val Gly Gly Val
        430                 435                 440 tgc gca gac cta ggg tgg ttt gaa aat acc gat gaa tac ttc att gtc    1513
Cys Ala Asp Leu Gly Trp Phe Glu Asn Thr Asp Glu Tyr Phe Ile Val
445                 450                 455                 460 aga ctg gac att tac ctc agt gta gca aaa tta caa caa tgg ttt ggg    1561
Arg Leu Asp Ile Tyr Leu Ser Val Ala Lys Leu Gln Gln Trp Phe Gly
                465                 470                 475 agg caa taaatgctga gttagcagta gggagtcttg ttattagtaa gctgtttgtt    1617
Arg Gln ttttacaact ttgtttttat tgaaagttaa aataaagcat atttgtggta ttc          1670

<210> SEQ ID NO 14
<211> LENGTH: 478
<212> TYPE: PRT
<213> ORGANISM: Mus musculus

<400> SEQUENCE: 14

Met Glu Glu Ser Glu Leu Glu Ile Phe Arg Ser Lys Phe Val Arg Gly
1               5                   10                  15

Ser Ser Val Thr Lys Gln His Ala Trp Arg Asn Gln His Ser Glu Lys
            20                  25                  30

Arg Cys Ser Ser Ile Ser Ser Ile Ser Leu Asp Arg Met Pro Ser
        35                  40                  45

Glu Ile Leu Val Lys Ile Leu Ser Tyr Leu Asp Ala Val Thr Leu Val
    50                  55                  60

Cys Ile Gly Cys Val Ser Arg Arg Phe Tyr His Leu Ala Asp Asp Asn
65                  70                  75                  80

Leu Ile Trp Val Arg Lys Tyr Ala Ala Ala Phe Arg Ser Lys Arg Ser
                85                  90                  95

Arg Trp Lys Ala Thr Ser Val Glu Glu Thr Ala Thr Ser Leu Ser Leu
            100                 105                 110

Leu Ser Val Trp Asp Lys Glu Asp Gly Tyr Trp Lys Lys Glu Tyr Ile
        115                 120                 125

Thr Lys Gln Ile Ser Ser Val Arg Ala Ala Leu Thr Asn Ser Leu Ser
    130                 135                 140

Pro Val Lys Arg Arg Thr Ser Leu Pro Ser Lys Thr Lys Glu Ser Leu
145                 150                 155                 160

Arg Ile Ser Gly Leu Gly Trp Thr Ile Ile Leu Arg Glu Ala Ser Gly
                165                 170                 175

Lys Glu His Ile Met Gln His Ser Asn Leu Ser Val Asn Asp Asn Ser
            180                 185                 190

Val Thr Val Phe Trp His Asp Lys Asn Trp Pro His Val Asp Thr Leu
        195                 200                 205

Ser Thr Leu Asp Leu Tyr Gly Ala Thr Pro Ile Phe Met Glu Gln Tyr
    210                 215                 220

Lys Gly Pro Asn Thr Ser Cys Pro Arg Trp Leu Ser Leu Ile Glu Lys
225                 230                 235                 240

Tyr Asp Leu Ser Asn Leu Arg Lys Ser Ala Met Ile Gly Cys Asp Arg
```

```
                    245                 250                 255
His Val Arg Val Phe Cys Val Asn Pro Gly Leu Leu Val Gly Leu Trp
                260                 265                 270

Gln Glu Asn Gly Gly Leu Ala Phe Val Met Ala Asn Ile His Ser His
            275                 280                 285

Gly Leu Phe Glu Arg Ser Ile Met Gly Ser Asp Thr Ile Pro Tyr Thr
        290                 295                 300

Leu Pro Pro Asp Thr Thr Phe Val Asp Asn Tyr Pro Asp Ser Met Thr
305                 310                 315                 320

Phe Tyr Gly Asp Lys Gly Phe Gln Leu His Ile Asp Ile His Gly Ser
                325                 330                 335

Lys Thr Tyr Phe Leu Cys Ser Thr Phe His Asn Leu Phe Cys Arg Arg
                340                 345                 350

Ala Gly Ile Asn Asn Gly Tyr Val Lys Phe Leu Met Ile Asn Leu Lys
                355                 360                 365

Asn Asn Arg Glu His Leu Pro Leu Val Gly Lys Val Gly Leu Glu Trp
            370                 375                 380

Arg Thr Asp Cys Leu Asn Gly Arg Ile Glu Ser Cys Ile Val Val Asp
385                 390                 395                 400

Met Thr Leu Leu Asp Glu Asp Lys Lys Pro Ile Trp Tyr Val Ser Ser
                405                 410                 415

Pro Val Cys Leu Arg Ser Ala Cys Leu Pro Asp Phe Pro Gln Pro Ala
                420                 425                 430

Tyr Ser Phe Glu Tyr Met Asp Ser Val Gly Gly Val Cys Ala Asp Leu
            435                 440                 445

Gly Trp Phe Glu Asn Thr Asp Glu Tyr Phe Ile Val Arg Leu Asp Ile
        450                 455                 460

Tyr Leu Ser Val Ala Lys Leu Gln Gln Trp Phe Gly Arg Gln
465                 470                 475

<210> SEQ ID NO 15
<211> LENGTH: 2184
<212> TYPE: DNA
<213> ORGANISM: Mus musculus
<220> FEATURE:
<221> NAME/KEY: CDS
<222> LOCATION: (190)..(1104)

<400> SEQUENCE: 15
agaaaggctg atttggttgg tgtcttgctc tttctgtggg aaggctgcgg ctcacttcct      60
tccgacttct tgataatttt gcattagaca tttaactctt cttctatga tctttccttc     120 tagacactga gttttttggt tgttgcctaa aaccttttca gaaatccctt ccctcgccat    180 cacactgac atg agt gtg ggt ctt cct ggt ccc cac agt ttg cct agt tct    231
           Met Ser Val Gly Leu Pro Gly Pro His Ser Leu Pro Ser Ser
             1               5                  10 gag gaa gca tcg aat tct ggg aac gcc tca tca atg cct gca gtt ttt    279
Glu Glu Ala Ser Asn Ser Gly Asn Ala Ser Ser Met Pro Ala Val Phe
 15                  20                  25                  30 cat ccc gag aac tat tct tgc tta caa ggg tct gct act gag atg ctc    327
His Pro Glu Asn Tyr Ser Cys Leu Gln Gly Ser Ala Thr Glu Met Leu
                 35                  40                  45 tgc aca gag gct gcc tct cct cgc cct tcc tct gaa gac ctg cct ctt    375
Cys Thr Glu Ala Ala Ser Pro Arg Pro Ser Ser Glu Asp Leu Pro Leu
             50                  55                  60 caa ggc agc cct gat tct tct acc agt ccc aaa caa aag ctc tca agt    423
Gln Gly Ser Pro Asp Ser Ser Thr Ser Pro Lys Gln Lys Leu Ser Ser
 65                  70                  75
```

| | | |
|---|---|---|
| cct gag gct gac aag ggc cct gag gag gag gag aac aag gtc ctt gcc<br>Pro Glu Ala Asp Lys Gly Pro Glu Glu Glu Glu Asn Lys Val Leu Ala<br>80                            85                          90 | | 471 |
| agg aag cag aag atg cgg act gtg ttc tct cag gcc cag ctg tgt gca<br>Arg Lys Gln Lys Met Arg Thr Val Phe Ser Gln Ala Gln Leu Cys Ala<br>95                          100                    105                  110 | | 519 |
| ctc aag gac agg ttt cag aag cag aag tac ctc agc ctc cag cag atg<br>Leu Lys Asp Arg Phe Gln Lys Gln Lys Tyr Leu Ser Leu Gln Gln Met<br>                115                    120                    125 | | 567 |
| caa gaa ctc tcc tcc att ctg aac ctg agc tat aag cag gtt aag acc<br>Gln Glu Leu Ser Ser Ile Leu Asn Leu Ser Tyr Lys Gln Val Lys Thr<br>              130                    135                    140 | | 615 |
| tgg ttt caa aac caa agg gtg aag tgc aag cgg tgg cag aaa aac cag<br>Trp Phe Gln Asn Gln Arg Val Lys Cys Lys Arg Trp Gln Lys Asn Gln<br>                145                    150                    155 | | 663 |
| tgg ttg aag act agc aat ggt ctg att cag aag ggc tca gca cca gtg<br>Trp Leu Lys Thr Ser Asn Gly Leu Ile Gln Lys Gly Ser Ala Pro Val<br>160                            165                    170 | | 711 |
| gag tat ccc agc atc cat tgc agc tat ccc cag ggc tat ctg gtg aac<br>Glu Tyr Pro Ser Ile His Cys Ser Tyr Pro Gln Gly Tyr Leu Val Asn<br>175                          180                    185                  190 | | 759 |
| gca tct gga agc ctt tcc atg tgg ggc agc cag act tgg acc aac cca<br>Ala Ser Gly Ser Leu Ser Met Trp Gly Ser Gln Thr Trp Thr Asn Pro<br>                195                    200                    205 | | 807 |
| act tgg agc agc cag acc tgg acc aac cca act tgg aac aac cag acc<br>Thr Trp Ser Ser Gln Thr Trp Thr Asn Pro Thr Trp Asn Asn Gln Thr<br>                210                    215                    220 | | 855 |
| tgg acc aac cca act tgg agc agc cag gcc tgg acc gct cag tcc tgg<br>Trp Thr Asn Pro Thr Trp Ser Ser Gln Ala Trp Thr Ala Gln Ser Trp<br>                225                    230                    235 | | 903 |
| aac ggc cag cct tgg aat gct gct ccg ctc cat aac ttc ggg gag gac<br>Asn Gly Gln Pro Trp Asn Ala Ala Pro Leu His Asn Phe Gly Glu Asp<br>240                            245                    250 | | 951 |
| ttt ctg cag cct tac gta cag ttg cag caa aac ttc tct gcc agt gat<br>Phe Leu Gln Pro Tyr Val Gln Leu Gln Gln Asn Phe Ser Ala Ser Asp<br>255                            260                    265                  270 | | 999 |
| ttg gag gtg aat ttg gaa gcc act agg gaa agc cat gcg cat ttt agc<br>Leu Glu Val Asn Leu Glu Ala Thr Arg Glu Ser His Ala His Phe Ser<br>                275                    280                    285 | | 1047 |
| acc cca caa gcc ttg gaa tta ttc ctg aac tac tct gtg act cca cca<br>Thr Pro Gln Ala Leu Glu Leu Phe Leu Asn Tyr Ser Val Thr Pro Pro<br>              290                    295                    300 | | 1095 |
| ggt gaa ata tgagacttac gcaacatctg ggcttaaagt cagggcaaag cca<br>Gly Glu Ile<br>          305 | | 1147 |
| ggttccttcc ttcttccaaa tatttcata tttttttaa agatttattt attcattata | | 1207 |
| tgtaagtaca ctgtagctgt cttcagacac tccagaagag ggcgtcgat cttgttacgt | | 1267 |
| atggttgtga gccaccatgt ggttgctggg atttgaactc ctgaccttcg aagagcagt | | 1327 |
| cgggtgctct tatccactga gccatctcac cagcccctgg tttatttttt taattattat | | 1387 |
| ttgcttttg tttatcaaga cagggtttct ctgcatagct ctaattgtct ttgaactagc | | 1447 |
| tctgcagacc agcctggcct tgaactcaga gatctgccca cttatctttg cctcctgaat | | 1507 |
| gctgggacca aaggtggcat accaccacac ctggcatata tattgtttat ttctatttct | | 1567 |
| atttttattg gtgccagagc aaacctagga cttagaacat gctgggcacc aactcaactt | | 1627 |
| ctgagctcta tttacaactt ggtgtgttag tgtatttgtc ttagttctga atttgtcctt | | 1687 |
| ttttagtgt taactctagg ctttggagac agtgaggtgc atatactctc tccttcccaa | | 1747 |

```
gaataagtgc ttgaacaccc ttacccacgc ccacccaccc atgctagtct tttttcttag   1807
aagcgtgggt cttggtatac actgtgtcat tttgaggggt gaggtttaaa agtatataca   1867
aagtataacg atatggtggc tactctcgag gatgagacag aaggaccagg agtttgaggg   1927
tagctcagat atgcaataag ttcaaggcca acctgtacta tgtttaaata gtaagacagc   1987
atctcgataa aataataaaa ctaaagtctc aacaaaataa aagctttcac ctattaaggt   2047
gcttgcttgt ccttggagtc ccccaagagt aactgctatg ttaatatctg tagaaagatg   2107
tttatatttg actgtaccat gatgaaccga tgccagctgg actagtttaa acaaaataaa   2167
acactaattt taccttt                                                 2184

<210> SEQ ID NO 16
<211> LENGTH: 305
<212> TYPE: PRT
<213> ORGANISM: Mus musculus

<400> SEQUENCE: 16
```

Met Ser Val Gly Leu Pro Gly Pro His Ser Leu Pro Ser Ser Glu Glu
1               5                   10                  15

Ala Ser Asn Ser Gly Asn Ala Ser Ser Met Pro Ala Val Phe His Pro
            20                  25                  30

Glu Asn Tyr Ser Cys Leu Gln Gly Ser Ala Thr Glu Met Leu Cys Thr
        35                  40                  45

Glu Ala Ala Ser Pro Arg Pro Ser Ser Glu Asp Leu Pro Leu Gln Gly
    50                  55                  60

Ser Pro Asp Ser Ser Thr Ser Pro Lys Gln Lys Leu Ser Ser Pro Glu
65                  70                  75                  80

Ala Asp Lys Gly Pro Glu Glu Glu Asn Lys Val Leu Ala Arg Lys
                85                  90                  95

Gln Lys Met Arg Thr Val Phe Ser Gln Ala Gln Leu Cys Ala Leu Lys
            100                 105                 110

Asp Arg Phe Gln Lys Gln Lys Tyr Leu Ser Leu Gln Gln Met Gln Glu
        115                 120                 125

Leu Ser Ser Ile Leu Asn Leu Ser Tyr Lys Gln Val Lys Thr Trp Phe
    130                 135                 140

Gln Asn Gln Arg Val Lys Cys Lys Arg Trp Gln Lys Asn Gln Trp Leu
145                 150                 155                 160

Lys Thr Ser Asn Gly Leu Ile Gln Lys Gly Ser Ala Pro Val Glu Tyr
                165                 170                 175

Pro Ser Ile His Cys Ser Tyr Pro Gln Gly Tyr Leu Val Asn Ala Ser
            180                 185                 190

Gly Ser Leu Ser Met Trp Gly Ser Gln Thr Trp Thr Asn Pro Thr Trp
        195                 200                 205

Ser Ser Gln Thr Trp Thr Asn Pro Thr Trp Asn Asn Gln Thr Trp
    210                 215                 220

Asn Pro Thr Trp Ser Ser Gln Ala Trp Thr Ala Gln Ser Trp Asn Gly
225                 230                 235                 240

Gln Pro Trp Asn Ala Ala Pro Leu His Asn Phe Gly Glu Asp Phe Leu
                245                 250                 255

Gln Pro Tyr Val Gln Leu Gln Asn Phe Ser Ala Ser Asp Leu Glu
            260                 265                 270

Val Asn Leu Glu Ala Thr Arg Glu Ser His Ala His Phe Ser Thr Pro
        275                 280                 285

Gln Ala Leu Glu Leu Phe Leu Asn Tyr Ser Val Thr Pro Pro Gly Glu

```
                    290                 295                 300
Ile
305

<210> SEQ ID NO 17
<211> LENGTH: 1078
<212> TYPE: DNA
<213> ORGANISM: Mus musculus
<220> FEATURE:
<221> NAME/KEY: CDS
<222> LOCATION: (178)..(858)

<400> SEQUENCE: 17 cagggtcgg gcaggtggga gggggaagct cacatctccg ccctctgctg cctctggggg      60
tagggagcat cctaaccccc aactgtccgg tcagatccgc ctactgcccc tcatcagact    120
gctactcctg ggagcacagc acctgctctt tacacctctt ccttgagctg ctggga        177 atg gct ttg cct aca aag tct agc atc ttg gac ctg agc tcc ggc acc     225
Met Ala Leu Pro Thr Lys Ser Ser Ile Leu Asp Leu Ser Ser Gly Thr
 1               5                  10                  15 cca tgc acc aga tct cca gag gaa agt cac gag gct tgg gca cag tgc     273
Pro Cys Thr Arg Ser Pro Glu Glu Ser His Glu Ala Trp Ala Gln Cys
             20                  25                  30 aaa gat gct ggc agg cag cta ccc gag tac aag gca gtg gtg gtg ggt     321
Lys Asp Ala Gly Arg Gln Leu Pro Glu Tyr Lys Ala Val Val Val Gly
         35                  40                  45 gca agt ggt gtt ggt aaa agt gct ctc acc atc cag atg act cac caa     369
Ala Ser Gly Val Gly Lys Ser Ala Leu Thr Ile Gln Met Thr His Gln
     50                  55                  60 tgc ttc gtg aaa gac cat gac ccc act atc caa gat tcc tac tgg aag     417
Cys Phe Val Lys Asp His Asp Pro Thr Ile Gln Asp Ser Tyr Trp Lys
 65                  70                  75                  80 gaa gtg gcc agg gac aac gga ggc tac att cta aat gtt ctg gat aca     465
Glu Val Ala Arg Asp Asn Gly Gly Tyr Ile Leu Asn Val Leu Asp Thr
                 85                  90                  95 tct ggg cag gat att cac cgg gct ctg cgt gac cag tgc ttg gca tct     513
Ser Gly Gln Asp Ile His Arg Ala Leu Arg Asp Gln Cys Leu Ala Ser
            100                 105                 110 ggt gat ggt gtg ctg ggc gtc ttt gct ctt gac gac ccc tcg tct ctg     561
Gly Asp Gly Val Leu Gly Val Phe Ala Leu Asp Asp Pro Ser Ser Leu
        115                 120                 125 gac cag ttg cag cag ata tgg tcc acc tgg acc cct cac cac aag cag     609
Asp Gln Leu Gln Gln Ile Trp Ser Thr Trp Thr Pro His His Lys Gln
    130                 135                 140 cct ctg gta cta gtg ggc aac aag tgt gac ctg gtg acc act gct gga     657
Pro Leu Val Leu Val Gly Asn Lys Cys Asp Leu Val Thr Thr Ala Gly
145                 150                 155                 160 gat gct cat gct gcc gca gcc ctc ctt gct cac aag ttg ggg gcc ccc     705
Asp Ala His Ala Ala Ala Ala Leu Leu Ala His Lys Leu Gly Ala Pro
                165                 170                 175 ttg gtg aag acc tca gcc aag acg cgg caa ggt gtg gag gaa gcc ttt     753
Leu Val Lys Thr Ser Ala Lys Thr Arg Gln Gly Val Glu Glu Ala Phe
            180                 185                 190 gcc ctg ctt gtc cat gag att cag agg gcc cag gag gct gtg gcc gaa     801
Ala Leu Leu Val His Glu Ile Gln Arg Ala Gln Glu Ala Val Ala Glu
        195                 200                 205 tca agc aag aag acc cga cac cag aaa gcc gtg tgt agc tgt ggc tgc     849
Ser Ser Lys Lys Thr Arg His Gln Lys Ala Val Cys Ser Cys Gly Cys
    210                 215                 220 tct gta gcc tgaagatctt tgtctagcaa attgaccctt gtctcatgtc             898
Ser Val Ala
```

```
aaggtgacaa ttctcttgta ataagatctc cctctccgac caagttacca cagacatctt      958
tttattgtca tttggtgaga agttacgtgg taacatggga catccctcat tgactgtgtt     1018
ttatgaaact ctatgcaaaa ttaaataaat gttttcagga ttcaaagctt cctttatacc     1078
```

<210> SEQ ID NO 18
<211> LENGTH: 227
<212> TYPE: PRT
<213> ORGANISM: Mus musculus

<400> SEQUENCE: 18

```
Met Ala Leu Pro Thr Lys Ser Ser Ile Leu Asp Leu Ser Ser Gly Thr
1               5                   10                  15

Pro Cys Thr Arg Ser Pro Glu Glu Ser His Glu Ala Trp Ala Gln Cys
            20                  25                  30

Lys Asp Ala Gly Arg Gln Leu Pro Glu Tyr Lys Ala Val Val Val Gly
        35                  40                  45

Ala Ser Gly Val Gly Lys Ser Ala Leu Thr Ile Gln Met Thr His Gln
    50                  55                  60

Cys Phe Val Lys Asp His Asp Pro Thr Ile Gln Asp Ser Tyr Trp Lys
65                  70                  75                  80

Glu Val Ala Arg Asp Asn Gly Gly Tyr Ile Leu Asn Val Leu Asp Thr
                85                  90                  95

Ser Gly Gln Asp Ile His Arg Ala Leu Arg Asp Gln Cys Leu Ala Ser
            100                 105                 110

Gly Asp Gly Val Leu Gly Val Phe Ala Leu Asp Asp Pro Ser Ser Leu
        115                 120                 125

Asp Gln Leu Gln Gln Ile Trp Ser Thr Trp Thr Pro His His Lys Gln
    130                 135                 140

Pro Leu Val Leu Val Gly Asn Lys Cys Asp Leu Val Thr Thr Ala Gly
145                 150                 155                 160

Asp Ala His Ala Ala Ala Leu Leu Ala His Lys Leu Gly Ala Pro
                165                 170                 175

Leu Val Lys Thr Ser Ala Lys Thr Arg Gln Gly Val Glu Glu Ala Phe
            180                 185                 190

Ala Leu Leu Val His Glu Ile Gln Arg Ala Gln Glu Ala Val Ala Glu
        195                 200                 205

Ser Ser Lys Lys Thr Arg His Gln Lys Ala Val Cys Ser Cys Gly Cys
    210                 215                 220

Ser Val Ala
225
```

<210> SEQ ID NO 19
<211> LENGTH: 1063
<212> TYPE: DNA
<213> ORGANISM: Mus musculus
<220> FEATURE:
<221> NAME/KEY: CDS
<222> LOCATION: (177)..(872)

<400> SEQUENCE: 19

```
gatacaaatt cgaatgtagg tgctaggcgc gcttgtgtta gagtgtttgt tagggagac       60 tgatggaatc cacagtccaa tgagtacagg gcctgtcctc cgtgtggcag cttcacccgg     120
gagttgctgg cctggctgcc tacctgcttt cctgagatcc agggactttt cccaga atg     179
                                                                Met
                                                                1
```

```
gct ttg ggt gac ctc ctg ctg tct gtc ctc tct gcc cag gaa atg aat      227
Ala Leu Gly Asp Leu Leu Leu Ser Val Leu Ser Ala Gln Glu Met Asn
         5                  10                  15 gcc ctt cgt ggc cag gtg ggc ggg gac gtc aat gtg gag atg gac gcc      275
Ala Leu Arg Gly Gln Val Gly Gly Asp Val Asn Val Glu Met Asp Ala
     20                  25                  30 gcc ccc ggt gtg gac ctg agc cgc atc ctg aac gag atg cgg gat cag      323
Ala Pro Gly Val Asp Leu Ser Arg Ile Leu Asn Glu Met Arg Asp Gln
 35                  40                  45 tat gag aag atg gcg gag aag aac cgc aag gat gct gag gaa tgg ttc      371
Tyr Glu Lys Met Ala Glu Lys Asn Arg Lys Asp Ala Glu Glu Trp Phe
50                  55                  60                  65 ttc acc aag aca gag gag ctg aac cga gaa gtg gcc acc aac acg gag      419
Phe Thr Lys Thr Glu Glu Leu Asn Arg Glu Val Ala Thr Asn Thr Glu
             70                  75                  80 gcc ctg cag agc agc cgg aca gag atc acg gag ctc cgc cgc tct gtg      467
Ala Leu Gln Ser Ser Arg Thr Glu Ile Thr Glu Leu Arg Arg Ser Val
                 85                  90                  95 cag aac ctg gag att gag ctg cag tcc cag ctc agc atg aaa gca tca      515
Gln Asn Leu Glu Ile Glu Leu Gln Ser Gln Leu Ser Met Lys Ala Ser
                    100                 105                 110 ctg gag aac agc ctg gca gag aca gag gcg cgc tat ggg gcc cag ctg      563
Leu Glu Asn Ser Leu Ala Glu Thr Glu Ala Arg Tyr Gly Ala Gln Leu
             115                 120                 125 gcg cag ctg cag ggc ctc att agc agt gtg gaa cag cag ctg tgt gag      611
Ala Gln Leu Gln Gly Leu Ile Ser Ser Val Glu Gln Gln Leu Cys Glu
130                 135                 140                 145 ctg cgt tgt gac atg gaa agg cag aat cat gag tac cag gtg ctg ctg      659
Leu Arg Cys Asp Met Glu Arg Gln Asn His Glu Tyr Gln Val Leu Leu
                 150                 155                 160 gat gtg aag acc cga ctg gag cag gag atc gcc acc tac cgc cgt ctg      707
Asp Val Lys Thr Arg Leu Glu Gln Glu Ile Ala Thr Tyr Arg Arg Leu
             165                 170                 175 ctg gag ggc gag gac gcc cac ctg gct act caa tac tcc tca tcc ctg      755
Leu Glu Gly Glu Asp Ala His Leu Ala Thr Gln Tyr Ser Ser Ser Leu
         180                 185                 190 gct tcg cag ccc tcc cga gaa ggc atg gtg acc agc cgc cag gtg cgc      803
Ala Ser Gln Pro Ser Arg Glu Gly Met Val Thr Ser Arg Gln Val Arg
     195                 200                 205 acc att gtg gag gaa gtc cag gat ggt aag gtg ttt tcc tcc aga gag      851
Thr Ile Val Glu Glu Val Gln Asp Gly Lys Val Phe Ser Ser Arg Glu
 210                 215                 220                 225 cag gag cac cgc tcc acc cac tgaggcccct gtctgcgtat gatagcccag        902
Gln Glu His Arg Ser Thr His
                 230 gcccaggacc ttaggctgca gctccctgca tctactgcca agcctgaact cctatgagct    962 agctgttgcc ttctgtgttt gctttgtgct gccccttaca gagaggcccc ttgggttgac   1022 cccagaaatt gctaataaag ctttgaagaa gtctgatcct t                       1063

<210> SEQ ID NO 20
<211> LENGTH: 232
<212> TYPE: PRT
<213> ORGANISM: Mus musculus

<400> SEQUENCE: 20

Met Ala Leu Gly Asp Leu Leu Leu Ser Val Leu Ser Ala Gln Glu Met
1               5                   10                  15

Asn Ala Leu Arg Gly Gln Val Gly Gly Asp Val Asn Val Glu Met Asp
            20                  25                  30
```

-continued

```
Ala Ala Pro Gly Val Asp Leu Ser Arg Ile Leu Asn Glu Met Arg Asp
        35                  40                  45

Gln Tyr Glu Lys Met Ala Glu Lys Asn Arg Lys Asp Ala Glu Glu Trp
 50                  55                  60

Phe Phe Thr Lys Thr Glu Leu Asn Arg Glu Val Ala Thr Asn Thr
 65                  70                  75                  80

Glu Ala Leu Gln Ser Ser Arg Thr Glu Ile Thr Glu Leu Arg Arg Ser
                 85                  90                  95

Val Gln Asn Leu Glu Ile Glu Leu Gln Ser Gln Leu Ser Met Lys Ala
            100                 105                 110

Ser Leu Glu Asn Ser Leu Ala Glu Thr Glu Ala Arg Tyr Gly Ala Gln
        115                 120                 125

Leu Ala Gln Leu Gln Gly Leu Ile Ser Ser Val Glu Gln Gln Leu Cys
    130                 135                 140

Glu Leu Arg Cys Asp Met Glu Arg Gln Asn His Glu Tyr Gln Val Leu
145                 150                 155                 160

Leu Asp Val Lys Thr Arg Leu Glu Gln Glu Ile Ala Thr Tyr Arg Arg
                165                 170                 175

Leu Leu Glu Gly Glu Asp Ala His Leu Ala Thr Gln Tyr Ser Ser Ser
            180                 185                 190

Leu Ala Ser Gln Pro Ser Arg Glu Gly Met Val Thr Ser Arg Gln Val
        195                 200                 205

Arg Thr Ile Val Glu Glu Val Gln Asp Gly Lys Val Phe Ser Ser Arg
    210                 215                 220

Glu Gln Glu His Arg Ser Thr His
225                 230
```

<210> SEQ ID NO 21
<211> LENGTH: 1670
<212> TYPE: DNA
<213> ORGANISM: Mus musculus
<220> FEATURE:
<221> NAME/KEY: CDS
<222> LOCATION: (139)..(1401)

<400> SEQUENCE: 21

```
gacaccctca accccatcat cccaggccct cataggctcc atccagcatt acgtcctcat    60
ccctacctac gggttctgac gaccctgctg tcacacccgc catcccttgg acgcagaccc   120
ttctagccga ttacatca atg ggt tcc cgg gag aca cct tct tct tgc tct   171
                     Met Gly Ser Arg Glu Thr Pro Ser Ser Cys Ser
                      1               5                  10 aag acc ctt gaa acc ttg gac ctg gag act tcc gac agc tct agc cct   219
Lys Thr Leu Glu Thr Leu Asp Leu Glu Thr Ser Asp Ser Ser Ser Pro
            15                  20                  25 gat gct gac agt cct ctg gaa gag caa tgg ctg aaa tcc tcc cca gcc   267
Asp Ala Asp Ser Pro Leu Glu Glu Gln Trp Leu Lys Ser Ser Pro Ala
         30                  35                  40 ctg aag gag gac agt gtg gat gtg gta ctg gaa gac tgc aaa gag cct   315
Leu Lys Glu Asp Ser Val Asp Val Val Leu Glu Asp Cys Lys Glu Pro
     45                  50                  55 ctg tcc ccc tcc tcg cct ccg aca ggc aga gag atg atc agg tac gaa   363
Leu Ser Pro Ser Ser Pro Pro Thr Gly Arg Glu Met Ile Arg Tyr Glu
 60                  65                  70                  75 gtc aaa gtg aac cga cgg agc att gaa gac atc tgc ctc tgc tgt gga   411
Val Lys Val Asn Arg Arg Ser Ile Glu Asp Ile Cys Leu Cys Cys Gly
                 80                  85                  90 act ctc cag gtg tac act cgg cac ccc ttg ttt gag gga ggg tta tgt   459
Thr Leu Gln Val Tyr Thr Arg His Pro Leu Phe Glu Gly Gly Leu Cys
```

```
                      95                      100                     105
gcc cca tgt aag gat aag ttc ctg gag tcc ctc ttc ctg tat gat gat      507
Ala Pro Cys Lys Asp Lys Phe Leu Glu Ser Leu Phe Leu Tyr Asp Asp
            110                     115                     120 gat gga cac cag agt tac tgc acc atc tgc tgt tcc ggg ggt acc ctg      555
Asp Gly His Gln Ser Tyr Cys Thr Ile Cys Cys Ser Gly Gly Thr Leu
            125                     130                     135 ttc atc tgt gag agc ccc gac tgt acc aga tgc tac tgt ttc gag tgt      603
Phe Ile Cys Glu Ser Pro Asp Cys Thr Arg Cys Tyr Cys Phe Glu Cys
140                     145                     150                     155 gtg gac atc ctg gtg ggc ccc ggg acc tca gag agg atc aat gcc atg      651
Val Asp Ile Leu Val Gly Pro Gly Thr Ser Glu Arg Ile Asn Ala Met
                    160                     165                     170 gcc tgc tgg gtt tgc ttc ctg tgc ctg ccc ttc tca cgg agt gga ctg      699
Ala Cys Trp Val Cys Phe Leu Cys Leu Pro Phe Ser Arg Ser Gly Leu
                175                     180                     185 ctg cag agg cgc aag agg tgg cgg cac cag ctg aag gcc ttc cat gat      747
Leu Gln Arg Arg Lys Arg Trp Arg His Gln Leu Lys Ala Phe His Asp
            190                     195                     200 caa gag gga gcg ggc cct atg gag ata tac aag aca gtg tct gca tgg      795
Gln Glu Gly Ala Gly Pro Met Glu Ile Tyr Lys Thr Val Ser Ala Trp
        205                     210                     215 aag aga cag cca gtg cgg gta ctg agc ctt ttt aga aat att gat aaa      843
Lys Arg Gln Pro Val Arg Val Leu Ser Leu Phe Arg Asn Ile Asp Lys
220                     225                     230                     235 gta cta aag agt ttg ggc ttt ttg gaa agc ggt tct ggt tct ggg gga      891
Val Leu Lys Ser Leu Gly Phe Leu Glu Ser Gly Ser Gly Ser Gly Gly
                    240                     245                     250 gga acg ctg aag tac gtg gaa gat gtc aca aat gtc gtg agg aga gac      939
Gly Thr Leu Lys Tyr Val Glu Asp Val Thr Asn Val Val Arg Arg Asp
                255                     260                     265 gtg gag aaa tgg ggc ccc ttt gac ctg gtg tac ggc tcg acg cag ccc      987
Val Glu Lys Trp Gly Pro Phe Asp Leu Val Tyr Gly Ser Thr Gln Pro
            270                     275                     280 cta ggc agc tct tgt gat cgc tgt ccc ggc tgg tac atg ttc cag ttc     1035
Leu Gly Ser Ser Cys Asp Arg Cys Pro Gly Trp Tyr Met Phe Gln Phe
        285                     290                     295 cac cgg atc ctg cag tat gcg ctg cct cgc cag gag agt cag cgg ccc     1083
His Arg Ile Leu Gln Tyr Ala Leu Pro Arg Gln Glu Ser Gln Arg Pro
300                     305                     310                     315 ttc ttc tgg ata ttc atg gac aat ctg ctg ctg act gag gat gac caa     1131
Phe Phe Trp Ile Phe Met Asp Asn Leu Leu Leu Thr Glu Asp Asp Gln
                    320                     325                     330 gag aca act acc cgc ttc ctt cag aca gag gct gtg acc ctc cag gat     1179
Glu Thr Thr Thr Arg Phe Leu Gln Thr Glu Ala Val Thr Leu Gln Asp
                335                     340                     345 gtc cgt ggc aga gac tac cag aat gct atg cgg gtg tgg agc aac att     1227
Val Arg Gly Arg Asp Tyr Gln Asn Ala Met Arg Val Trp Ser Asn Ile
            350                     355                     360 cca ggg ctg aag agc aag cat gcg ccc ctg acc cca aag gaa gaa gag     1275
Pro Gly Leu Lys Ser Lys His Ala Pro Leu Thr Pro Lys Glu Glu Glu
        365                     370                     375 tat ctg caa gcc caa gtc aga agc agg agc aag ctg gac gcc ccg aaa     1323
Tyr Leu Gln Ala Gln Val Arg Ser Arg Ser Lys Leu Asp Ala Pro Lys
380                     385                     390                     395 gtt gac ctc ctg gtg aag aac tgc ctt ctc ccg ctg aga gag tac ttc     1371
Val Asp Leu Leu Val Lys Asn Cys Leu Leu Pro Leu Arg Glu Tyr Phe
                    400                     405                     410 aag tat ttt tct caa aac tca ctt cct ctt tagaaatgaa tcaccataag       1421
Lys Tyr Phe Ser Gln Asn Ser Leu Pro Leu
```

```
                      415                  420
atgaaagtct ttcctagaac cagggcagat ttcttcctaa ggtctcttcc ctccacagtt      1481
ttctctggtt tgctttcagg ccttcgggtt tctctcctgt ttgattgcca ggatgcctct      1541
gtgcagctca ctttgcgggg tgggaggtgc ctacggctct gcacaagttc ccggtgggat      1601
aacctgccat gtttctctga aactgtgtgt acctgttgtg aagttttca aatatatcat       1661 aggattgtt                                                              1670
```

<210> SEQ ID NO 22
<211> LENGTH: 421
<212> TYPE: PRT
<213> ORGANISM: Mus musculus
<400> SEQUENCE: 22

```
Met Gly Ser Arg Glu Thr Pro Ser Ser Cys Ser Lys Thr Leu Glu Thr
1               5                   10                  15

Leu Asp Leu Glu Thr Ser Asp Ser Ser Pro Asp Ala Asp Ser Pro
            20                  25                  30

Leu Glu Glu Gln Trp Leu Lys Ser Pro Ala Leu Lys Glu Asp Ser
        35                  40                      45

Val Asp Val Val Leu Glu Asp Cys Lys Glu Pro Leu Ser Pro Ser Ser
50                  55                  60

Pro Pro Thr Gly Arg Glu Met Ile Arg Tyr Glu Val Lys Val Asn Arg
65                  70                  75                  80

Arg Ser Ile Glu Asp Ile Cys Leu Cys Cys Gly Thr Leu Gln Val Tyr
                85                  90                  95

Thr Arg His Pro Leu Phe Glu Gly Gly Leu Cys Ala Pro Cys Lys Asp
                100                 105                 110

Lys Phe Leu Glu Ser Leu Phe Leu Tyr Asp Asp Asp Gly His Gln Ser
            115                 120                 125

Tyr Cys Thr Ile Cys Cys Ser Gly Gly Thr Leu Phe Ile Cys Glu Ser
        130                 135                 140

Pro Asp Cys Thr Arg Cys Tyr Cys Phe Glu Cys Val Asp Ile Leu Val
145                 150                 155                 160

Gly Pro Gly Thr Ser Glu Arg Ile Asn Ala Met Ala Cys Trp Val Cys
                165                 170                 175

Phe Leu Cys Leu Pro Phe Ser Arg Ser Gly Leu Leu Gln Arg Arg Lys
                180                 185                 190

Arg Trp Arg His Gln Leu Lys Ala Phe His Asp Gln Glu Gly Ala Gly
            195                 200                 205

Pro Met Glu Ile Tyr Lys Thr Val Ser Ala Trp Lys Arg Gln Pro Val
        210                 215                 220

Arg Val Leu Ser Leu Phe Arg Asn Ile Asp Lys Val Leu Lys Ser Leu
225                 230                 235                 240

Gly Phe Leu Glu Ser Gly Ser Gly Ser Gly Gly Thr Leu Lys Tyr
                245                 250                 255

Val Glu Asp Val Thr Asn Val Val Arg Arg Asp Val Glu Lys Trp Gly
            260                 265                 270

Pro Phe Asp Leu Val Tyr Gly Ser Thr Gln Pro Leu Gly Ser Ser Cys
        275                 280                 285

Asp Arg Cys Pro Gly Trp Tyr Met Phe Gln Phe His Arg Ile Leu Gln
        290                 295                 300

Tyr Ala Leu Pro Arg Gln Glu Ser Gln Arg Pro Phe Phe Trp Ile Phe
305                 310                 315                 320
```

```
Met Asp Asn Leu Leu Leu Thr Glu Asp Asp Gln Glu Thr Thr Thr Arg
            325                 330                 335

Phe Leu Gln Thr Glu Ala Val Thr Leu Gln Asp Val Arg Gly Arg Asp
        340                 345                 350

Tyr Gln Asn Ala Met Arg Val Trp Ser Asn Ile Pro Gly Leu Lys Ser
        355                 360                 365

Lys His Ala Pro Leu Thr Pro Lys Glu Glu Tyr Leu Gln Ala Gln
        370                 375                 380

Val Arg Ser Arg Ser Lys Leu Asp Ala Pro Lys Val Asp Leu Leu Val
385                 390                 395                 400

Lys Asn Cys Leu Leu Pro Leu Arg Glu Tyr Phe Lys Tyr Phe Ser Gln
            405                 410                 415

Asn Ser Leu Pro Leu
            420

<210> SEQ ID NO 23
<211> LENGTH: 1560
<212> TYPE: DNA
<213> ORGANISM: Mus musculus
<220> FEATURE:
<221> NAME/KEY: CDS
<222> LOCATION: (147)..(1367)

<400> SEQUENCE: 23
ggtgcatgct aggggcttac gaaggctggt ggtgcagagg ctcccaggcc aggtcttttt      60
gtcggtggtg agggacgctc actctcactc cgcgtgctgt ctccccgtct gtgtgctgtg     120
atctcctctg tgagagaagg gccagg atg ttc gag gtc ctg gtg ctg aag att     173
                             Met Phe Glu Val Leu Val Leu Lys Ile
                               1               5 gaa gat cca ggt tgc ttc tgg gta att ata aaa gga tgt agt cat ttt     221
Glu Asp Pro Gly Cys Phe Trp Val Ile Ile Lys Gly Cys Ser His Phe
 10                  15                  20                  25 tta gaa caa gaa gtt gac tac caa aaa cta aac act gcc atg aat gac     269
Leu Glu Gln Glu Val Asp Tyr Gln Lys Leu Asn Thr Ala Met Asn Asp
                 30                  35                  40 ttc tat aac agc atg tgt cag gac gta gaa atg aaa cca tta atg ctg     317
Phe Tyr Asn Ser Met Cys Gln Asp Val Glu Met Lys Pro Leu Met Leu
             45                  50                  55 gaa gaa ggg cag gtg tgt gtg gtg tac tgc cag gag ctg aag tgc tgg     365
Glu Glu Gly Gln Val Cys Val Val Tyr Cys Gln Glu Leu Lys Cys Trp
         60                  65                  70 tgc agg gct ctg att aag tcc atc atc tct tct gca gac cat tac ctg     413
Cys Arg Ala Leu Ile Lys Ser Ile Ile Ser Ser Ala Asp His Tyr Leu
     75                  80                  85 gca gag tgt ttc ctg gtc gat ttt gcc aag tat att cca gta aaa tct     461
Ala Glu Cys Phe Leu Val Asp Phe Ala Lys Tyr Ile Pro Val Lys Ser
 90                  95                 100                 105 aaa aac atc cga gtt gca gta gag tct ttt atg cag ctt cct tac aga     509
Lys Asn Ile Arg Val Ala Val Glu Ser Phe Met Gln Leu Pro Tyr Arg
                110                 115                 120 gca aaa aaa ttc aga ctt tac ggt aca aag cct gtg aca ttg cac att     557
Ala Lys Lys Phe Arg Leu Tyr Gly Thr Lys Pro Val Thr Leu His Ile
            125                 130                 135 gac ttc tgt gaa gac aat gct gag att gta cct gcc aca aaa tgg gac     605
Asp Phe Cys Glu Asp Asn Ala Glu Ile Val Pro Ala Thr Lys Trp Asp
        140                 145                 150 agt gca gcc atc cag tac ttt cag aac ctt cta aga gca act acc caa     653
Ser Ala Ala Ile Gln Tyr Phe Gln Asn Leu Leu Arg Ala Thr Thr Gln
    155                 160                 165
```

```
gtg gaa gca aaa cta tgt gcg gtg gaa gaa gat act ttt gag gtt tac    701
Val Glu Ala Lys Leu Cys Ala Val Glu Glu Asp Thr Phe Glu Val Tyr
170             175                 180                 185 ctt tat gca aca ata aaa aat gaa aaa gtt tgt gtt aat gat gac cta    749
Leu Tyr Ala Thr Ile Lys Asn Glu Lys Val Cys Val Asn Asp Asp Leu
        190                 195                 200 gtt gca aag aat ttt gct tat tat gtg tca cca atg ggg aat aaa aac    797
Val Ala Lys Asn Phe Ala Tyr Tyr Val Ser Pro Met Gly Asn Lys Asn
    205                 210                 215 ctc aat cct ttg gag aaa ccc agg cag agt ctc aat tcg gtg acc tgc    845
Leu Asn Pro Leu Glu Lys Pro Arg Gln Ser Leu Asn Ser Val Thr Cys
220                 225                 230 tcc agt aag ctc agc cca tca ctt act ctg tgg cca atg ctt cta caa    893
Ser Ser Lys Leu Ser Pro Ser Leu Thr Leu Trp Pro Met Leu Leu Gln
235                 240                 245 gga aaa gac tat cac aga atg gaa aat aaa gct cta aac tat aag gat    941
Gly Lys Asp Tyr His Arg Met Glu Asn Lys Ala Leu Asn Tyr Lys Asp
250             255                 260                 265 tcc ttg aca gac tcg cct aaa atg atg ctt gag aag cag cag cag agc    989
Ser Leu Thr Asp Ser Pro Lys Met Met Leu Glu Lys Gln Gln Gln Ser
        270                 275                 280 ctc cct tta aag cac acg gag aag tgt act gaa tct tct gtg tac tgg   1037
Leu Pro Leu Lys His Thr Glu Lys Cys Thr Glu Ser Ser Val Tyr Trp
    285                 290                 295 cca acc aaa aga ggc ata acc ata tat gct gat cca gat gtt cca tca   1085
Pro Thr Lys Arg Gly Ile Thr Ile Tyr Ala Asp Pro Asp Val Pro Ser
300                 305                 310 gta agt ggg tct agc cag agg ccg aat gag aag cca ctg cgg ttg act   1133
Val Ser Gly Ser Ser Gln Arg Pro Asn Glu Lys Pro Leu Arg Leu Thr
315                 320                 325 gaa aag aaa gac tgt gac gag aag aac ggc tgt gta aaa tta ctg cag   1181
Glu Lys Lys Asp Cys Asp Glu Lys Asn Gly Cys Val Lys Leu Leu Gln
330             335                 340                 345 ttt cta aat cct gat cct ttg aga gct gat ggg acc tca gac ctg cac   1229
Phe Leu Asn Pro Asp Pro Leu Arg Ala Asp Gly Thr Ser Asp Leu His
        350                 355                 360 cag ttg cag aag gtg aag ctg ggc aca ctg cag cct ggg gtg gtg ctc   1277
Gln Leu Gln Lys Val Lys Leu Gly Thr Leu Gln Pro Gly Val Val Leu
    365                 370                 375 cgg aac agg atc gag ccc tgc cta acc ctg gag aaa tca cct ctg tcg   1325
Arg Asn Arg Ile Glu Pro Cys Leu Thr Leu Glu Lys Ser Pro Leu Ser
380                 385                 390 gca gac ctg aag aag gtg aac atg ttc tta aag cca gac tcc             1367
Ala Asp Leu Lys Lys Val Asn Met Phe Leu Lys Pro Asp Ser
395                 400                 405 tgacgacatg ccagcccttt ccaacacaga gtgttgcttt gttttgcttt gtctgttctg   1427
ttctaagagt gacggggatg aaatacaggg ctttgcgcgt cctgggcatg cattcatcac   1487
tgaaccatac cccaattcca taggaggatt ttaaataaac acttctaagg ctacattgca   1547
gaattcttgc tcc                                                    1560

<210> SEQ ID NO 24
<211> LENGTH: 407
<212> TYPE: PRT
<213> ORGANISM: Mus musculus

<400> SEQUENCE: 24

Met Phe Glu Val Leu Val Leu Lys Ile Glu Asp Pro Gly Cys Phe Trp
1               5                   10                  15

Val Ile Ile Lys Gly Cys Ser His Phe Leu Glu Gln Glu Val Asp Tyr
```

```
                20                  25                  30
Gln Lys Leu Asn Thr Ala Met Asn Asp Phe Tyr Asn Ser Met Cys Gln
            35                  40                  45

Asp Val Glu Met Lys Pro Leu Met Leu Glu Glu Gly Gln Val Cys Val
        50                  55                  60

Val Tyr Cys Gln Glu Leu Lys Cys Trp Cys Arg Ala Leu Ile Lys Ser
65                  70                  75                  80

Ile Ile Ser Ser Ala Asp His Tyr Leu Ala Glu Cys Phe Leu Val Asp
                85                  90                  95

Phe Ala Lys Tyr Ile Pro Val Lys Ser Lys Asn Ile Arg Val Ala Val
            100                 105                 110

Glu Ser Phe Met Gln Leu Pro Tyr Arg Ala Lys Lys Phe Arg Leu Tyr
        115                 120                 125

Gly Thr Lys Pro Val Thr Leu His Ile Asp Phe Cys Glu Asp Asn Ala
            130                 135                 140

Glu Ile Val Pro Ala Thr Lys Trp Asp Ser Ala Ile Gln Tyr Phe
145                 150                 155                 160

Gln Asn Leu Leu Arg Ala Thr Thr Gln Val Glu Ala Lys Leu Cys Ala
                165                 170                 175

Val Glu Glu Asp Thr Phe Glu Val Tyr Leu Tyr Ala Thr Ile Lys Asn
            180                 185                 190

Glu Lys Val Cys Val Asn Asp Asp Leu Val Ala Lys Asn Phe Ala Tyr
        195                 200                 205

Tyr Val Ser Pro Met Gly Asn Lys Asn Leu Asn Pro Leu Glu Lys Pro
    210                 215                 220

Arg Gln Ser Leu Asn Ser Val Thr Cys Ser Ser Lys Leu Ser Pro Ser
225                 230                 235                 240

Leu Thr Leu Trp Pro Met Leu Leu Gln Gly Lys Asp Tyr His Arg Met
                245                 250                 255

Glu Asn Lys Ala Leu Asn Tyr Lys Asp Ser Leu Thr Asp Ser Pro Lys
            260                 265                 270

Met Met Leu Glu Lys Gln Gln Gln Ser Leu Pro Leu Lys His Thr Glu
        275                 280                 285

Lys Cys Thr Glu Ser Ser Val Tyr Trp Pro Thr Lys Arg Gly Ile Thr
    290                 295                 300

Ile Tyr Ala Asp Pro Asp Val Pro Ser Val Ser Gly Ser Ser Gln Arg
305                 310                 315                 320

Pro Asn Glu Lys Pro Leu Arg Leu Thr Glu Lys Lys Asp Cys Asp Glu
                325                 330                 335

Lys Asn Gly Cys Val Lys Leu Leu Gln Phe Leu Asn Pro Asp Pro Leu
            340                 345                 350

Arg Ala Asp Gly Thr Ser Asp Leu His Gln Leu Gln Lys Val Lys Leu
        355                 360                 365

Gly Thr Leu Gln Pro Gly Val Val Leu Arg Asn Arg Ile Glu Pro Cys
    370                 375                 380

Leu Thr Leu Glu Lys Ser Pro Leu Ser Ala Asp Leu Lys Lys Val Asn
385                 390                 395                 400

Met Phe Leu Lys Pro Asp Ser
                405

<210> SEQ ID NO 25
<211> LENGTH: 1248
<212> TYPE: DNA
<213> ORGANISM: Mus musculus
<220> FEATURE:
```

```
<221> NAME/KEY: CDS
<222> LOCATION: (32)..(1003)

<400> SEQUENCE: 25
agtggatccc ccgggctgca ggaattccgg g atg gat cct cga acc tgg cta         52
                                   Met Asp Pro Arg Thr Trp Leu
                                   1               5 agc ttc caa ggg cct cca ggt ggg cct gga atc gga cca ggc tca gag        100
Ser Phe Gln Gly Pro Pro Gly Gly Pro Gly Ile Gly Pro Gly Ser Glu
        10                  15                  20 gta ttg ggg atc tcc cca tgt ccg ccc gca tac gag ttc tgc gga ggg        148
Val Leu Gly Ile Ser Pro Cys Pro Pro Ala Tyr Glu Phe Cys Gly Gly
 25                  30                  35 atg gca tac tgt gga cct cag gtt ggt ctg ggc cta gtc ccc caa gtt        196
Met Ala Tyr Cys Gly Pro Gln Val Gly Leu Gly Leu Val Pro Gln Val
 40                  45                  50                  55 ggc gtg gag act ttg cag cct gag ggc cag gca gga gca cga gtg gaa        244
Gly Val Glu Thr Leu Gln Pro Glu Gly Gln Ala Gly Ala Arg Val Glu
                     60                  65                  70 agc aac tca gag gga acc tcc tct gag ccc tgt gcc gac cgc ccc aat        292
Ser Asn Ser Glu Gly Thr Ser Ser Glu Pro Cys Ala Asp Arg Pro Asn
             75                  80                  85 gcc gtg aag ttg gag aag gtg gaa cca act ccc gag gag tcc cag gac        340
Ala Val Lys Leu Glu Lys Val Glu Pro Thr Pro Glu Glu Ser Gln Asp
         90                  95                 100 atg aaa gcc ctg cag aag gag cta gaa cag ttt gcc aag ctg ctg aag        388
Met Lys Ala Leu Gln Lys Glu Leu Glu Gln Phe Ala Lys Leu Leu Lys
     105                 110                 115 cag aag agg atc acc ttg ggg tac acc cag gcc gac gtg ggg ctc acc        436
Gln Lys Arg Ile Thr Leu Gly Tyr Thr Gln Ala Asp Val Gly Leu Thr
120                 125                 130                 135 ctg ggc gtt ctc ttt gga aag gtg ttc agc cag acc acc atc tgt cgc        484
Leu Gly Val Leu Phe Gly Lys Val Phe Ser Gln Thr Thr Ile Cys Arg
                140                 145                 150 ttc gag gcc ttg cag ctc agc ctt aag aac atg tgt aag ctg cgg ccc        532
Phe Glu Ala Leu Gln Leu Ser Leu Lys Asn Met Cys Lys Leu Arg Pro
            155                 160                 165 ctg ctg gag aag tgg gtg gag gaa gcc gac aac aat gag aac ctt cag        580
Leu Leu Glu Lys Trp Val Glu Glu Ala Asp Asn Asn Glu Asn Leu Gln
        170                 175                 180 gag ata tgc aaa tcg gag acc ctg gtg cag gcc cgg aag aga aag cga        628
Glu Ile Cys Lys Ser Glu Thr Leu Val Gln Ala Arg Lys Arg Lys Arg
    185                 190                 195 act agc att gag aac cgt gtg agg tgg agt ctg gag acc atg ttt ctg        676
Thr Ser Ile Glu Asn Arg Val Arg Trp Ser Leu Glu Thr Met Phe Leu
200                 205                 210                 215 aag tgc ccg aag ccc tcc cta cag cag atc act cac atc gcc aat cag        724
Lys Cys Pro Lys Pro Ser Leu Gln Gln Ile Thr His Ile Ala Asn Gln
                220                 225                 230 ctt ggg cta gag aag gat gtg gtt cga gta tgg ttc tgt aac cgg cgc        772
Leu Gly Leu Glu Lys Asp Val Val Arg Val Trp Phe Cys Asn Arg Arg
            235                 240                 245 cag aag ggc aaa aga tca agt att gag tat tcc caa cga gaa gag tat        820
Gln Lys Gly Lys Arg Ser Ser Ile Glu Tyr Ser Gln Arg Glu Glu Tyr
        250                 255                 260 gag gct aca ggg aca cct ttc cca ggg ggg gct gta tcc ttt cct ctg        868
Glu Ala Thr Gly Thr Pro Phe Pro Gly Gly Ala Val Ser Phe Pro Leu
    265                 270                 275 ccc cca ggt ccc cac ttt ggc acc cca ggc tat gga agc ccc cac ttc        916
Pro Pro Gly Pro His Phe Gly Thr Pro Gly Tyr Gly Ser Pro His Phe
280                 285                 290                 295
```

```
acc aca ctc tac tca gtc cct ttt cct gag ggc gag gcc ttt ccc tct    964
Thr Thr Leu Tyr Ser Val Pro Phe Pro Glu Gly Glu Ala Phe Pro Ser
                300                 305                 310 gtt ccc gtc act gct ctg ggc tct ccc atg cat tca aac tgaggcacca    1013
Val Pro Val Thr Ala Leu Gly Ser Pro Met His Ser Asn
        315                 320 gccctccctg gggatgctgt gagccaaggc aagggaggta gacaagagaa cctggagctt  1073
tggggttaaa ttcttttact gaggagggat taaaagcaca acaggggtgg ggggtgggat  1133
ggggaaagaa gctcagtgat gctgttgatc aggagcctgg cctgtctgtc actcatcatt  1193
ttgttcttaa ataagactg ggacacacag taaaaaaaaa aaaaaaaaac tcgag        1248

<210> SEQ ID NO 26
<211> LENGTH: 324
<212> TYPE: PRT
<213> ORGANISM: Mus musculus

<400> SEQUENCE: 26

Met Asp Pro Arg Thr Trp Leu Ser Phe Gln Gly Pro Pro Gly Gly Pro
1               5                   10                  15

Gly Ile Gly Pro Gly Ser Glu Val Leu Gly Ile Ser Pro Cys Pro Pro
            20                  25                  30

Ala Tyr Glu Phe Cys Gly Gly Met Ala Tyr Cys Gly Pro Gln Val Gly
        35                  40                  45

Leu Gly Leu Val Pro Gln Val Gly Val Glu Thr Leu Gln Pro Glu Gly
    50                  55                  60

Gln Ala Gly Ala Arg Val Glu Ser Asn Ser Glu Gly Thr Ser Ser Glu
65                  70                  75                  80

Pro Cys Ala Asp Arg Pro Asn Ala Val Lys Leu Glu Lys Val Glu Pro
                85                  90                  95

Thr Pro Glu Glu Ser Gln Asp Met Lys Ala Leu Gln Lys Glu Leu Glu
            100                 105                 110

Gln Phe Ala Lys Leu Leu Lys Gln Lys Arg Ile Thr Leu Gly Tyr Thr
        115                 120                 125

Gln Ala Asp Val Gly Leu Thr Leu Gly Val Leu Phe Gly Lys Val Phe
    130                 135                 140

Ser Gln Thr Thr Ile Cys Arg Phe Glu Ala Leu Gln Leu Ser Leu Lys
145                 150                 155                 160

Asn Met Cys Lys Leu Arg Pro Leu Leu Glu Lys Trp Val Glu Glu Ala
                165                 170                 175

Asp Asn Asn Glu Asn Leu Gln Glu Ile Cys Lys Ser Glu Thr Leu Val
            180                 185                 190

Gln Ala Arg Lys Arg Lys Arg Thr Ser Ile Glu Asn Arg Val Arg Trp
        195                 200                 205

Ser Leu Glu Thr Met Phe Leu Lys Cys Pro Lys Pro Ser Leu Gln Gln
    210                 215                 220

Ile Thr His Ile Ala Asn Gln Leu Gly Leu Glu Lys Asp Val Val Arg
225                 230                 235                 240

Val Trp Phe Cys Asn Arg Arg Gln Lys Gly Lys Arg Ser Ser Ile Glu
                245                 250                 255

Tyr Ser Gln Arg Glu Glu Tyr Glu Ala Thr Gly Thr Pro Phe Pro Gly
            260                 265                 270

Gly Ala Val Ser Phe Pro Leu Pro Pro Gly Pro His Phe Gly Thr Pro
        275                 280                 285

Gly Tyr Gly Ser Pro His Phe Thr Thr Leu Tyr Ser Val Pro Phe Pro
```

```
                290               295               300
Glu Gly Glu Ala Phe Pro Ser Val Pro Val Thr Ala Leu Gly Ser Pro
305                 310               315                 320

Met His Ser Asn

<210> SEQ ID NO 27
<211> LENGTH: 640
<212> TYPE: DNA
<213> ORGANISM: Homo sapiens
<220> FEATURE:
<221> NAME/KEY: CDS
<222> LOCATION: (15)..(362)

<400> SEQUENCE: 27
ggcacgagga taag atg gga act ctc ccg gca cgt aga cat atc ccg ccg         50
                Met Gly Thr Leu Pro Ala Arg Arg His Ile Pro Pro
                  1               5                  10 tgg gtg aaa gtt ccc gaa gac ctg aaa gat cca gag gtg ttc cag gtc         98
Trp Val Lys Val Pro Glu Asp Leu Lys Asp Pro Glu Val Phe Gln Val
     15                  20                  25 cag acg cgg ctg ctg aaa gcc att ttc ggc ccg gac gga tct cga atc        146
Gln Thr Arg Leu Leu Lys Ala Ile Phe Gly Pro Asp Gly Ser Arg Ile
 30                  35                  40 cct tac atc gag cag gtg agc aag gcc atg ctc gag ctg aag gct ctg        194
Pro Tyr Ile Glu Gln Val Ser Lys Ala Met Leu Glu Leu Lys Ala Leu
 45                  50                  55                  60 gag tct tca gac ctc acc gag gtc gtg gtt tac ggc tcc tat ttg tac        242
Glu Ser Ser Asp Leu Thr Glu Val Val Val Tyr Gly Ser Tyr Leu Tyr
                 65                  70                  75 aag ctc cgg acc aag tgg atg ctc cag tcc atg gct gag tgg cac cgc        290
Lys Leu Arg Thr Lys Trp Met Leu Gln Ser Met Ala Glu Trp His Arg
             80                  85                  90 cag cgc cag gag cga ggg atg ctc aaa ctt gcc gaa gcc atg aat gcc        338
Gln Arg Gln Glu Arg Gly Met Leu Lys Leu Ala Glu Ala Met Asn Ala
         95                 100                 105 ctc gaa cta ggc cct tgg atg aag tgaaccagtt tccagccaat gcaatgaagc       392
Leu Glu Leu Gly Pro Trp Met Lys
    110                 115 cgggttgcag agattaggtt gtggccagag ctagagtgat tccttaagct tgttttaaaa      452
tctgctccag cctaaagagt taagggaaaa ccatttgttc ccttaaagag ttagggaaa       512 acccttggct ctgagtcttg ttgtgaatat ttctttgatg attgttaata aaaagtgttt      572 tttcttttt cccatttttta aaataacaa taaagtttta aataagttga taaaaaaaaa       632
aaaaaaaa                                                               640

<210> SEQ ID NO 28
<211> LENGTH: 116
<212> TYPE: PRT
<213> ORGANISM: Homo sapiens

<400> SEQUENCE: 28

Met Gly Thr Leu Pro Ala Arg Arg His Ile Pro Pro Trp Val Lys Val
 1               5                  10                  15

Pro Glu Asp Leu Lys Asp Pro Glu Val Phe Gln Val Gln Thr Arg Leu
             20                  25                  30

Leu Lys Ala Ile Phe Gly Pro Asp Gly Ser Arg Ile Pro Tyr Ile Glu
         35                  40                  45

Gln Val Ser Lys Ala Met Leu Glu Leu Lys Ala Leu Glu Ser Ser Asp
     50                  55                  60
```

```
Leu Thr Glu Val Val Val Tyr Gly Ser Tyr Leu Tyr Lys Leu Arg Thr
 65                  70                  75                  80

Lys Trp Met Leu Gln Ser Met Ala Glu Trp His Arg Gln Arg Gln Glu
                 85                  90                  95

Arg Gly Met Leu Lys Leu Ala Glu Ala Met Asn Ala Leu Glu Leu Gly
            100                 105                 110

Pro Trp Met Lys
        115

<210> SEQ ID NO 29
<211> LENGTH: 1665
<212> TYPE: DNA
<213> ORGANISM: Homo sapiens
<220> FEATURE:
<221> NAME/KEY: CDS
<222> LOCATION: (21)..(1550)

<400> SEQUENCE: 29
agggtgaact ccttgtctct atg gcg act gga cgc ggt cgg atc ttg cag cag         53
                     Met Ala Thr Gly Arg Gly Arg Ile Leu Gln Gln
                      1               5                  10 cac tgg ctc ggc ctc cag acg ctg cgc ggg ccc agc agg ggc ggt ggc         101
His Trp Leu Gly Leu Gln Thr Leu Arg Gly Pro Ser Arg Gly Gly Gly
             15                  20                  25 gcg gcc cgg ggg cgc gcc agg gcc ttt ggg tgc aga aag ggg cca ggg         149
Ala Ala Arg Gly Arg Ala Arg Ala Phe Gly Cys Arg Lys Gly Pro Gly
         30                  35                  40 gtc aag ctt tct gca ggc tct gct gcc ctg agg tgc cat gcc gga ggt         197
Val Lys Leu Ser Ala Gly Ser Ala Ala Leu Arg Cys His Ala Gly Gly
     45                  50                  55 gga cag cac tgg gag agc tct ttc tcc tgc tgt tct ggg ttc ctg gat         245
Gly Gln His Trp Glu Ser Ser Phe Ser Cys Cys Ser Gly Phe Leu Asp
 60                  65                  70                  75 gga atg cct tca gaa atc ttg ctg aag ata ttt tcc tac ttg gat gct         293
Gly Met Pro Ser Glu Ile Leu Leu Lys Ile Phe Ser Tyr Leu Asp Ala
                 80                  85                  90 gtg agc ctt ctg tgt act gga tgt gtg agc agg cgc ttt tat cat cta         341
Val Ser Leu Leu Cys Thr Gly Cys Val Ser Arg Arg Phe Tyr His Leu
             95                 100                 105 gcc aat gac aat ttt att tgg atc gga atc tac tca act gct ttt tca         389
Ala Asn Asp Asn Phe Ile Trp Ile Gly Ile Tyr Ser Thr Ala Phe Ser
         110                 115                 120 cct gca aga tca aat tgg aaa ttt aat tca gta gag aag ata gct atg         437
Pro Ala Arg Ser Asn Trp Lys Phe Asn Ser Val Glu Lys Ile Ala Met
     125                 130                 135 tct atg agc ttt ctg tca gtt cag gat aaa gaa gct ggt tat tgg aag         485
Ser Met Ser Phe Leu Ser Val Gln Asp Lys Glu Ala Gly Tyr Trp Lys
140                 145                 150                 155 aaa gaa tat atc aca aaa caa ata gca tct gta aaa gcc gca cta gct         533
Lys Glu Tyr Ile Thr Lys Gln Ile Ala Ser Val Lys Ala Ala Leu Ala
                160                 165                 170 gac att ctc aaa cct gtc aac cct tac aca ggc ctt cca gtt aag acc         581
Asp Ile Leu Lys Pro Val Asn Pro Tyr Thr Gly Leu Pro Val Lys Thr
            175                 180                 185 aaa gag gcc ctc aga ata ttt ggt tta ggt tgg gca att ata ctg aaa         629
Lys Glu Ala Leu Arg Ile Phe Gly Leu Gly Trp Ala Ile Ile Leu Lys
        190                 195                 200 gaa aaa ggt gga aaa gaa tat atc atg gag cat gtt gat ctt tcc ata         677
Glu Lys Gly Gly Lys Glu Tyr Ile Met Glu His Val Asp Leu Ser Ile
    205                 210                 215 aat gac aca tca gtt act gtt ata tgg tat ggc aaa aaa tgg cca tgc         725
```

```
Asn Asp Thr Ser Val Thr Val Ile Trp Tyr Gly Lys Trp Pro Cys
220                 225                 230                 235 cta gca tca ttg tca acc tta gat tta tgt ggc atg aca cca gtt ttt    773
Leu Ala Ser Leu Ser Thr Leu Asp Leu Cys Gly Met Thr Pro Val Phe
                    240                 245                 250 acc gac tgg tat aaa act ccc acc aaa cat aga ctc cga tgg cat tct    821
Thr Asp Trp Tyr Lys Thr Pro Thr Lys His Arg Leu Arg Trp His Ser
                255                 260                 265 tta att gca aag tac aat ctg agt cat ttg acc ata tct acc atg att    869
Leu Ile Ala Lys Tyr Asn Leu Ser His Leu Thr Ile Ser Thr Met Ile
                270                 275                 280 ggc tgt gac aga ctc att cgg atc ttc tgc ctg cac cct ggc ctc ctg    917
Gly Cys Asp Arg Leu Ile Arg Ile Phe Cys Leu His Pro Gly Leu Leu
285                 290                 295 gtg gga gtg tgg aag aag gag gaa gaa ctg gct ttt gtt atg gca aat    965
Val Gly Val Trp Lys Lys Glu Glu Glu Leu Ala Phe Val Met Ala Asn
300                 305                 310                 315 ctt cat ttt cat cac ctt gtg gag agg agc aca tta ggc tcg gct act   1013
Leu His Phe His His Leu Val Glu Arg Ser Thr Leu Gly Ser Ala Thr
                320                 325                 330 atc ccc tat gaa ctg cct cca cat agc ccc ttt ttg gat gat agc ccc   1061
Ile Pro Tyr Glu Leu Pro Pro His Ser Pro Phe Leu Asp Asp Ser Pro
                335                 340                 345 gag tat gga ctg cac ggc tac caa ctc cat gtt gat ctg cac agc ggt   1109
Glu Tyr Gly Leu His Gly Tyr Gln Leu His Val Asp Leu His Ser Gly
            350                 355                 360 ggg gtt ttc tac cta tgt ggt aca ttt cgc aat ctc ttc acc aag aga   1157
Gly Val Phe Tyr Leu Cys Gly Thr Phe Arg Asn Leu Phe Thr Lys Arg
        365                 370                 375 gga aat att gaa aat gga cat gtg aag ctc att gtt ata cat tta aaa   1205
Gly Asn Ile Glu Asn Gly His Val Lys Leu Ile Val Ile His Leu Lys
380                 385                 390                 395 aat aac aga gaa cac cta cct ctt att gga aaa gtt ggc ctc tcg tgg   1253
Asn Asn Arg Glu His Leu Pro Leu Ile Gly Lys Val Gly Leu Ser Trp
                400                 405                 410 aaa act gat att ttt gat ggc tgt ata aag agt tgt tcc atg atg gac   1301
Lys Thr Asp Ile Phe Asp Gly Cys Ile Lys Ser Cys Ser Met Met Asp
                415                 420                 425 gta act ctt ttg gat gaa cat ggg aaa ccc ttt tgg tgt ttc agt tcc   1349
Val Thr Leu Leu Asp Glu His Gly Lys Pro Phe Trp Cys Phe Ser Ser
            430                 435                 440 ccg gtg tgc ctg aga tcg cct gcc aca ccc tct gac agc tct agc ttc   1397
Pro Val Cys Leu Arg Ser Pro Ala Thr Pro Ser Asp Ser Ser Ser Phe
        445                 450                 455 ttg gga cag aca tac aac gtg gac tac gtt gat gcg gaa gga aga gtg   1445
Leu Gly Gln Thr Tyr Asn Val Asp Tyr Val Asp Ala Glu Gly Arg Val
460                 465                 470                 475 cac gtg gag ctg gtg tgg atc aga gag acc gaa gaa tac ctt att gtc   1493
His Val Glu Leu Val Trp Ile Arg Glu Thr Glu Glu Tyr Leu Ile Val
                480                 485                 490 aac ctg gtc ctt tat ctt agt atc gca aaa atc aac cat tgg ttt ggg   1541
Asn Leu Val Leu Tyr Leu Ser Ile Ala Lys Ile Asn His Trp Phe Gly
                495                 500                 505 act gaa tat tagcagtagg tggcaaatta ttgttgttat ttagttgttt           1590
Thr Glu Tyr
        510 attttttgact ggctttgttc ttggtgttga aaattaaaat aaagcaaatc tgcaaaaaaa  1650
aaaaaaaaaa aaaaa                                                    1665
```

<210> SEQ ID NO 30
<211> LENGTH: 510
<212> TYPE: PRT
<213> ORGANISM: Homo sapiens

<400> SEQUENCE: 30

Met Ala Thr Gly Arg Gly Arg Ile Leu Gln Gln His Trp Leu Gly Leu
1               5                   10                  15

Gln Thr Leu Arg Gly Pro Ser Arg Gly Gly Ala Arg Gly Arg
            20                  25                  30

Ala Arg Ala Phe Gly Cys Arg Lys Gly Pro Gly Val Lys Leu Ser Ala
            35                  40                  45

Gly Ser Ala Ala Leu Arg Cys His Ala Gly Gly Gln His Trp Glu
        50                  55                  60

Ser Ser Phe Ser Cys Cys Ser Gly Phe Leu Asp Gly Met Pro Ser Glu
65                  70                  75                  80

Ile Leu Leu Lys Ile Phe Ser Tyr Leu Asp Ala Val Ser Leu Leu Cys
                85                  90                  95

Thr Gly Cys Val Ser Arg Arg Phe Tyr His Leu Ala Asn Asp Asn Phe
            100                 105                 110

Ile Trp Ile Gly Ile Tyr Ser Thr Ala Phe Ser Pro Ala Arg Ser Asn
        115                 120                 125

Trp Lys Phe Asn Ser Val Glu Lys Ile Ala Met Ser Met Ser Phe Leu
130                 135                 140

Ser Val Gln Asp Lys Glu Ala Gly Tyr Trp Lys Lys Glu Tyr Ile Thr
145                 150                 155                 160

Lys Gln Ile Ala Ser Val Lys Ala Ala Leu Ala Asp Ile Leu Lys Pro
                165                 170                 175

Val Asn Pro Tyr Thr Gly Leu Pro Val Lys Thr Lys Glu Ala Leu Arg
            180                 185                 190

Ile Phe Gly Leu Gly Trp Ala Ile Ile Leu Lys Glu Lys Gly Gly Lys
        195                 200                 205

Glu Tyr Ile Met Glu His Val Asp Leu Ser Ile Asn Asp Thr Ser Val
210                 215                 220

Thr Val Ile Trp Tyr Gly Lys Lys Trp Pro Cys Leu Ala Ser Leu Ser
225                 230                 235                 240

Thr Leu Asp Leu Cys Gly Met Thr Pro Val Phe Thr Asp Trp Tyr Lys
                245                 250                 255

Thr Pro Thr Lys His Arg Leu Arg Trp His Ser Leu Ile Ala Lys Tyr
            260                 265                 270

Asn Leu Ser His Leu Thr Ile Ser Thr Met Ile Gly Cys Asp Arg Leu
        275                 280                 285

Ile Arg Ile Phe Cys Leu His Pro Gly Leu Leu Val Gly Val Trp Lys
290                 295                 300

Lys Glu Glu Glu Leu Ala Phe Val Met Ala Asn Leu His Phe His His
305                 310                 315                 320

Leu Val Glu Arg Ser Thr Leu Gly Ser Ala Thr Ile Pro Tyr Glu Leu
                325                 330                 335

Pro Pro His Ser Pro Phe Leu Asp Asp Ser Pro Glu Tyr Gly Leu His
            340                 345                 350

Gly Tyr Gln Leu His Val Asp Leu His Ser Gly Gly Val Phe Tyr Leu
        355                 360                 365

Cys Gly Thr Phe Arg Asn Leu Phe Thr Lys Arg Gly Asn Ile Glu Asn
370                 375                 380

Gly His Val Lys Leu Ile Val Ile His Leu Lys Asn Asn Arg Glu His

```
                385              390              395              400
Leu Pro Leu Ile Gly Lys Val Gly Leu Ser Trp Lys Thr Asp Ile Phe
                    405              410              415

Asp Gly Cys Ile Lys Ser Cys Ser Met Met Asp Val Thr Leu Leu Asp
                420              425              430

Glu His Gly Lys Pro Phe Trp Cys Phe Ser Ser Pro Val Cys Leu Arg
            435              440              445

Ser Pro Ala Thr Pro Ser Asp Ser Ser Ser Phe Leu Gly Gln Thr Tyr
        450              455              460

Asn Val Asp Tyr Val Asp Ala Glu Gly Arg Val His Val Glu Leu Val
465              470              475              480

Trp Ile Arg Glu Thr Glu Glu Tyr Leu Ile Val Asn Leu Val Leu Tyr
                485              490              495

Leu Ser Ile Ala Lys Ile Asn His Trp Phe Gly Thr Glu Tyr
                500              505              510

<210> SEQ ID NO 31
<211> LENGTH: 2114
<212> TYPE: DNA
<213> ORGANISM: Homo sapiens
<220> FEATURE:
<221> NAME/KEY: CDS
<222> LOCATION: (217)..(1131)

<400> SEQUENCE: 31
attataaatc tagagactcc aggattttaa cgttctgctg gactgagctg gttgcctcat      60
gttattatgc aggcaactca cttatccca atttcttgat acttttcctt ctggaggtcc     120
tatttctcta acatcttcca gaaaagtctt aaagctgcct taaccttttt tccagtccac     180
ctcttaaatt ttttcctcct cttcctctat actaac atg agt gtg gat cca gct      234
                                        Met Ser Val Asp Pro Ala
                                        1               5 tgt ccc caa agc ttg cct tgc ttt gaa gca tcc gac tgt aaa gaa tct      282
Cys Pro Gln Ser Leu Pro Cys Phe Glu Ala Ser Asp Cys Lys Glu Ser
            10                  15                  20 tca cct atg cct gtg att tgt ggg cct gaa gaa aac tat cca tcc ttg      330
Ser Pro Met Pro Val Ile Cys Gly Pro Glu Glu Asn Tyr Pro Ser Leu
        25                  30                  35 caa atg tct tct gct gag atg cct cac acg gag act gtc tct cct ctt      378
Gln Met Ser Ser Ala Glu Met Pro His Thr Glu Thr Val Ser Pro Leu
    40                  45                  50 ccc tcc tcc atg gat ctg ctt att cag gac agc cct gat tct tcc acc      426
Pro Ser Ser Met Asp Leu Leu Ile Gln Asp Ser Pro Asp Ser Ser Thr
55                  60                  65                  70 agt ccc aaa ggc aaa caa ccc act tct gca gag aat agt gtc gca aaa      474
Ser Pro Lys Gly Lys Gln Pro Thr Ser Ala Glu Asn Ser Val Ala Lys
                75                  80                  85 aag gaa gac aag gtc cca gtc aag aaa cag aag acc aga act gtg ttc      522
Lys Glu Asp Lys Val Pro Val Lys Lys Gln Lys Thr Arg Thr Val Phe
            90                  95                  100 tct tcc acc cag ctg tgt gta ctc aat gat aga ttt cag aga cag aaa      570
Ser Ser Thr Gln Leu Cys Val Leu Asn Asp Arg Phe Gln Arg Gln Lys
        105                 110                 115 tac ctc agc ctc cag cag atg caa gaa ctc tcc aac atc ctg aac ctc      618
Tyr Leu Ser Leu Gln Gln Met Gln Glu Leu Ser Asn Ile Leu Asn Leu
    120                 125                 130 agc tac aaa cag gtg aag acc tgg ttc cag aac cag aga atg aaa tct      666
Ser Tyr Lys Gln Val Lys Thr Trp Phe Gln Asn Gln Arg Met Lys Ser
135                 140                 145                 150
```

```
aag agg tgg cag aaa aac aac tgg ccg aag aat agc aat ggt gtg acg          714
Lys Arg Trp Gln Lys Asn Asn Trp Pro Lys Asn Ser Asn Gly Val Thr
            155                 160                 165 cag aag gcc tca gca cct acc tac ccc agc ctc tac tct tcc tac cac          762
Gln Lys Ala Ser Ala Pro Thr Tyr Pro Ser Leu Tyr Ser Ser Tyr His
            170                 175                 180 cag gga tgc ctg gtg aac ccg act ggg aac ctt cca atg tgg agc aac          810
Gln Gly Cys Leu Val Asn Pro Thr Gly Asn Leu Pro Met Trp Ser Asn
            185                 190                 195 cag acc tgg aac aat tca acc tgg agc aac cag acc cag aac atc cag          858
Gln Thr Trp Asn Asn Ser Thr Trp Ser Asn Gln Thr Gln Asn Ile Gln
            200                 205                 210 tcc tgg agc aac cac tcc tgg aac act cag acc tgg tgc acc caa tcc          906
Ser Trp Ser Asn His Ser Trp Asn Thr Gln Thr Trp Cys Thr Gln Ser
215                 220                 225                 230 tgg aac aat cag gcc tgg aac agt ccc ttc tat aac tgt gga gag gaa          954
Trp Asn Asn Gln Ala Trp Asn Ser Pro Phe Tyr Asn Cys Gly Glu Glu
                235                 240                 245 tct ctg cag tcc tgc atg cag ttc cag cca aat tct cct gcc agt gac         1002
Ser Leu Gln Ser Cys Met Gln Phe Gln Pro Asn Ser Pro Ala Ser Asp
            250                 255                 260 ttg gag gct gct ttg gaa gct gct ggg gaa ggc ctt aat gta ata cag         1050
Leu Glu Ala Ala Leu Glu Ala Ala Gly Glu Gly Leu Asn Val Ile Gln
            265                 270                 275 cag acc act agg tat ttt agt act cca caa acc atg gat tta ttc cta         1098
Gln Thr Thr Arg Tyr Phe Ser Thr Pro Gln Thr Met Asp Leu Phe Leu
            280                 285                 290 aac tac tcc atg aac atg caa cct gaa gac gtg tgaagatgag tgaaactgat       1151
Asn Tyr Ser Met Asn Met Gln Pro Glu Asp Val
295                 300                 305 attactcaat ttcagtctgg acactggctg aatccttcct ctcccctcct cccatccctc       1211
ataggatttt tcttgtttgg aaaccacgtg ttctggtttc catgatgcct atccagtcaa       1271
tctcatggag ggtggagtat ggttggagcc taatcagcga ggtttctttt tttttttttc       1331
ctattggatc ttcctggaga aaatactttt ttttttttt ttgagacgga gtcttgctct        1391
gtcgcccagg ctggagtgca gtggcgcggt cttggctcac tgcaagctcc gcctcccggg       1451
ttcacgccat tctcctgcct cagcctcccg agcagctggg actacaggcg cccgccacct       1511
cgcccggcta atattttgta ttttagtag agacagggtt tcactgtgtt agccaggatg       1571
gtctcgatct cctgaccttg tgatccgccc gcctcggcct ccctaacagc tgggattaca       1631
ggcgtgagcc accgcgccct gcctagaaaa gacattttaa taaccttggc tgctaaggac       1691
aacattgata gaagccgtct ctggctatag ataagtagat ctaatactag tttggatatc       1751
tttagggttt agaatctaac ctcaagaata agaaatacaa gtacgaattg gtgatgaaga       1811
tgtattcgta ttgtttggga ttgggaggct ttgcttattt ttttaaaact attgaggtaa       1871
agggttaagc tgtaacatac ttaattgatt tcttaccgtt tttggctctg ttttgctata       1931 tccccctaatt tgttggttgt gctaatcttt gtagaaagag gtcttgtatt tgctgcatcg      1991
taatgacatg agtactactt tagttggttt aagttcaaat gaatgaaaca aatatttttc      2051
ctttagttga tttttaccctg atttcaccga gtgtttcgat gagtaaatat acagcttaaa     2111
cat                                                                      2114

<210> SEQ ID NO 32
<211> LENGTH: 305
<212> TYPE: PRT
<213> ORGANISM: Homo sapiens
```

<400> SEQUENCE: 32

```
Met Ser Val Asp Pro Ala Cys Pro Gln Ser Leu Pro Cys Phe Glu Ala
1               5                   10                  15
Ser Asp Cys Lys Glu Ser Ser Pro Met Pro Val Ile Cys Gly Pro Glu
            20                  25                  30
Glu Asn Tyr Pro Ser Leu Gln Met Ser Ser Ala Glu Met Pro His Thr
        35                  40                  45
Glu Thr Val Ser Pro Leu Pro Ser Ser Met Asp Leu Leu Ile Gln Asp
    50                  55                  60
Ser Pro Asp Ser Ser Thr Ser Pro Lys Gly Lys Gln Pro Thr Ser Ala
65                  70                  75                  80
Glu Asn Ser Val Ala Lys Lys Glu Asp Lys Val Pro Val Lys Lys Gln
                85                  90                  95
Lys Thr Arg Thr Val Phe Ser Ser Thr Gln Leu Cys Val Leu Asn Asp
            100                 105                 110
Arg Phe Gln Arg Gln Lys Tyr Leu Ser Leu Gln Gln Met Gln Glu Leu
        115                 120                 125
Ser Asn Ile Leu Asn Leu Ser Tyr Lys Gln Val Lys Thr Trp Phe Gln
    130                 135                 140
Asn Gln Arg Met Lys Ser Lys Arg Trp Gln Lys Asn Asn Trp Pro Lys
145                 150                 155                 160
Asn Ser Asn Gly Val Thr Gln Lys Ala Ser Ala Pro Thr Tyr Pro Ser
                165                 170                 175
Leu Tyr Ser Ser Tyr His Gln Gly Cys Leu Val Asn Pro Thr Gly Asn
            180                 185                 190
Leu Pro Met Trp Ser Asn Gln Thr Trp Asn Asn Ser Thr Trp Ser Asn
        195                 200                 205
Gln Thr Gln Asn Ile Gln Ser Trp Ser Asn His Ser Trp Asn Thr Gln
    210                 215                 220
Thr Trp Cys Thr Gln Ser Trp Asn Asn Gln Ala Trp Asn Ser Pro Phe
225                 230                 235                 240
Tyr Asn Cys Gly Glu Glu Ser Leu Gln Ser Cys Met Gln Phe Gln Pro
                245                 250                 255
Asn Ser Pro Ala Ser Asp Leu Glu Ala Ala Leu Glu Ala Ala Gly Glu
            260                 265                 270
Gly Leu Asn Val Ile Gln Gln Thr Thr Arg Tyr Phe Ser Thr Pro Gln
        275                 280                 285
Thr Met Asp Leu Phe Leu Asn Tyr Ser Met Asn Met Gln Pro Glu Asp
    290                 295                 300
Val
305
```

<210> SEQ ID NO 33
<211> LENGTH: 1266
<212> TYPE: DNA
<213> ORGANISM: Homo sapiens
<220> FEATURE:
<221> NAME/KEY: CDS
<222> LOCATION: (252)..(950)

<400> SEQUENCE: 33

| | | |
|---|---|---|
| cgtgaggagg gaaggagaga tgggggacg tgggacaggg agaaacaac ataaatcata | 60 |
| tatatatagc atgcaaattg gaaggtgatc agcacacaat aggcattcaa taaatgttga | 120 |
| aataatgaca ccccactgtc tccttgccct caaatggtct cccctaacgt atccctgttt | 180 |
| gtccttgcttc ttctcttccc acttgcagag cctgctgccc acgtctcttc cctgagctgc | 240 |

```
ctgctggggt c atg gag ctg cca aca aag cct ggc acc ttc gac ctg ggc      290
            Met Glu Leu Pro Thr Lys Pro Gly Thr Phe Asp Leu Gly
            1               5                   10 ctg gcc aca tgg agc cct tcc ttc cag ggg gaa acc cac cgg gct cag        338
Leu Ala Thr Trp Ser Pro Ser Phe Gln Gly Glu Thr His Arg Ala Gln
15                  20                  25 gca cgc cgc agg gat gtt ggc agg cag ctg cct gag tac aag gct gtg        386
Ala Arg Arg Arg Asp Val Gly Arg Gln Leu Pro Glu Tyr Lys Ala Val
30                  35                  40                  45 gtg gtg ggc gcc agt ggc gtg ggc aag agt gcg ctg acc atc cag ctg        434
Val Val Gly Ala Ser Gly Val Gly Lys Ser Ala Leu Thr Ile Gln Leu
                50                  55                  60 aac cac cag tgc ttc gtg gag gac cac gac ccc acc atc cag gat tcc        482
Asn His Gln Cys Phe Val Glu Asp His Asp Pro Thr Ile Gln Asp Ser
65                  70                  75 tac tgg aag gag ttg acc ctg gac agt ggg gac tgc att ctg aat gtg        530
Tyr Trp Lys Glu Leu Thr Leu Asp Ser Gly Asp Cys Ile Leu Asn Val
            80                  85                  90 ctg gac aca gca ggg cag gcc atc cat agg gcc ctg cgt gac cag tgc        578
Leu Asp Thr Ala Gly Gln Ala Ile His Arg Ala Leu Arg Asp Gln Cys
95                  100                 105 ctg gct gtc tgt gat ggt gtg ctg ggc gtc ttc gct ctc gat gac ccc        626
Leu Ala Val Cys Asp Gly Val Leu Gly Val Phe Ala Leu Asp Asp Pro
110                 115                 120                 125 tcg tct ctg atc cag ctg cag cag ata tgg gcc acc tgg ggc cct cac        674
Ser Ser Leu Ile Gln Leu Gln Gln Ile Trp Ala Thr Trp Gly Pro His
                130                 135                 140 ccc gcc cag ccc ctt gtc ctc gtg ggc aac aag tgt gac ctt gtg acc        722
Pro Ala Gln Pro Leu Val Leu Val Gly Asn Lys Cys Asp Leu Val Thr
            145                 150                 155 act gct gga gat gct cat gcc gct gct gca gcc ctc gca cac agc tgg        770
Thr Ala Gly Asp Ala His Ala Ala Ala Ala Leu Ala His Ser Trp
                160                 165                 170 ggg gcc cac ttc gtg gag acc tcg gcc aaa aca cgg caa ggc gtg gag        818
Gly Ala His Phe Val Glu Thr Ser Ala Lys Thr Arg Gln Gly Val Glu
175                 180                 185 gag gcc ttt tcc ctg ctg gtc cat gag atc cag agg gtc cag gag gcc        866
Glu Ala Phe Ser Leu Leu Val His Glu Ile Gln Arg Val Gln Glu Ala
190                 195                 200                 205 atg gcg aag gag ccc atg gca agg tcc tgt agg gag aag acc cgg cac        914
Met Ala Lys Glu Pro Met Ala Arg Ser Cys Arg Glu Lys Thr Arg His
                210                 215                 220 cag aag gcc acc tgc cac tgt ggc tgc tct gtg gcc tgaaggtctt            960
Gln Lys Ala Thr Cys His Cys Gly Cys Ser Val Ala
            225                 230 ggccaagaaa tgtagacctt tccccaggcc agggtgattg ttcatttgac atgagacccc    1020
tgaggcaact agctttgagg gacacatcag gtatactagg gaaagatgga catctctctt    1080
gttttcactt ggtgagggc ttttggtaa catgggagtg cctaatgttg cttttgttat      1140
gtcaagttga aagatttgt gcaaaattaa ataaatggtg ttttgggttt caaagctgcc     1200
tccatgccga gtgttgtgtg ggtgggagtg agactgggta gaatgttact tgagttgtga    1260
gaattc                                                                1266
```

<210> SEQ ID NO 34
<211> LENGTH: 233
<212> TYPE: PRT
<213> ORGANISM: Homo sapiens

<400> SEQUENCE: 34

```
Met Glu Leu Pro Thr Lys Pro Gly Thr Phe Asp Leu Gly Leu Ala Thr
1               5                   10                  15

Trp Ser Pro Ser Phe Gln Gly Glu Thr His Arg Ala Gln Ala Arg Arg
            20                  25                  30

Arg Asp Val Gly Arg Gln Leu Pro Glu Tyr Lys Ala Val Val Gly
            35                  40                  45

Ala Ser Gly Val Gly Lys Ser Ala Leu Thr Ile Gln Leu Asn His Gln
        50                  55                  60

Cys Phe Val Glu Asp His Asp Pro Thr Ile Gln Asp Ser Tyr Trp Lys
65                  70                  75                  80

Glu Leu Thr Leu Asp Ser Gly Asp Cys Ile Leu Asn Val Leu Asp Thr
                85                  90                  95

Ala Gly Gln Ala Ile His Arg Ala Leu Arg Asp Gln Cys Leu Ala Val
            100                 105                 110

Cys Asp Gly Val Leu Gly Val Phe Ala Leu Asp Asp Pro Ser Ser Leu
            115                 120                 125

Ile Gln Leu Gln Gln Ile Trp Ala Thr Trp Gly Pro His Pro Ala Gln
130                 135                 140

Pro Leu Val Leu Val Gly Asn Lys Cys Asp Leu Val Thr Thr Ala Gly
145                 150                 155                 160

Asp Ala His Ala Ala Ala Ala Leu Ala His Ser Trp Gly Ala His
                165                 170                 175

Phe Val Glu Thr Ser Ala Lys Thr Arg Gln Gly Val Glu Glu Ala Phe
            180                 185                 190

Ser Leu Leu Val His Glu Ile Gln Arg Val Gln Glu Ala Met Ala Lys
            195                 200                 205

Glu Pro Met Ala Arg Ser Cys Arg Glu Lys Thr Arg His Gln Lys Ala
        210                 215                 220

Thr Cys His Cys Gly Cys Ser Val Ala
225                 230

<210> SEQ ID NO 35
<211> LENGTH: 1705
<212> TYPE: DNA
<213> ORGANISM: Homo sapiens
<220> FEATURE:
<221> NAME/KEY: CDS
<222> LOCATION: (485)..(1645)

<400> SEQUENCE: 35
cccatctcca cccctcccct gaaccccact ccccactgag gtccccaaac cccacccctc      60
actccaccct gagggcccca tcctctgaac cccaatcccc cagccccact gagctcttaa     120
ccctccccac ctgagggttc cctttccctg cccgtccccc agcttcctag ctccccaccc     180
caagtgaccc cccgcagctc ctcgcccctc ccactgcaaa ccggcactga agggctgccc     240 cgccccgcc  cctccccgcc ccgcgggac  acgcccagat tctttgcccc catagcctgg     300
tgacctctgg ccaccgctg  tcccaggtgg gcctggatcc ttccagctca ttctttgcct     360
gcgccgtccc tcgttccatg gcccagtcct ccccggggac cctgagcctg aagcccgg       420 accactggaa ccttgaaccc accagctggc tgtacccgga gcgtggcag  cagccctcat    480 cccc atg gcg gcc atc cca gcc ctg gac cca gag gcc gag ccc agc atg    529
     Met Ala Ala Ile Pro Ala Leu Asp Pro Glu Ala Glu Pro Ser Met
     1               5                   10                  15 gac gtg att ttg gtg gga tcc agt gag ctc tca agc tcc gtt tca ccc    577
Asp Val Ile Leu Val Gly Ser Ser Glu Leu Ser Ser Ser Val Ser Pro
            20                  25                  30
```

```
ggg aca ggc aga gat ctt att gca tat gaa gtc aag gct aac cag cga      625
Gly Thr Gly Arg Asp Leu Ile Ala Tyr Glu Val Lys Ala Asn Gln Arg
            35                  40                  45 aat ata gaa gac atc tgc atc tgc tgc gga agt ctc cag gtt cac aca      673
Asn Ile Glu Asp Ile Cys Ile Cys Cys Gly Ser Leu Gln Val His Thr
    50                  55                  60 cag cac cct ctg ttt gag gga ggg atc tgc gcc cca tgt aag gac aag      721
Gln His Pro Leu Phe Glu Gly Gly Ile Cys Ala Pro Cys Lys Asp Lys
65                  70                  75 ttc ctg gat gcc ctc ttc ctg tac gac gat gac ggg tac caa tcc tac      769
Phe Leu Asp Ala Leu Phe Leu Tyr Asp Asp Asp Gly Tyr Gln Ser Tyr
80                  85                  90                  95 tgc tcc atc tgc tgc tcc gga gag acg ctg ctc atc tgc gga aac cct      817
Cys Ser Ile Cys Cys Ser Gly Glu Thr Leu Leu Ile Cys Gly Asn Pro
                100                 105                 110 gat tgc acc cga tgc tac tgc ttc gag tgt gtg gat agc ctg gtc ggc      865
Asp Cys Thr Arg Cys Tyr Cys Phe Glu Cys Val Asp Ser Leu Val Gly
            115                 120                 125 ccc ggg acc tcg ggg aag gtg cac gcc atg agc aac tgg gtg tgc tac      913
Pro Gly Thr Ser Gly Lys Val His Ala Met Ser Asn Trp Val Cys Tyr
        130                 135                 140 ctg tgc ctg ccg tcc tcc cga agc ggg ctg ctg cag cgt cgg agg aag      961
Leu Cys Leu Pro Ser Ser Arg Ser Gly Leu Leu Gln Arg Arg Arg Lys
145                 150                 155 tgg cgc agc cag ctc aag gcc ttc tac gac cga gag tcg gag aat ccc     1009
Trp Arg Ser Gln Leu Lys Ala Phe Tyr Asp Arg Glu Ser Glu Asn Pro
160                 165                 170                 175 ctt gag atg ttc gaa acc gtg cct gtg tgg agg aga cag cca gtc cgg     1057
Leu Glu Met Phe Glu Thr Val Pro Val Trp Arg Arg Gln Pro Val Arg
                180                 185                 190 gtg ctg tcc ctt ttt gaa gac atc aag aaa gag ctg acg agt ttg ggc     1105
Val Leu Ser Leu Phe Glu Asp Ile Lys Lys Glu Leu Thr Ser Leu Gly
            195                 200                 205 ttt ttg gaa agt ggt tct gac ccg gga caa ctg aag cat gtg gtt gat     1153
Phe Leu Glu Ser Gly Ser Asp Pro Gly Gln Leu Lys His Val Val Asp
        210                 215                 220 gtc aca gac aca gtg agg aag gat gtg gag gag tgg gga ccc ttc gat     1201
Val Thr Asp Thr Val Arg Lys Asp Val Glu Glu Trp Gly Pro Phe Asp
225                 230                 235 ctt gtg tac ggc gcc aca gct ccc ctg ggc cac acc tgt gac cgt cct     1249
Leu Val Tyr Gly Ala Thr Ala Pro Leu Gly His Thr Cys Asp Arg Pro
240                 245                 250                 255 ccc agc tgg tac ctg ttc cag ttc cac cgg ttc ctg cag tac gca cgg     1297
Pro Ser Trp Tyr Leu Phe Gln Phe His Arg Phe Leu Gln Tyr Ala Arg
                260                 265                 270 ccc aag cca ggc agc ccc agg ccc ttc ttc tgg atg ttc gtg gac aat     1345
Pro Lys Pro Gly Ser Pro Arg Pro Phe Phe Trp Met Phe Val Asp Asn
            275                 280                 285 ctg gtg ctg aac aag gaa gac ctg gac gtc gca tct cgc ttc ctg gag     1393
Leu Val Leu Asn Lys Glu Asp Leu Asp Val Ala Ser Arg Phe Leu Glu
        290                 295                 300 atg gag cca gtc acc atc cca gat gtc cac ggc gga tcc ttg cag aat     1441
Met Glu Pro Val Thr Ile Pro Asp Val His Gly Gly Ser Leu Gln Asn
305                 310                 315 gct gtc cgc gtg tgg agc aac atc cca gcc ata agg agc agc agg cac     1489
Ala Val Arg Val Trp Ser Asn Ile Pro Ala Ile Arg Ser Ser Arg His
320                 325                 330                 335 tgg gct ctg gtt tcg gaa gaa gaa ttg tcc ctg ctg gcc cag aac aag     1537
Trp Ala Leu Val Ser Glu Glu Glu Leu Ser Leu Leu Ala Gln Asn Lys
                340                 345                 350
```

```
cag agc tcg aag ctc gcg gcc aag tgg ccc acc aag ctg gtg aag aac    1585
Gln Ser Ser Lys Leu Ala Ala Lys Trp Pro Thr Lys Leu Val Lys Asn
        355                 360                 365 tgc ttt ctc ccc cta aga gaa tat ttc aag tat ttt tca aca gaa ctc    1633
Cys Phe Leu Pro Leu Arg Glu Tyr Phe Lys Tyr Phe Ser Thr Glu Leu
370                 375                 380 act tcc tct tta taaatgagtc actatactgt gaagaaaaag actttcccta        1685
Thr Ser Ser Leu
    385 gaacaaaggc aactttcctc                                              1705

<210> SEQ ID NO 36
<211> LENGTH: 387
<212> TYPE: PRT
<213> ORGANISM: Homo sapiens

<400> SEQUENCE: 36

Met Ala Ala Ile Pro Ala Leu Asp Pro Glu Ala Glu Pro Ser Met Asp
1               5                   10                  15

Val Ile Leu Val Gly Ser Ser Glu Leu Ser Ser Val Ser Pro Gly
            20                  25                  30

Thr Gly Arg Asp Leu Ile Ala Tyr Glu Val Lys Ala Asn Gln Arg Asn
        35                  40                  45

Ile Glu Asp Ile Cys Ile Cys Cys Gly Ser Leu Gln Val His Thr Gln
    50                  55                  60

His Pro Leu Phe Glu Gly Gly Ile Cys Ala Pro Cys Lys Asp Lys Phe
65                  70                  75                  80

Leu Asp Ala Leu Phe Leu Tyr Asp Asp Gly Tyr Gln Ser Tyr Cys
                85                  90                  95

Ser Ile Cys Cys Ser Gly Glu Thr Leu Leu Ile Cys Gly Asn Pro Asp
                100                 105                 110

Cys Thr Arg Cys Tyr Cys Phe Glu Cys Val Asp Ser Leu Val Gly Pro
            115                 120                 125

Gly Thr Ser Gly Lys Val His Ala Met Ser Asn Trp Val Cys Tyr Leu
        130                 135                 140

Cys Leu Pro Ser Ser Arg Ser Gly Leu Leu Gln Arg Arg Lys Trp
145                 150                 155                 160

Arg Ser Gln Leu Lys Ala Phe Tyr Asp Arg Glu Ser Glu Asn Pro Leu
                165                 170                 175

Glu Met Phe Glu Thr Val Pro Val Trp Arg Arg Gln Pro Val Arg Val
                180                 185                 190

Leu Ser Leu Phe Glu Asp Ile Lys Lys Glu Leu Thr Ser Leu Gly Phe
        195                 200                 205

Leu Glu Ser Gly Ser Asp Pro Gly Gln Leu Lys His Val Val Asp Val
    210                 215                 220

Thr Asp Thr Val Arg Lys Asp Val Glu Trp Gly Pro Phe Asp Leu
225                 230                 235                 240

Val Tyr Gly Ala Thr Ala Pro Leu Gly His Thr Cys Asp Arg Pro Pro
                245                 250                 255

Ser Trp Tyr Leu Phe Gln Phe His Arg Phe Leu Gln Tyr Ala Arg Pro
                260                 265                 270

Lys Pro Gly Ser Pro Arg Pro Phe Phe Trp Met Phe Val Asp Asn Leu
        275                 280                 285

Val Leu Asn Lys Glu Asp Leu Asp Val Ala Ser Arg Phe Leu Glu Met
    290                 295                 300
```

```
Glu Pro Val Thr Ile Pro Asp Val His Gly Gly Ser Leu Gln Asn Ala
305                 310                 315                 320

Val Arg Val Trp Ser Asn Ile Pro Ala Ile Arg Ser Ser Arg His Trp
                325                 330                 335

Ala Leu Val Ser Glu Glu Leu Ser Leu Leu Ala Gln Asn Lys Gln
                340                 345                 350

Ser Ser Lys Leu Ala Ala Lys Trp Pro Thr Lys Leu Val Lys Asn Cys
            355                 360                 365

Phe Leu Pro Leu Arg Glu Tyr Phe Lys Tyr Phe Ser Thr Glu Leu Thr
370                 375                 380

Ser Ser Leu
385

<210> SEQ ID NO 37
<211> LENGTH: 1301
<212> TYPE: DNA
<213> ORGANISM: Homo sapiens
<220> FEATURE:
<221> NAME/KEY: CDS
<222> LOCATION: (97)..(1167)

<400> SEQUENCE: 37
ttacagattg aagatccagg ttgcttctgg gttattataa aagggtgtag tccctttta       60 gatcatgatg tcgattatca aaattaaat agtgcc atg aat gac ttc tac aac       114
                                       Met Asn Asp Phe Tyr Asn
                                        1               5 agc acg tgt caa gat ata gaa ata aaa ccc tta aca ttg gaa gaa gga       162
Ser Thr Cys Gln Asp Ile Glu Ile Lys Pro Leu Thr Leu Glu Glu Gly
         10                  15                  20 cag gtg tgt gtg gtc tat tgt gag gag cta aag tgc tgg tgc agg gcc       210
Gln Val Cys Val Val Tyr Cys Glu Glu Leu Lys Cys Trp Cys Arg Ala
     25                  30                  35 att gtc aaa tca att acg tct tcc gca gac cag tac ctg gca gaa tgt       258
Ile Val Lys Ser Ile Thr Ser Ser Ala Asp Gln Tyr Leu Ala Glu Cys
 40                  45                  50 ttc ctt gtg gac ttt gcc aag aac att cca gtc aaa tct aaa agc atc       306
Phe Leu Val Asp Phe Ala Lys Asn Ile Pro Val Lys Ser Lys Ser Ile
55                  60                  65                  70 cga gtt gta gta gaa tcg ttt atg cag ctt ccc tat aga gca aaa aaa       354
Arg Val Val Val Glu Ser Phe Met Gln Leu Pro Tyr Arg Ala Lys Lys
                 75                  80                  85 ttc agc ctg tac tgc aca aag cct gtc aca tta cac att gac ttc tgc       402
Phe Ser Leu Tyr Cys Thr Lys Pro Val Thr Leu His Ile Asp Phe Cys
             90                  95                 100 cga gac agt act gac att gtg cct gcc aag aag tgg gac aat gca gct       450
Arg Asp Ser Thr Asp Ile Val Pro Ala Lys Lys Trp Asp Asn Ala Ala
        105                 110                 115 att cag tac ttt cag aac ctt ctg aaa gca act acc cag gtg gaa gcc       498
Ile Gln Tyr Phe Gln Asn Leu Leu Lys Ala Thr Thr Gln Val Glu Ala
    120                 125                 130 aga tta tgt gct gtg gaa gaa gat aca ttt gag gtt tac ctt tat gta       546
Arg Leu Cys Ala Val Glu Glu Asp Thr Phe Glu Val Tyr Leu Tyr Val
135                 140                 145                 150 act ata aaa gat gaa aaa gtt tgt gtt aat gat gat ctt gtt gca aag       594
Thr Ile Lys Asp Glu Lys Val Cys Val Asn Asp Asp Leu Val Ala Lys
                155                 160                 165 aac tat gct tgt tat atg tca cct aca aag aat aaa aac ctt gat tat       642
Asn Tyr Ala Cys Tyr Met Ser Pro Thr Lys Asn Lys Asn Leu Asp Tyr
            170                 175                 180 tta gaa aaa cca aga ttg aat ata aaa tca gca ccc tcc ttc aat aaa       690
```

-continued

```
              Leu Glu Lys Pro Arg Leu Asn Ile Lys Ser Ala Pro Ser Phe Asn Lys
                          185                 190                 195 ctc aat cca gca ctt aca ctc tgg cca atg ttt ttg caa gga aaa gat       738
Leu Asn Pro Ala Leu Thr Leu Trp Pro Met Phe Leu Gln Gly Lys Asp
    200                 205                 210 gtt caa gga atg gaa gat tca cat ggt gta aat ttt ccg gca caa tct       786
Val Gln Gly Met Glu Asp Ser His Gly Val Asn Phe Pro Ala Gln Ser
215                 220                 225                 230 ctg caa cat aca tgg tgc aag ggt att gtc ggt gac ctc agg cca aca       834
Leu Gln His Thr Trp Cys Lys Gly Ile Val Gly Asp Leu Arg Pro Thr
                235                 240                 245 gcc aca gca cag gac aaa gct gta aaa tgt aat atg gat tca ttg aga       882
Ala Thr Ala Gln Asp Lys Ala Val Lys Cys Asn Met Asp Ser Leu Arg
            250                 255                 260 gat tca cct aaa gac aaa tct gaa aag aaa cac cat tgc atc tct tta       930
Asp Ser Pro Lys Asp Lys Ser Glu Lys Lys His His Cys Ile Ser Leu
        265                 270                 275 aaa gat aca aat aag cgt gtt gaa tcc tca gtg tac tgg cca gca aaa       978
Lys Asp Thr Asn Lys Arg Val Glu Ser Ser Val Tyr Trp Pro Ala Lys
    280                 285                 290 aga ggc ata acc ata tat gct gat cca gat gta cca gaa gca agt gct      1026
Arg Gly Ile Thr Ile Tyr Ala Asp Pro Asp Val Pro Glu Ala Ser Ala
295                 300                 305                 310 tta agt cag aag tca aat gag aaa cct ctt aga ttg act gag aag aaa      1074
Leu Ser Gln Lys Ser Asn Glu Lys Pro Leu Arg Leu Thr Glu Lys Lys
                315                 320                 325 gaa tat gat gag aag aat agc tgt gtg aaa tta ctg cag ttt tta aat      1122
Glu Tyr Asp Glu Lys Asn Ser Cys Val Lys Leu Leu Gln Phe Leu Asn
            330                 335                 340 cct gat cct ttg aga gct gac gga atc tct gat ctc cag cag act          1167
Pro Asp Pro Leu Arg Ala Asp Gly Ile Ser Asp Leu Gln Gln Thr
        345                 350                 355 tgagattaga agagaaactc cttagatggg ggacttaacc tgaagacatc cttttagaaa    1227
cgatcgaatg gattgttgct tctgagaaat tgttccttgt ttttggata ataaacgatc     1287 ttcctttttgg taaa                                                     1301

<210> SEQ ID NO 38
<211> LENGTH: 357
<212> TYPE: PRT
<213> ORGANISM: Homo sapiens

<400> SEQUENCE: 38

Met Asn Asp Phe Tyr Asn Ser Thr Cys Gln Asp Ile Glu Ile Lys Pro
1               5                   10                  15

Leu Thr Leu Glu Glu Gly Gln Val Cys Val Val Tyr Cys Glu Glu Leu
            20                  25                  30

Lys Cys Trp Cys Arg Ala Ile Val Lys Ser Ile Thr Ser Ser Ala Asp
        35                  40                  45

Gln Tyr Leu Ala Glu Cys Phe Leu Val Asp Phe Ala Lys Asn Ile Pro
    50                  55                  60

Val Lys Ser Lys Ser Ile Arg Val Val Glu Ser Phe Met Gln Leu
65                  70                  75                  80

Pro Tyr Arg Ala Lys Lys Phe Ser Leu Tyr Cys Thr Lys Pro Val Thr
            85                  90                  95

Leu His Ile Asp Phe Cys Arg Asp Ser Thr Asp Ile Val Pro Ala Lys
        100                 105                 110

Lys Trp Asp Asn Ala Ala Ile Gln Tyr Phe Gln Asn Leu Leu Lys Ala
    115                 120                 125
```

Thr Thr Gln Val Glu Ala Arg Leu Cys Ala Val Glu Glu Asp Thr Phe
    130                 135                 140

Glu Val Tyr Leu Tyr Val Thr Ile Lys Asp Glu Lys Val Cys Val Asn
145                 150                 155                 160

Asp Asp Leu Val Ala Lys Asn Tyr Ala Cys Tyr Met Ser Pro Thr Lys
                    165                 170                 175

Asn Lys Asn Leu Asp Tyr Leu Glu Lys Pro Arg Leu Asn Ile Lys Ser
                180                 185                 190

Ala Pro Ser Phe Asn Lys Leu Asn Pro Ala Leu Thr Leu Trp Pro Met
            195                 200                 205

Phe Leu Gln Gly Lys Asp Val Gln Gly Met Glu Asp Ser His Gly Val
210                 215                 220

Asn Phe Pro Ala Gln Ser Leu Gln His Thr Trp Cys Lys Gly Ile Val
225                 230                 235                 240

Gly Asp Leu Arg Pro Thr Ala Thr Ala Gln Asp Lys Ala Val Lys Cys
                    245                 250                 255

Asn Met Asp Ser Leu Arg Asp Ser Pro Lys Asp Lys Ser Glu Lys Lys
                260                 265                 270

His His Cys Ile Ser Leu Lys Asp Thr Asn Lys Arg Val Glu Ser Ser
            275                 280                 285

Val Tyr Trp Pro Ala Lys Arg Gly Ile Thr Ile Tyr Ala Asp Pro Asp
290                 295                 300

Val Pro Glu Ala Ser Ala Leu Ser Gln Lys Ser Asn Glu Lys Pro Leu
305                 310                 315                 320

Arg Leu Thr Glu Lys Lys Glu Tyr Asp Glu Lys Asn Ser Cys Val Lys
                    325                 330                 335

Leu Leu Gln Phe Leu Asn Pro Pro Leu Arg Ala Gly Ile Ser
                340                 345                 350

Asp Leu Gln Gln Thr
            355

<210> SEQ ID NO 39
<211> LENGTH: 1371
<212> TYPE: DNA
<213> ORGANISM: Homo sapiens
<220> FEATURE:
<221> NAME/KEY: CDS
<222> LOCATION: (43)..(1122)

<400> SEQUENCE: 39
ctcatttcac caggcccccg gcttggggcg ccttccttcc cc atg gcg gga cac      54
                                                Met Ala Gly His
                                                  1 ctg gct tcg gat ttc gcc ttc tcg ccc cct cca ggt ggt gga ggt gat    102
Leu Ala Ser Asp Phe Ala Phe Ser Pro Pro Pro Gly Gly Gly Gly Asp
  5                  10                  15                  20 ggg cca ggg ggg ccg gag ccg ggc tgg gtt gat cct cgg acc tgg cta    150
Gly Pro Gly Gly Pro Glu Pro Gly Trp Val Asp Pro Arg Thr Trp Leu
                25                  30                  35 agc ttc caa ggc cct cct gga ggg cca gga atc ggg ccg ggg gtt ggg    198
Ser Phe Gln Gly Pro Pro Gly Gly Pro Gly Ile Gly Pro Gly Val Gly
            40                  45                  50 cca ggc tct gag gtg tgg ggg att ccc cca tgc ccc ccg tat gag        246
Pro Gly Ser Glu Val Trp Gly Ile Pro Pro Cys Pro Pro Tyr Glu
        55                  60                  65 ttc tgt ggg ggg atg gcg tac tgt ggg ccc cag gtt gga gtg ggg cta    294
Phe Cys Gly Gly Met Ala Tyr Cys Gly Pro Gln Val Gly Val Gly Leu
    70                  75                  80

```
gtg ccc caa ggc ggc ttg gag acc tct cag cct gag ggc gaa gca gga      342
Val Pro Gln Gly Gly Leu Glu Thr Ser Gln Pro Glu Gly Glu Ala Gly
 85                  90                  95                 100 gtc ggg gtg gag agc aac tcc gat ggg gcc tcc ccg gag ccc tgc acc      390
Val Gly Val Glu Ser Asn Ser Asp Gly Ala Ser Pro Glu Pro Cys Thr
                105                 110                 115 gtc acc cct ggt gcc gtg aag ctg gag aag gag aag ctg gag caa aac      438
Val Thr Pro Gly Ala Val Lys Leu Glu Lys Glu Lys Leu Glu Gln Asn
            120                 125                 130 ccg gag gag tcc cag gac atc aaa gct ctg cag aaa gaa ctc gag caa      486
Pro Glu Glu Ser Gln Asp Ile Lys Ala Leu Gln Lys Glu Leu Glu Gln
        135                 140                 145 ttt gcc aag ctc ctg aag cag aag agg atc acc ctg gga tat aca cag      534
Phe Ala Lys Leu Leu Lys Gln Lys Arg Ile Thr Leu Gly Tyr Thr Gln
    150                 155                 160 gcc gat gtg ggg ctc acc ctg ggg gtt cta ttt ggg aag gta ttc agc      582
Ala Asp Val Gly Leu Thr Leu Gly Val Leu Phe Gly Lys Val Phe Ser
165                 170                 175                 180 caa acg acc atc tgc cgc ttt gag gct ctg cag ctt agc ttc aag aac      630
Gln Thr Thr Ile Cys Arg Phe Glu Ala Leu Gln Leu Ser Phe Lys Asn
                185                 190                 195 atg tgt aag ctg cgg ccc ttg ctg cag aag tgg gtg gag gaa gct gac      678
Met Cys Lys Leu Arg Pro Leu Leu Gln Lys Trp Val Glu Glu Ala Asp
            200                 205                 210 aac aat gaa aat ctt cag gag ata tgc aaa gca gaa acc ctc gtg cag      726
Asn Asn Glu Asn Leu Gln Glu Ile Cys Lys Ala Glu Thr Leu Val Gln
        215                 220                 225 gcc cga aag aga aag cga acc agt atc gag aac cga gtg aga ggc aac      774
Ala Arg Lys Arg Lys Arg Thr Ser Ile Glu Asn Arg Val Arg Gly Asn
    230                 235                 240 ctg gag aat ttg ttc ctg cag tgc ccg aaa ccc aca ctg cag cag atc      822
Leu Glu Asn Leu Phe Leu Gln Cys Pro Lys Pro Thr Leu Gln Gln Ile
245                 250                 255                 260 agc cac atc gcc cag cag ctt ggc ctc gag aag gat gtg gtc cga gtg      870
Ser His Ile Ala Gln Gln Leu Gly Leu Glu Lys Asp Val Val Arg Val
                265                 270                 275 tgg ttc tgt aac cgg cgc cag aag ggc aag cga tca agc agc gac tat      918
Trp Phe Cys Asn Arg Arg Gln Lys Gly Lys Arg Ser Ser Ser Asp Tyr
            280                 285                 290 gca caa cga gag gat ttt gag gct gct ggg tct cct ttc tca ggg gga      966
Ala Gln Arg Glu Asp Phe Glu Ala Ala Gly Ser Pro Phe Ser Gly Gly
        295                 300                 305 cca gtg tcc ttt cct ctg gcc cca ggg ccc cat ttt ggt acc cca ggc     1014
Pro Val Ser Phe Pro Leu Ala Pro Gly Pro His Phe Gly Thr Pro Gly
    310                 315                 320 tat ggg agc cct cac ttc act gca ctg tac tcc tcg gtc cct ttc cct     1062
Tyr Gly Ser Pro His Phe Thr Ala Leu Tyr Ser Ser Val Pro Phe Pro
325                 330                 335                 340 gag ggg gaa gcc ttt ccc cct gtc tct gtc acc act ctg ggc tct ccc     1110
Glu Gly Glu Ala Phe Pro Pro Val Ser Val Thr Thr Leu Gly Ser Pro
                345                 350                 355 atg cat tca aac tgaggtgcct gcccttctag gaatggggga caggggagg          1162
Met His Ser Asn
            360 ggaggagcta gggaaagaaa acctggagtt tgtgccaggg ttttggatt aagttcttca    1222 ttcactaagg aaggaattgg gaacacaaag ggtgggggca ggggagtttg gggcaactgg   1282 ttggagggaa ggtgaagttc aatgatgctc ttgattttaa tcccacatca tgtatcactt   1342 ttttcttaaa taaagaagct tgggacaca                                     1371
```

<210> SEQ ID NO 40
<211> LENGTH: 360
<212> TYPE: PRT
<213> ORGANISM: Homo sapiens

<400> SEQUENCE: 40

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 41

```
<211> LENGTH: 1280
<212> TYPE: DNA
<213> ORGANISM: Mus musculus
<220> FEATURE:
<221> NAME/KEY: CDS
<222> LOCATION: (122)..(1219)

<400> SEQUENCE: 41 tgagggggctg agaagagagc aattcacact tgattagctc ccaggctcct gaattgagca      60
gaggaggcta daccgctgag ctgcgcaccc cagaggctgc tctaccctgg ctcagacgac     120 c atg cag cct tat caa cgg ctt ctg gcg ctt ggc ttc ctt ctg tta acc     169
  Met Gln Pro Tyr Gln Arg Leu Leu Ala Leu Gly Phe Leu Leu Leu Thr
  1               5                   10                  15 ctg ccc tgg ggc cag aca tcc gag ttt caa gac tct gac ctt ttg cag       217
Leu Pro Trp Gly Gln Thr Ser Glu Phe Gln Asp Ser Asp Leu Leu Gln
            20                  25                  30 ttt ctg gga tta gag aaa gcg cct tca cct cac agg ttc caa cct gtg       265
Phe Leu Gly Leu Glu Lys Ala Pro Ser Pro His Arg Phe Gln Pro Val
        35                  40                  45 cct cgc gtc tta agg aaa atc atc cgg gct cga gaa gcc gct gca gcc       313
Pro Arg Val Leu Arg Lys Ile Ile Arg Ala Arg Glu Ala Ala Ala Ala
50                  55                  60 agt ggg gcc tcg cag gac tta tgc tac gtg aag gag ctg ggt gtt cgt       361
Ser Gly Ala Ser Gln Asp Leu Cys Tyr Val Lys Glu Leu Gly Val Arg
65                  70                  75                  80 ggg aac ctg ctt cag ctt ctc cca gac cag ggt ttt tct aat aca           409
Gly Asn Leu Leu Gln Leu Leu Pro Asp Gln Gly Phe Phe Leu Asn Thr
            85                  90                  95 cag aaa cct ttc caa gat ggc tcc tgt ctc cag aag gtc ctc tat ttt       457
Gln Lys Pro Phe Gln Asp Gly Ser Cys Leu Gln Lys Val Leu Tyr Phe
        100                 105                 110 aac ttg tct gcc atc aaa gaa aag gca aag ttg acc atg gcc cag ctg       505
Asn Leu Ser Ala Ile Lys Glu Lys Ala Lys Leu Thr Met Ala Gln Leu
    115                 120                 125 act cta gac ttg ggg ccc agg tcc tac tat aac ctg cga cca gag ctg       553
Thr Leu Asp Leu Gly Pro Arg Ser Tyr Tyr Asn Leu Arg Pro Glu Leu
130                 135                 140 gtg gtt gct ctg tct gtg gtt cag gac cgg ggc gtg tgg ggg cga tcc       601
Val Val Ala Leu Ser Val Val Gln Asp Arg Gly Val Trp Gly Arg Ser
145                 150                 155                 160 cac cct aag gtg ggc aga ttg ctt ttt ctg cgg tct gtc cct ggg cct       649
His Pro Lys Val Gly Arg Leu Leu Phe Leu Arg Ser Val Pro Gly Pro
            165                 170                 175 caa ggt cag ctc cag ttc aac ctg cag ggt gcg ctt aag gat tgg agc       697
Gln Gly Gln Leu Gln Phe Asn Leu Gln Gly Ala Leu Lys Asp Trp Ser
        180                 185                 190 agc aac cga ctg aag aat ttg gac tta cac tta gag att ttg gtc aaa       745
Ser Asn Arg Leu Lys Asn Leu Asp Leu His Leu Glu Ile Leu Val Lys
    195                 200                 205 gag gac aga tac tcc agg gta act gtc cag ccc gag aac ccc tgt gac       793
Glu Asp Arg Tyr Ser Arg Val Thr Val Gln Pro Glu Asn Pro Cys Asp
210                 215                 220 ccg ctg ctc cgc tct cta cat gcc tcg ctg ctg gta acc ctc aat           841
Pro Leu Leu Arg Ser Leu His Ala Ser Leu Leu Val Thr Leu Asn
225                 230                 235                 240 cct aaa cac tgt cat cct tct tcc aga aaa agg agg gcg gcc atc tct       889
Pro Lys His Cys His Pro Ser Ser Arg Lys Arg Arg Ala Ala Ile Ser
            245                 250                 255 gtc ccc aag ggt ttc tgt agg aac ttc tgc cac cgt cat cag ctg ttc       937
Val Pro Lys Gly Phe Cys Arg Asn Phe Cys His Arg His Gln Leu Phe
        260                 265                 270
```

```
atc aac ttc cag gac ctg ggt tgg cac aag tgg gtc atc gcc cct aag      985
Ile Asn Phe Gln Asp Leu Gly Trp His Lys Trp Val Ile Ala Pro Lys
            275                 280                 285 ggg ttc atg gca aat tac tgt cat gga gag tgc ccc ttc tca atg acc     1033
Gly Phe Met Ala Asn Tyr Cys His Gly Glu Cys Pro Phe Ser Met Thr
        290                 295                 300 acg tat tta aat agt tcc aat tat gct ttc atg cag gct ctg atg cat     1081
Thr Tyr Leu Asn Ser Ser Asn Tyr Ala Phe Met Gln Ala Leu Met His
305                 310                 315                 320 atg gct gac ccc aag gtc ccc aag gct gtc tgt gtc ccc acc aag ctc     1129
Met Ala Asp Pro Lys Val Pro Lys Ala Val Cys Val Pro Thr Lys Leu
                325                 330                 335 tcg ccc atc tcc atg ctc tat cag gat agt gat aag aac gtc att ctc     1177
Ser Pro Ile Ser Met Leu Tyr Gln Asp Ser Asp Lys Asn Val Ile Leu
            340                 345                 350 cga cat tat gaa gac atg gta gtc gat gag tgt ggg tgt ggg             1219
Arg His Tyr Glu Asp Met Val Val Asp Glu Cys Gly Cys Gly
        355                 360                 365 tagtctcggg actaggctag gagtgtgctt agggtaaatc ctttaataaa actaccaccc   1279
c                                                                   1280

<210> SEQ ID NO 42
<211> LENGTH: 366
<212> TYPE: PRT
<213> ORGANISM: Mus musculus

<400> SEQUENCE: 42

Met Gln Pro Tyr Gln Arg Leu Leu Ala Leu Gly Phe Leu Leu Leu Thr
1               5                   10                  15

Leu Pro Trp Gly Gln Thr Ser Glu Phe Gln Asp Ser Asp Leu Leu Gln
            20                  25                  30

Phe Leu Gly Leu Glu Lys Ala Pro Ser Pro His Arg Phe Gln Pro Val
        35                  40                  45

Pro Arg Val Leu Arg Lys Ile Ile Arg Ala Arg Glu Ala Ala Ala Ala
    50                  55                  60

Ser Gly Ala Ser Gln Asp Leu Cys Tyr Val Lys Glu Leu Gly Val Arg
65                  70                  75                  80

Gly Asn Leu Leu Gln Leu Pro Asp Gln Gly Phe Phe Leu Asn Thr
            85                  90                  95

Gln Lys Pro Phe Gln Asp Gly Ser Cys Leu Gln Lys Val Leu Tyr Phe
        100                 105                 110

Asn Leu Ser Ala Ile Lys Glu Lys Ala Lys Leu Thr Met Ala Gln Leu
    115                 120                 125

Thr Leu Asp Leu Gly Pro Arg Ser Tyr Tyr Asn Leu Arg Pro Glu Leu
130                 135                 140

Val Val Ala Leu Ser Val Val Gln Asp Arg Gly Val Trp Gly Arg Ser
145                 150                 155                 160

His Pro Lys Val Gly Arg Leu Leu Phe Leu Arg Ser Val Pro Gly Pro
            165                 170                 175

Gln Gly Gln Leu Gln Phe Asn Leu Gln Gly Ala Leu Lys Asp Trp Ser
        180                 185                 190

Ser Asn Arg Leu Lys Asn Leu Asp Leu His Leu Glu Ile Leu Val Lys
    195                 200                 205

Glu Asp Arg Tyr Ser Arg Val Thr Val Gln Pro Glu Asn Pro Cys Asp
210                 215                 220

Pro Leu Leu Arg Ser Leu His Ala Ser Leu Leu Val Val Thr Leu Asn
```

```
                       225                 230                 235                 240
        Pro Lys His Cys His Pro Ser Ser Arg Lys Arg Ala Ala Ile Ser
                           245                 250                 255

Val Pro Lys Gly Phe Cys Arg Asn Phe Cys His Arg His Gln Leu Phe
                       260                 265                 270

Ile Asn Phe Gln Asp Leu Gly Trp His Lys Trp Val Ile Ala Pro Lys
                   275                 280                 285

Gly Phe Met Ala Asn Tyr Cys His Gly Glu Cys Pro Phe Ser Met Thr
                   290                 295                 300

Thr Tyr Leu Asn Ser Ser Asn Tyr Ala Phe Met Gln Ala Leu Met His
        305                 310                 315                 320

Met Ala Asp Pro Lys Val Pro Lys Ala Val Cys Val Pro Thr Lys Leu
                           325                 330                 335

Ser Pro Ile Ser Met Leu Tyr Gln Asp Ser Asp Lys Asn Val Ile Leu
                       340                 345                 350

Arg His Tyr Glu Asp Met Val Val Asp Glu Cys Gly Cys Gly
                           355                 360                 365

<210> SEQ ID NO 43
        <211> LENGTH: 1224
        <212> TYPE: DNA
        <213> ORGANISM: Homo sapiens
        <220> FEATURE:
        <221> NAME/KEY: CDS
        <222> LOCATION: (37)..(1128)

<400> SEQUENCE: 43
ggagctctcc ccggtctgac agccactcca gaggcc atg ctt cgt ttc ttg cca            54
                                                Met Leu Arg Phe Leu Pro
                                                  1               5 gat ttg gct ttc agc ttc ctg tta att ctg gct ttg ggc cag gca gtc          102
        Asp Leu Ala Phe Ser Phe Leu Leu Ile Leu Ala Leu Gly Gln Ala Val
                        10                  15                  20 caa ttt caa gaa tat gtc ttt ctc caa ttt ctg ggc tta gat aag gcg          150
        Gln Phe Gln Glu Tyr Val Phe Leu Gln Phe Leu Gly Leu Asp Lys Ala
                    25                  30                  35 cct tca ccc cag aag ttc caa cct gtg cct tat atc ttg aag aaa att          198
        Pro Ser Pro Gln Lys Phe Gln Pro Val Pro Tyr Ile Leu Lys Lys Ile
            40                  45                  50 ttc cag gat cgc gag gca gca gcg acc act ggg gtc tcc cga gac tta          246
        Phe Gln Asp Arg Glu Ala Ala Ala Thr Thr Gly Val Ser Arg Asp Leu
        55                  60                  65                  70 tgc tac gta aag gag ctg ggc gtc cgc ggg aat gta ctt cgc ttt ctc          294
        Cys Tyr Val Lys Glu Leu Gly Val Arg Gly Asn Val Leu Arg Phe Leu
                        75                  80                  85 cca gac caa ggt ttc ttt ctt tac cca aag aaa att tcc caa gct tcc          342
        Pro Asp Gln Gly Phe Phe Leu Tyr Pro Lys Lys Ile Ser Gln Ala Ser
                    90                  95                 100 tcc tgc ctg cag aag ctc ctc tac ttt aac ctg tct gcc atc aaa gaa          390
        Ser Cys Leu Gln Lys Leu Leu Tyr Phe Asn Leu Ser Ala Ile Lys Glu
                105                 110                 115 agg gaa cag ttg aca ttg gcc cag ctg ggc ctg gac ttg ggg ccc aat          438
        Arg Glu Gln Leu Thr Leu Ala Gln Leu Gly Leu Asp Leu Gly Pro Asn
        120                 125                 130 tct tac tat aac ctg gga cca gag ctg gaa ctg gct ctg ttc ctg gtt          486
        Ser Tyr Tyr Asn Leu Gly Pro Glu Leu Glu Leu Ala Leu Phe Leu Val
        135                 140                 145                 150 cag gag cct cat gtg tgg ggc cag acc acc cct aag cca ggt aaa atg          534
        Gln Glu Pro His Val Trp Gly Gln Thr Thr Pro Lys Pro Gly Lys Met
                        155                 160                 165
```

| | | | | | | | | | | | | | | |
|---|---|---|---|---|---|---|---|---|---|---|---|---|---|---|
| ttt | gtg | ttg | cgg | tca | gtc | cca | tgg | cca | caa | ggt | gct | gtt | cac | ttc | aac | 582 |
| Phe | Val | Leu | Arg | Ser | Val | Pro | Trp | Pro | Gln | Gly | Ala | Val | His | Phe | Asn |
| | | 170 | | | | | 175 | | | | | 180 | | | |

```
ttt gtg ttg cgg tca gtc cca tgg cca caa ggt gct gtt cac ttc aac    582
Phe Val Leu Arg Ser Val Pro Trp Pro Gln Gly Ala Val His Phe Asn
            170                 175                 180 ctg ctg gat gta gct aag gat tgg aat gac aac ccc cgg aaa aat ttc    630
Leu Leu Asp Val Ala Lys Asp Trp Asn Asp Asn Pro Arg Lys Asn Phe
            185                 190                 195 ggg tta ttc ctg gag ata ctg gtc aaa gaa gat aga gac tca ggg gtg    678
Gly Leu Phe Leu Glu Ile Leu Val Lys Glu Asp Arg Asp Ser Gly Val
    200                 205                 210 aat ttt cag cct gaa gac acc tgt gcc aga cta aga tgc tcc ctt cat    726
Asn Phe Gln Pro Glu Asp Thr Cys Ala Arg Leu Arg Cys Ser Leu His
215                 220                 225                 230 gct tcc ctg ctg gtg gtg act ctc aac cct gat cag tgc cac cct tct    774
Ala Ser Leu Leu Val Val Thr Leu Asn Pro Asp Gln Cys His Pro Ser
                235                 240                 245 cgg aaa agg aga gca gcc atc cct gtc ccc aag ctt tct tgt aag aac    822
Arg Lys Arg Arg Ala Ala Ile Pro Val Pro Lys Leu Ser Cys Lys Asn
            250                 255                 260 ctc tgc cac cgt cac cag cta ttc att aac ttc cgg gac ctg ggt tgg    870
Leu Cys His Arg His Gln Leu Phe Ile Asn Phe Arg Asp Leu Gly Trp
        265                 270                 275 cac aag tgg atc att gcc ccc aag ggg ttc atg gca aat tac tgc cat    918
His Lys Trp Ile Ile Ala Pro Lys Gly Phe Met Ala Asn Tyr Cys His
    280                 285                 290 gga gag tgt ccc ttc tca ctg acc atc tct ctc aac agc tcc aat tat    966
Gly Glu Cys Pro Phe Ser Leu Thr Ile Ser Leu Asn Ser Ser Asn Tyr
295                 300                 305                 310 gct ttc atg caa gcc ctg atg cat gcc gtt gac cca gag atc ccc cag   1014
Ala Phe Met Gln Ala Leu Met His Ala Val Asp Pro Glu Ile Pro Gln
                315                 320                 325 gct gtg tgt atc ccc acc aag ctg tct ccc att tcc atg ctc tac cag   1062
Ala Val Cys Ile Pro Thr Lys Leu Ser Pro Ile Ser Met Leu Tyr Gln
            330                 335                 340 gac aat aat gac aat gtc att cta cga cat tat gaa gac atg gta gtc   1110
Asp Asn Asn Asp Asn Val Ile Leu Arg His Tyr Glu Asp Met Val Val
        345                 350                 355 gat gaa tgt ggg tgt ggg taggatgtca gaatgggaa tagaaggagt           1158
Asp Glu Cys Gly Cys Gly
        360 gttcttaggg taaatctttt aataaaacta cctatctggt ttatgaccac ttagatcgaa   1218 atgtca                                                             1224

<210> SEQ ID NO 44
<211> LENGTH: 364
<212> TYPE: PRT
<213> ORGANISM: Homo sapiens

<400> SEQUENCE: 44

Met Leu Arg Phe Leu Pro Asp Leu Ala Phe Ser Phe Leu Leu Ile Leu
1               5                   10                  15

Ala Leu Gly Gln Ala Val Gln Phe Gln Glu Tyr Val Phe Leu Gln Phe
            20                  25                  30

Leu Gly Leu Asp Lys Ala Pro Ser Pro Gln Lys Phe Gln Pro Val Pro
        35                  40                  45

Tyr Ile Leu Lys Lys Ile Phe Gln Asp Arg Glu Ala Ala Ala Thr Thr
    50                  55                  60

Gly Val Ser Arg Asp Leu Cys Tyr Val Lys Glu Leu Gly Val Arg Gly
65                  70                  75                  80
```

```
                Asn Val Leu Arg Phe Leu Pro Asp Gln Gly Phe Phe Leu Tyr Pro Lys
                            85                  90                  95

Lys Ile Ser Gln Ala Ser Ser Cys Leu Gln Lys Leu Leu Tyr Phe Asn
                            100                 105                 110

Leu Ser Ala Ile Lys Glu Arg Glu Gln Leu Thr Leu Ala Gln Leu Gly
                            115                 120                 125

Leu Asp Leu Gly Pro Asn Ser Tyr Tyr Asn Leu Gly Pro Glu Leu Glu
                            130                 135                 140

Leu Ala Leu Phe Leu Val Gln Glu Pro His Val Trp Gly Gln Thr Thr
                145                 150                 155                 160

Pro Lys Pro Gly Lys Met Phe Val Leu Arg Ser Val Pro Trp Pro Gln
                            165                 170                 175

Gly Ala Val His Phe Asn Leu Leu Asp Val Ala Lys Asp Trp Asn Asp
                            180                 185                 190

Asn Pro Arg Lys Asn Phe Gly Leu Phe Leu Glu Ile Leu Val Lys Glu
                            195                 200                 205

Asp Arg Asp Ser Gly Val Asn Phe Gln Pro Glu Asp Thr Cys Ala Arg
                            210                 215                 220

Leu Arg Cys Ser Leu His Ala Ser Leu Leu Val Val Thr Leu Asn Pro
                225                 230                 235                 240

Asp Gln Cys His Pro Ser Arg Lys Arg Arg Ala Ala Ile Pro Val Pro
                            245                 250                 255

Lys Leu Ser Cys Lys Asn Leu Cys His Arg His Gln Leu Phe Ile Asn
                            260                 265                 270

Phe Arg Asp Leu Gly Trp His Lys Trp Ile Ile Ala Pro Lys Gly Phe
                            275                 280                 285

Met Ala Asn Tyr Cys His Gly Glu Cys Pro Phe Ser Leu Thr Ile Ser
                            290                 295                 300

Leu Asn Ser Ser Asn Tyr Ala Phe Met Gln Ala Leu Met His Ala Val
                305                 310                 315                 320

Asp Pro Glu Ile Pro Gln Ala Val Cys Ile Pro Thr Lys Leu Ser Pro
                            325                 330                 335

Ile Ser Met Leu Tyr Gln Asp Asn Asn Asp Asn Val Ile Leu Arg His
                            340                 345                 350

Tyr Glu Asp Met Val Val Asp Glu Cys Gly Cys Gly
                            355                 360
```